United States Patent
Pavlakis (12)

(10) Patent No.: US 6,656,706 B2
(45) Date of Patent: Dec. 2, 2003

(54) MOLECULAR CLONES WITH MUTATED HIV GAG/POL, SIV GAG AND SIV ENV GENES

(75) Inventor: George N. Pavlakis, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/872,733

(22) Filed: Jun. 1, 2001

(65) Prior Publication Data

US 2001/0036655 A1 Nov. 1, 2001

Related U.S. Application Data

(63) Continuation-in-part of application No. PCT/US00/34985, filed on Dec. 22, 2000.
(60) Provisional application No. 60/173,036, filed on Dec. 23, 1999.

(51) Int. Cl.[7] .......................... C12P 21/06; C12N 15/63
(52) U.S. Cl. .................. 435/69.1; 435/320.1; 435/325; 435/91.4; 435/252.3; 435/455; 536/23.1; 514/44; 424/93.2
(58) Field of Search .............................. 435/320.1, 325, 435/455, 252.3, 69.1, 91.4; 536/23.1; 514/44; 424/93.2

(56) References Cited

U.S. PATENT DOCUMENTS

| 5,786,464 A | 7/1998 | Seed et al. |
| 5,795,737 A | 8/1998 | Seed et al. |
| 5,965,726 A | 10/1999 | Pavlakis et al. |
| 5,972,596 A | 10/1999 | Pavlakis et al. |
| 6,114,148 A | 9/2000 | Seed et al. |
| 6,174,666 B1 | 1/2001 | Pavlakis et al. |

FOREIGN PATENT DOCUMENTS

| WO | WO 90/11092 | 10/1990 |
| WO | WO 93/20212 | 10/1993 |
| WO | WO 96/09378 | 3/1996 |
| WO | WO 97/11086 | 3/1997 |
| WO | WO 98/12207 | 3/1998 |
| WO | WO 98/17816 | 4/1998 |
| WO | WO 98/34640 | 8/1998 |
| WO | WO 98/46083 | 10/1998 |
| WO | WO 99/04026 | 1/1999 |
| WO | WO 99/15641 | 4/1999 |
| WO | WO 99/30742 | 6/1999 |
| WO | WO 99/51754 | 10/1999 |
| WO | WO 99/61596 | 12/1999 |
| WO | WO 00/39302 | 7/2000 |
| WO | WO 00/39303 | 7/2000 |
| WO | WO 00/39304 | 7/2000 |
| WO | WO 00/65076 | 11/2000 |

OTHER PUBLICATIONS

McCluskie et al. Route and method of delivery of DNA vaccine influence immune responses in mice and non–human primates pp. 287–300 1999.*
Verma et al. Gene therapy promises, problems and prospects pp. 239–242 vol. 389 1997.*
Schneider et al. Cell Biochem, 1995 Suppl. 21B, 197.*
Anderson Human gene therapy pp. 25–30 vol. 392 1998.*
Azevedo et al. Main features of DNA–based immunization vectors pp. 147–153 1999.*
Nathanson et al. Biological considerations in the development of a human immunodeficiency virus vaccine pp. 579–589 2000.*
Walther et al., Viral Vector for Gene Transfer, Aug. 2000, Drugs, vol. 60, No. 2, pp. 249–271.*
Mountain et al., Gene therapy: the first decade, Mar. 2000, Tibtech, vol. 18, pp. 119–128.*
Mountain et a., Gene therapy: the first decade, Mar. 2000, Tibtech, vol. 18, pp. 119–127.*
Crystal, Transfer of Genes to Humans: Early Lessons and Obstacles to Success, Oct. 20, 1995, Science, vol. 270, pp. 404–409.*
Miller et al., Targeted vector for gene therapy, Feb. 1995, The Faseb Journal, vol. 9, pp. 190–199.*
Schneider et al., Inactivation of the Human Immunodeficiency Virus Type 1 Inhibitory . . . , Jul. 1997, Journal of Virology, vol. 71, No. 7, pp. 4892–4903.*
Moritz et al., J. Clin. Invest., 93:1451–1457, 1994.*
Riddell et al. (Nature Medicine, vol. 2, 2:216–223, 1996).*
Webster et al. (BioDrugs, 4, pp. 273–292, 1997).*
Piscitelli et al., The Annals of Pharmacotherapy, vol. 30, pp. 62–76, 1996.*
Ngo et al., "*Comutational Complexity, Protein Structure Prediction, and the Levinthal Paradox,*" *The Protein Folding Problem and Tertiary Structure Prediction*, K. Merz, Jr. and S. Le Grand, Editors (1994) pp. 491–495.
Akkina, R.K. et al., "High–Efficiency Gene Transfer into CD34+ Cells with a Human Immunodeficiency Virus Type 1–Based Retroviral Vector Pseudotyped with Vesicular Stomatitis Virus Envelope Glycoprotein G", J. Virology, 70:2581–2585 (1996).
Amado, R. G. et al., "Lentiviral Vectors—the Promise of Gene Therapy Within Reach?", Science, 285:674–676 (Jul. 1999).

(List continued on next page.)

*Primary Examiner*—Dave T. Nguyen
(74) *Attorney, Agent, or Firm*—Townsend and Townsend and Crew LLP

(57) ABSTRACT

Nucleic acid constructs containing HIV-1 gag/pol and SIV gag or SIV env genes which have been mutated to remove or reduce inhibitory/instability sequences are disclosed. Viral particles and host cells containing these constructs and/or viral particles are also disclosed. The exemplified constructs and viral particles of the invention may be useful in gene therapy for numerous disorders, including HIV infection, or as a vaccine for HIV-1 immunotherapy and immunoprophylaxis.

22 Claims, 45 Drawing Sheets

OTHER PUBLICATIONS

Figure 5:
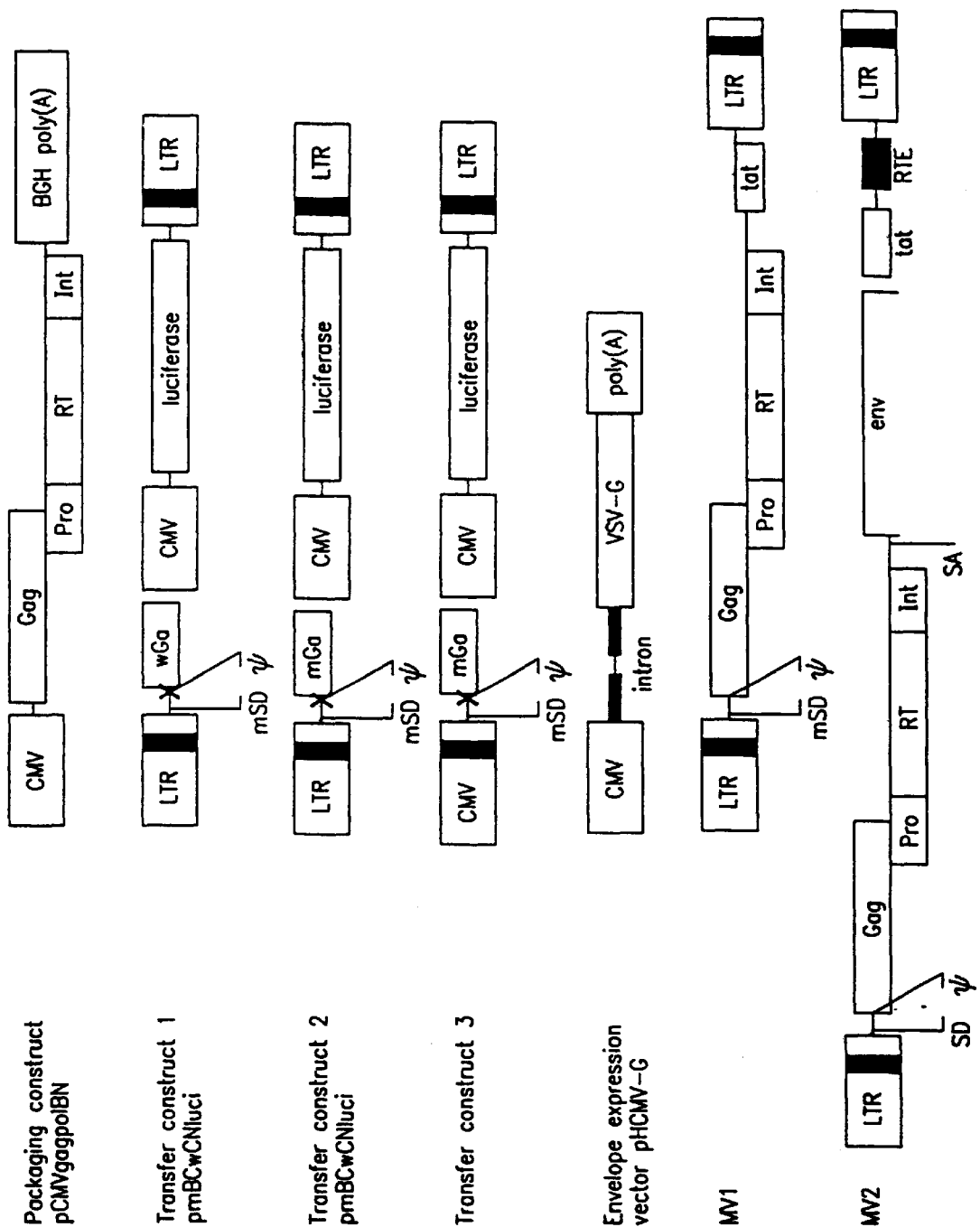

Donahue, R.E. et al., "Transplantation of Immunoselected CD34⁺ Cells Transduced with a EGFP–Expressing Lentiviral Vector in Non–Human Primates", Blood, 92 (Suppl. 1):383b, Abstract #4648.5 (1998).

Fox, J.L., "Researchers wary of fear–based ban on lentivirus gene therapy", Nature Biotechnology, 16:407–408 (1998).

Goldman, M.J. et al., "Lentiviral Vectors for Gene Therapy of Cystic Fibrosis", Human Gene Therapy, 8:2261–2268 (1997).

Kafri, T. et al., "Sustained expression of genes delivered directly into liver and muscle by lentiviral vectors", Nature Genetics, 17:314–317 (1997).

Kafri, T. et al., "A Packaging Cell Line for Lentivirus Vectors", J. Virol., 73:576–584 (1999).

Kim, V.N. et al., "Minimal Requirement for a Lentivirus Vector Based on Human Immunodeficiency Virus Type 1", J. Virol., 72:811–816 (1998).

Klimatcheva, E. et al., "Lentiviral Vectors and Gene Therapy", Frontiers in Bioscience, 4:d481–496 (Jun. 1999).

Kotsopoulou, E. et al., "A Rev–Independent Human Immunodeficiency Virus Type 1 (HIV–1)–Based Vector That Exploits a Codon–Optimized HIV-1 gag–pol Gene", J. Virol., 74:4839–4852 (2000).

Miyoshi, H. et al., "Stable and efficient gene transfer into the retina using an HIV–based lentiviral vector", Proc. Natl. Acad. Sci. USA, 94:10319–10323 (1997).

Miyoshi, H. et al., "Development of a Self–Inactivating Lentivirus Vector", J. Virol., 72:8150–8157 (1998).

Miyoshi, H. et al., "Transduction of Human CD34⁺ Cells That Mediate Long–Term Engraftment of NOD/SCID Mice by HIV Vectors", Science, 283:682–686 (1999).

Naldini, L. et al., "In Vivo Gene Delivery and Stable Transduction of Nondividing Cells by a Lentiviral Vector", Science, 272:263–267 (1996).

Naviaux, R.K. et al., "The pCL Vector System: Rapid Production of Helper–Free, High–Titer, Recombinant Retroviruses", J. Virol., 70:5701–5705 (1996).

Poeschla, E.M. et al., "Efficient transduction of nondividing human cells by feline immunodeficiency virus lentiviral vectors", Nature Med., 4:354–357 (1998).

Reynolds, P.N. et al., "Viral vectors show promise in Colorado", Nature Biotechnology, 16:422–423 (1998).

Soneoka, Y. et al., "A transient three–plasmid expression system for the production of high titer retroviral vectors", Nuc. Acids Res., 23:628–633 (1995).

Srinivasakumar, N. et al., "The Effect of Viral Regulatory Protein Expression on Gene Delivery by Human Immunodeficiency Virus Type 1 Vectors Produced in Stable Packaging Cell Lines", J. Virol., 71:5841–5848 (1997).

Sutton, R.E. et al., "Human Immunodeficiency Virus Type 1 Vectors Efficiently Transduce Human Hematopoietic Stem Cells", J. Virol., 72:5781–5788 (1998).

Takahashi, M. et al., "Rescue from Photoreceptor Degeneration in the rd Mouse by Human Immunodeficiency Virus Vector–Mediated Gene Transfer", J. Virol., 73:7812–7816 (Sep. 1999).

Uchida, N. et al., "HIV, but not murine leukemia virus, vectors mediate high efficiency gene transfer into freshly isolated $G_0/G_1$ human hematopoietic stem cells", Proc. Natl. Acad. Sci. USA, 95:11939–11944 (1998).

Vinner, L. et al., "Gene gun DNA vaccination with Rev–independent synthetic HIV–1 gp160 envelope gene using mammalian codons", Vaccine, 17:2166–2175 (1999).

Wagner, R. et al., "Rev–Independent Expression of Synthetic gag–pol Genes of Human Immunodeficiency Virus Type 1 and Simian Immunodeficiency Virus: Implications for the Safety of Lentiviral Vectors", Human Gene Therapy, 11:2403–2413 (2000).

White, S.M. et al., "Lentivirus Vectors Using Human and Simian Immunodeficiency Virus Elements", J. Virol, 73:2832–2840 (1999).

Wolff, J.A. et al., "The Cambrian period of nonviral gene delivery", Nature Biotechnology, 16:421–422(1998).

Zufferey, R. et al., "Multiply attenuated lentiviral vector achieves efficient gene delivery in vivo", Nature Biotechnology, 15:871–875 (1997).

Zufferey, R. et al., "Self–Inactivating Lentivirus Vector for Safe and Efficienct In Vivo Gene Delivery", 72:9873–9880 (1998).

Nappi F, Schneider R, Zolotukhin A, Smulevitch S, Michalowski D, Bear J. Felber BK, and Pavlakis GN. "Identification of a Novel Posttranscriptional Regulatory Element by Using a rev– and RRE–Mutated Human Immunodeficiency Virus Type 1 DNA Proviral Clone as a Molecular Trap." J Virol. May 2001;75(10):4558–69.

Qiu JT, Liu B, Tian C, Pavlakis GN, Yu XF. "Enhancement of primary and secondary cellular immune responses against human immunodeficiency virus type 1 gag by using DNA expression vectors that target Gag antigen to the secretory pathway" J Virol. Jul. 2000;74(13):5997–6005.

Qiu JT, Song R, Dettenhofer M, Tian C, August T, Felber BK, Pavlakis GN, Yu XF. "Evaluation of novel human immunodeficiency virus type 1 Gag DNA vaccines for protein expression in mammalian cells and induction of immune responses." J Virol. Nov. 1999;73(11):9145–52.

Schneider R, Campbell M, Nasioulas G, Felber BK, Pavlakis GN. "Inactivation of the human immunodeficiency virus type 1 inhibitory elements allows Rev–independent expression of Gag and Gag/protease and particle formation." J Virol. Jul. 1997;71(7):4892–903.

Afonina E, Neumann M, Pavlakis GN. "Preferential binding of poly(A)–binding protein 1 to an inhibitory RNA element in the human immunodeficiency virus type 1 gag mRNA." J Biol Chem. 1997 Jan. 24;272(4):2307–11.

Schwartz S, Campbell M, Nasioulas G, Harrison J, Felber BK, Pavlakis GN. "Mutational inactivation of an inhibitory sequence in human immunodeficiency virus type 1 results in Rev–independent gag expression." J Virol. Dec. 1992; 66 (12):7176–82.

Andre S, Seed B, Eberle J, Schraut W, Bultmann A, Haas J. "Increased immune response elicited by DNA vaccination with a synthetic gp120 sequence with optimized codon usage." J Virol. Feb. 1998; 72(2):1497–503.

Haas J, Park EC, Seed B. "Codon usage limitation in the expression of HIV–1 envelope glycoprotein." Curr Biol. Mar. 1, 1996;6(3):315–24.

Ikemura, T. "Codon Usage and tRNA Content in Unicellular and Multicellular Organisms." Mol. Biol. Evol. 2(1):13–34 (1985).

T. Maruyama et al., "Codon usage tabulated from the GenBank genetic sequence data", Nucl. Acids Res. 14:r151–r197 (1986).

S. Aota et al., "Codon usage tabulated from the GenBank genetic sequence data", Nucl. Acids Res. 16:r315–r402 (1988).

Shiver, et al., "DNA Vaccine–Mediated Cellular Immunity Against HIV–1 gag And env," abstract from the Conference on Advances in aids Vaccine Development; 8th Annual Meeting of the National Cooperative Vaccine Development Groups for AIDS (NCVDGs), Feb. 11–15, 1996.

Albert B Sabin, "Improbability of effective vaccination against human immunodeficiency virus because of its intracellular transmission and rectal portal of entry", Proc. Natl. Acad. Sci. USA, 89:8852–8855 (Sep. 1992) ("Reference 1").

Saladin Osmanov et al., "HIV–1 Genetic Variability: Implications for the Development of HIV Vaccines", Antibiotics and Chemotherapy, 48:30–38 (1996) ("Reference 2").

Kavita S. Lole, et al., "Full–Length Human Immunodeficiency Virus Type 1 Genomes from Subtype C–Infected Seroconverters in India, with Evidence of Intersubtype Recombination", Journal of Virology, 73:152–160 (Jan. 1999) ("Reference 3").

"Nikkei Biotechnology Annual Report '98", Ed. Nikkei Biotech, (Nov. 30, 1997), Nikkei Business Publications, Inc., p. 214 (English translation of table on p. 214, lines 30–35 entitled "The recent stream of research and development on AIDS") ("Reference 4").

R.I. Connor, et al., "Immunological and Virological Analyses of Persons Infected by Human Immunodeficiency Virus Type 1 while Participating in Trials of Recombinant gp120 Subunit Vaccines", Journal of Virology, 72:1552–1576 (Feb. 1998) ("Reference 5").

"Nikkei Biotechnology Annual Report '97", Ed. Nikkei Biotech, (Nov. 30, 1996), Nikkei Business Publications, Inc., p. 246 (English translation of a table on p. 246, lines 43–46 entitled "The recent stream of biotechnological research on AIDS") ("Reference 6").

"Nikkei Biotechnology Annual Report '99", Ed. Nikkei Biotech, (Nov. 30, 1998), Nikkei Business Publications, Inc., p. 79 (English translation of table on p. 79, lines 14–17 entitled "The main stream of research and development on AIDS") ("Reference 7").

Ulmer JB., Donnelly JJ., Parker SE., Rhodes GH., Felgner PL., Dwarki VJ., Gromkowski SH., Deck RR., DeWitt CM., Friedman A., Hawe LA., Leander KR., Martinez D., Perry HC., Shiver JW., Montgomery DL., Liu MA. "Heterologous Protection Against Influenza by Injection of DNA Encoding a Viral Protein." Science 259:1745–1748 (Mar. 19, 1993).

Afonina E., Stauber R. Pavlakis GN. "The Human Poly-(A)–binding Protein 1 Shuttles between the Nucleus and the Cytoplasm", The Journal of Biological Chemistry, 273:13015–13021 (May 22, 1998).

Solomin L., Felber BK., Pavlakis GN. "Different Sites of Interaction for Rev, Tev, and Rex Proteins within the Rev–Responsive Element of Human Immunodeficiency Virus Type 1", Journal of Virology, 64:6010–6017 (Dec. 1990).

Benko DM., Robinson R., Solomin, L., Mellini M., Felber BK., Pavlakis, GN. "Binding of Trans–Dominant Mutant Rev Protein of Human Immunodeficiency Virus Type 1 to the Cis–Acting Rev–Responsive Element Does Not Affect the Fate of Viral mRNA", The New Biologist, 2:1111–1122 (Dec. 1990).

Schwartz S., Felber BK., Pavlakis GN., "Distinct RNA Sequences in the gag Region of Human Immunodeficiency Virus Type 1 Decrease RNA Stability and Inhibit Expression in the Absence of Rev Protein", Journal of Virology, 66:150–159 (Jan. 1992).

D'Agostino DM., Felber BK., Harrison JE., Pavlakis GN. "The Rev Protein of Human Immunodeficiency Virus Type 1 Promotes Polysomal Association and Translation of gag/pol and vpu/env mRNAs", Molecular and Cellular Biology, 12:1375–1386 (Mar. 1992).

Myers G., Pavlakis GN. "Evolutionary Potential of Complex Retroviruses", The Retroviridae, 1:51–105 (1992).

Zolotukhin AS., Valentin A., Pavlakis GN., Felber BK. "Continuous Propagation of RRE($-$) and Rev($^{13}$)RRE($-$) Human Immunodeficiency Virus Type 1 Molecular Clones Containing a cis–Acting Element of Simian Retrovirus Type 1 in Human Peripheral Blood Lymphocytes", Journal of Virology, 68:7944–7952 (Dec. 1994).

Tan W., Felber BK., Zolotukhin AS., Pavlakis GN., Schwartz S. "Efficient Expression of the Human Papillomavirus Type 16 L1 Protein in Epithelial Cells by Using Rev and the Rev–Responsive Element of Human Immunodeficiency Virus or the cis–Acting Transactivation Element of Simian Retrovirus Type 1", Journal of Virology, 69:5607–5620 (Sep. 1995).

Wolff JA., Malone RW., Williams P., Chong W., Acsadi G., Jani A., Felgner PL. "Direct Gene Transfer into Mouse Muscle in Vivo" Science, 247:1465–1468 (Mar. 23, 1990).

Wolff JA., Ludtke JJ., Acsadi G., Williams P., Jani A. "Long–term persistence of plasmid DNA and foreign gene expression in mouse muscle", Human Molecular Genetics, 1(6):363–369 (1992).

Egan MA., Charini WA., Kuroda MJ., Schmitz JE., Racz P., Tenner–Racz K., Manson K., Wyand M., Lifton MA., Nickerson CE., Fu T., Shiver JW., Letvin NL. "Simian Immunodeficiency Virus (SIV) gag DNA–Vaccinated Rhesus Monkeys Develop Secondary Cytotoxic T–Lymphocyte Responses and Control Viral Replication after Pathogenic SIV Infection" Journal of Virology, 74(16):7485–7495 (Aug. 2000).

* cited by examiner

ATGGGTGCGAGAGCGTCAGTATTAAGCGGGGGAGAATTAGATCGATGGGAAAAAT

TCGGTTAAGGCCAGGGGGAAAGAAGAAGTACAAGCTAAAGCACATCGTATGGGCAA

GCAGGGAGCTAGAACGATTCGCAGTTAATCCTGGCCTGTTAGAAACATCAGAAGGC

TGTAGACAAATACTGGGACAGCTACAACCATCCCTTCAGACAGGATCAGAGGAGCT

TCGATCACTATACAACACAGTAGCAACCCTCTATTGTGTGCACCAGCGGATCGAGA

TCAAGGACACCAAGGAAGCTTTAGACAAGATAGAGGAAGAGCAAAACAAGTCCAAG

AAGAAGGCCCAGCAGGCAGCAGCTGACACAGGACACAGCAATCAGGTCAGCCAAAA

TTACCCTATAGTGCAGAACATCCAGGGGCAAATGGTACATCAGGCCATATCACCTA

GAACTTTAAATGCATGGGTAAAAGTAGTAGAAGAGAAGGCTTTCAGCCCAGAAGTG

ATACCCATGTTTTCAGCATTATCAGAAGGAGCCACCCCACAGGACCTGAACACGAT

GTTGAACACCGTGGGGGGACATCAAGCAGCCATGCAAATGTTAAAAGAGACCATCA

ATGAGGAAGCTGCAGAATGGGATAGAGTGCATCCAGTGCATGCAGGGCCTATTGCA

CCAGGCCAGATGAGAGAACCAAGGGGAAGTGACATAGCAGGAACTACTAGTACCCT

TCAGGAACAAATAGGATGGATGACAAATAATCCACCTATCCCAGTAGGAGAGATCT

ACAAGAGGTGGATAATCCTGGGATTGAACAAGATCGTGAGGATGTATAGCCCTACC

AGCATTCTGGACATAAGACAAGGACCAAAGGAACCCTTTAGAGACTATGTAGACCG

GTTCTATAAAACTCTAAGAGCTGAGCAAGCTTCACAGGAGGTAAAAAATTGGATGA

CAGAAACCTTGTTGGTCCAAAATGCGAACCCAGATTGTAAGACCATCCTGAAGGCT

CTCGGCCCAGCGGCTACACTAGAAGAAATGATGACAGCATGTCAGGGAGTAGGAGG

ACCCGGCCATAAGGCAAGAGTTTTGGCCGAGGCGATGAGCCAGGTGACGAACTCGG

CGACCATAATGATGCAGAGAGGCAACTTCCGGAACCAGCGGAAGATCGTCAAGTGC

TTCAATTGTGGCAAAGAAGGGCACACCGCCAGGAACTGCCGGGCCCCCGGAAGAA

GGGCTGTTGGAAATGTGGAAAGGAAGGACACCAAATGAAAGATTGTACTGAGAGAC

FIG. IA

AGGCTAATTTTTTAGGGAAGATCTGGCCTTCCTACAAGGGAAGGCCAGGGAATTTT

CTTCAGAGCAGACCAGAGCCAACAGCCCCACCAGAAGAGAGCTTCAGGTCTGGGGT

AGAGACAACAACTCCCCCTCAGAAGCAGGAGCCGATAGACAAGGAACTGTATCCTT

TAACTTCCCTCAGATCACTCTTTGGCAACGACCCCTCGTCACAGTAAGGATCGGGG

GGCAACTCAAGGAAGCGCTGCTCGATACAGGAGCAGATGATACAGTATTAGAAGAA

ATGAGTTTGCCAGGAAGATGGAAACCAAAAATGATAGGGGGGATCGGGGGCTTCAT

CAAGGTGAGGCAGTACGACCAGATACTCATAGAAATCTGTGGACATAAAGCTATAG

GTACAGTATTAGTAGGACCTACACCTGTCAACATAATTGGAAGAAATCTGTTGACC

CAGATCGGCTGCACCTTGAACTTCCCCATCAGCCCTATTGAGACGGTGCCCGTGAA

GTTGAAGCCGGGGATGGACGGCCCCAAGGTCAAGCAATGGCCATTGACGAAAGAGA

AGATCAAGGCCTTAGTCGAAATCTGTACAGAGATGGAGAAGGAAGGGAAGATCAGC

AAGATCGGGCCTGAGAACCCCTACAACACTCCAGTCTTCGCAATCAAGAAGAAGGA

CAGTACCAAGTGGAGAAAGCTGGTGGACTTCAGAGAGCTGAACAAGAGAACTCAGG

ACTTCTGGGAAGTTCAGCTGGGCATCCCACATCCCGCTGGGTTGAAGAAGAAGAAG

TCAGTGACAGTGCTGGATGTGGGTGATGCCTACTTCTCCGTTCCCTTGGACGAGGA

CTTCAGGAAGTACACTGCCTTCACGATACCTAGCATCAACAACGAGACACCAGGCA

TCCGCTACCAGTACAACGTGCTGCCACAGGGATGGAAGGGATCACCAGCCATCTTT

CAAAGCAGCATGACCAAGATCCTGGAGCCCTTCCGCAAGCAAAACCCAGACATCGT

GATCTATCAGTACATGGACGACCTCTACGTAGGAAGTGACCTGGAGATCGGGCAGC

ACAGGACCAAGATCGAGGAGCTGAGACAGCATCTGTTGAGGTGGGGACTGACCACA

CCAGACAAGAAGCACCAGAAGGAACCTCCCTTCCTGTGGATGGGCTACGAACTGCA

TCCTGACAAGTGGACAGTGCAGCCCATCGTGCTGCCTGAGAAGGACAGCTGGACTG

TGAACGACATACAGAAGCTCGTGGGCAAGTTGAACTGGGCAAGCCAGATCTACCCA

GGCATCAAAGTTAGGCAGCTGTGCAAGCTGCTTCGAGGAACCAAGGCACTGACAGA

FIG. IB

```
AGTGATCCCACTGACAGAGGAAGCAGAGCTAGAACTGGCAGAGAACCGAGAGATCC
TGAAGGAGCCAGTACATGGAGTGTACTACGACCCAAGCAAGGACCTGATCGCAGAG
ATCCAGAAGCAGGGGCAAGGCCAATGGACCTACCAAATCTACCAGGAGCCCTTCAA
GAACCTGAAGACAGGCAAGTACGCAAGGATGAGGGGTGCCCACACCAACGATGTGA
AGCAGCTGACAGAGGCAGTGCAGAAGATCACCACAGAGAGCATCGTGATCTGGGGC
AAGACTCCCAAGTTCAAGCTGCCCATACAGAAGGAGACATGGGAGACATGGTGGAC
CGAGTACTGGCAAGCCACCTGGATCCCTGAGTGGGAGTTCGTGAACACCCCTCCCT
TGGTGAAACTGTGGTATCAGCTGGAGAAGGAACCCATCGTGGGAGCAGAGACCTTC
TACGTGGATGGGGCAGCCAACAGGGAGACCAAGCTGGGCAAGGCAGGCTACGTGAC
CAACCGAGGACGACAGAAAGTGGTGACCCTGACTGACACCACCAACCAGAAGACTG
AGCTGCAAGCCATCTACCTAGCTCTGCAAGACAGCGGACTGGAAGTGAACATCGTG
ACAGACTCACAGTACGCACTGGGCATCATCCAAGCACAACCAGACCAATCCGAGTC
AGAGCTGGTGAACCAGATCATCGAGCAGCTGATCAAGAAGGAGAAAGTGTACCTGG
CATGGGTACCAGCACACAAAGGAATTGGAGGAAATGAACAAGTAGATAAATTAGTC
AGTGCTGGGATCCGGAAGGTGCTGTTCCTGGACGGGATCGATAAGGCCCAAGATGA
ACATGAGAAGTACCACTCCAACTGGCGCGCTATGGCCAGCGACTTCAACCTGCCAC
CTGTAGTAGCAAAAGAAATAGTAGCCAGCTGTGATAAATGTCAGCTAAAAGGAGAA
GCCATGCATGGACAAGTAGACTGTAGTCCAGGAATATGGCAGCTGGACTGCACGCA
CCTGGAGGGGAAGGTGATCCTGGTAGCAGTTCATGTAGCCAGTGGATATATAGAAG
CAGAAGTTATCCCTGCTGAAACTGGGCAGGAAACAGCATATTTTCTTTTAAAATTA
GCAGGAAGATGGCCAGTAAAAACAATACACACGGACAACGGAAGCAACTTCACTGG
TGCTACGGTTAAGGCCGCCTGTTGGTGGGCGGGAATCAAGCAGGAATTTGGAATTC
CCTACAATCCCCAATCGCAAGGAGTCGTGGAGAGCATGAACAAGGAGCTGAAGAAG
ATCATCGGACAAGTGAGGGATCAGGCTGAGCACCTGAAGACAGCAGTGCAGATGGC
```

FIG. IC

AGTGTTCATCCACAACTTCAAAAGAAAAGGGGGGATTGGGGGGTACAGTGCAGGGG

AAAGGATCGTGGACATCATCGCCACCGACATCCAAACCAAGGAGCTGCAGAAGCAG

ATCACCAAGATCCAGAACTTCCGGGTGTACTACCGCGACAGCCGCAACCCACTGTG

GAAGGGACCAGCAAAGCTCCTCTGGAAGGGAGAGGGGGCAGTGGTGATCCAGGACA

ACAGTGACATCAAAGTGGTGCCAAGGCGCAAGGCCAAGATCATCCGCGACTATGGA

AAACAGATGGCAGGTGATGATTGTGTGGCAAGTAGACAGGATGAGGATTAGAACCT

GGAAGAGCCTGGTGAAGCACCATATG (SEQUENCE ID NO:1)

FIG. ID

```
>wildtype    TGTACAGAGA TGGAAAAGGA AGGGAAAATT TCAAAAATTG
>mutated     TGTACAGAGA TGGAGAAGGA AGGGAAGATC AGCAAGATCG
#1           ..........................................
                           *   *  ***   *  *

>wildtype    GGCCTGAAAA TCCATACAAT ACTCCAGTAT TTGCCATAAA
>mutated     GGCCTGAGAA CCCCTACAAC ACTCCAGTCT TCGCAATCAA
#41          ..........................................
                    *   *  *    *           *  *  * *

>wildtype    GAAAAAAGAC AGTACTAAAT GGAGAAAATT AGTAGATTTC
>mutated     GAAGAAGGAC AGTACCAAGT GGAGAAAGCT GGTGGACTTC
#81          ..........................................
                *  * *      *  * *       ** *  * * *

>wildtype    AGAGAACTTA ATAAGAGAAC TCAAGACTTC TGGGAAGTTC
>mutated     AGAGAGCTGA ACAAGAGAAC TCAGGACTTC TGGGAAGTTC
#121         ..........................................
                 *  * *                *

>wildtype    AATTAGGAAT ACCACATCCC GCAGGGTTAA AAAAGAAAAA
>mutated     AGCTGGGCAT CCCACATCCC GCTGGGTTGA AGAAGAAGAA
#161         ..........................................
              ** *  *  *             *      *  *   *  *

>wildtype    ATCAGTAACA GTACTGGATG TGGGTGATGC ATATTTTTCA
>mutated     GTCAGTGACA GTGCTGGATG TGGGTGATGC CTACTTCTCC
#201         ..........................................
             *      *     *                  * *  * *  *

>wildtype    GTTCCCTTAG ATGAAGACTT CAGGAAATAT ACTGCATTTA
>mutated     GTTCCCTTGG ACGAGGACTT CAGGAAGTAC ACTGCCTTCA
#241         ..........................................
                     *  * *  *          *  *      *  * *

>wildtype    CCATACCTAG TATAAACAAT GAGACACCAG GGATTAGATA
>mutated     CGATACCTAG CATCAACAAC GAGACACCAG GCATCCGCTA
#281         ..........................................
              *         *  *     *            *  * ** *

>wildtype    TCAGTACAAT GTGCTTCCAC AGGGATGGAA AGGATCACCA
>mutated     CCAGTACAAC GTGCTGCCAC AGGGATGGAA GGGATCACCA
#321         ..........................................
             *        *      *                *

>wildtype    GCAATATTCC AAAGTAGCAT GACAAAAATC TTAGAGCCTT
>mutated     GCCATCTTTC AAAGCAGCAT GACCAAGATC CTGGAGCCCT
#361         ..........................................
               *  * * *     *         *  *    * *    *  *

>wildtype    TTAGAAAACA AAATCCAGAC ATAGTTATCT ATCAATACAT
>mutated     TCCGCAAGCA AAACCCAGAC ATCGTGATCT ATCAGTACAT
#401         ..........................................
              ** *  *        *       *  *        *
```

FIG. 2A

```
>wildtype    GGATGATTTG TATGTAGGAT CTGACTTAGA AATAGGGCAG
>mutated     GGACGACCTC TACGTAGGAA GTGACCTGGA GATCGGGCAG
  #441       .......................................
                * **  *      * *      * *     *

>wildtype    CATAGAACAA AAATAGAGGA GCTGAGACAA CATCTGTTGA
>mutated     CACAGGACCA AGATCGAGGA GCTGAGACAG CATCTGTTGA
  #481       .......................................
               *   *  *   * *                 *

>wildtype    GGTGGGGACT TACCACACCA GACAAAAAAC ATCAGAAAGA
>mutated     GGTGGGGACT GACCACACCA GACAAGAAGC ACCAGAAGGA
  #521       .......................................
                       *              *  * *  *

>wildtype    ACCTCCATTC CTTTGGATGG GTTATGAACT CCATCCTGAT
>mutated     ACCTCCCTTC CTGTGGATGG GCTACGAACT GCATCCTGAC
  #561       .......................................
                   *      *        *  *      *       *

>wildtype    AAATGGACAG TACAGCCTAT AGTGCTGCCA GAAAAAGACA
>mutated     AAGTGGACAG TGCAGCCCAT CGTGCTGCCT GAGAAGGACA
  #601       .......................................
                *          *    *  * *       *  * *

>wildtype    GCTGGACTGT CAATGACATA CAGAAGTTAG TGGGGAAATT
>mutated     GCTGGACTGT GAACGACATA CAGAAGCTCG TGGGCAAGTT
  #641       .......................................
                        * *                  * *    *  *

>wildtype    GAATTGGGCA AGTCAGATTT ACCCAGGGAT TAAAGTAAGG
>mutated     GAACTGGGCA AGCCAGATCT ACCCAGGCAT CAAAGTTAGG
  #681       .......................................
                *           *      *         *  *   *

>wildtype    CAATTATGTA AACTCCTTAG AGGAACCAAA GCACTAACAG
>mutated     CAGCTGTGCA AGCTGCTTCG AGGAACCAAG GCACTGACAG
  #721       .......................................
                * *  * *   *  *    *        *       *

>wildtype    AAGTAATACC ACTAACAGAA GAAGCAGAGC TAGAACTGGC
>mutated     AAGTGATCCC ACTGACAGAG GAAGCAGAGC TAGAACTGGC
  #761       .......................................
                 *  *       *      *

>wildtype    AGAAAACAGA GAGATTCTAA AAGAACCAGT ACATGGAGTG
>mutated     AGAGAACCGA GAGATCCTGA AGGAGCCAGT ACATGGAGTG
  #801       .......................................
                *       *        *  * *  *  *

>wildtype    TATTATGACC CATCAAAAGA CTTAATAGCA GAAATACAGA
>mutated     TACTACGACC CAAGCAAGGA CCTGATCGCA GAGATCCAGA
  #841       .......................................
                * *         *** *     * *      *    * *
```

FIG. 2B

```
>wildtype    AGCAGGGGCA AGGCCAATGG ACATATCAAA TTTATCAAGA
>mutated     AGCAGGGGCA AGGCCAATGG ACCTACCAAA TCTACCAGGA
 #881        .......................................
                                 * *    * *    *  *

>wildtype    GCCATTTAAA AATCTGAAAA CAGGAAAATA TGCAAGAATG
>mutated     GCCCTTCAAG AACCTGAAGA CAGGCAAGTA CGCAAGGATG
 #921        .......................................
                * *  * *   *    *      *  *  *   *

>wildtype    AGGGGTGCCC ACACTAATGA TGTAAAACAA TTAACAGAGG
>mutated     AGGGGTGCCC ACACCAACGA TGTGAAGCAG CTGACAGAGG
 #961        .......................................
                            * *   *   *  * * * *

>wildtype    CAGTGCAAAA AATAACCACA GAAAGCATAG TAATATGGGG
>mutated     CAGTGCAGAA GATCACCACA GAGAGCATCG TGATCTGGGG
 #1001       .......................................
                    * *  *  *        *       * * *

>wildtype    AAAGACTCCT AAATTTAAAC TGCCCATACA AAAGGAAACA
>mutated     CAAGACTCCC AAGTTCAAGC TGCCCATACA GAAGGAGACA
 #1041       .......................................
             *         *   * *  *                *   *

>wildtype    TGGGAAACAT GGTGGACAGA GTATTGGCAA GCCACCTGGA
>mutated     TGGGAGACAT GGTGGACCGA GTACTGGCAA GCCACCTGGA
 #1081       .......................................
                  *              *      *

>wildtype    TTCCTGAGTG GGAGTTTGTT AATACCCCTC CTTTAGTGAA
>mutated     TCCCTGAGTG GGAGTTCGTG AACACCCCTC CCTTGGTGAA
 #1121       .......................................
              *                *  *  *         * *  *

>wildtype    ATTATGGTAC CAGTTAGAGA AAGAACCCAT AGTAGGAGCA
>mutated     ACTGTGGTAT CAGCTGGAGA AGGAACCCAT CGTGGGAGCA
 #1161       .......................................
              * *       *   * *        *      * *

>wildtype    GAAACCTTCT ATGTAGATGG GGCAGCTAAC AGGGAGACTA
>mutated     GAGACCTTCT ACGTGGATGG GGCAGCCAAC AGGGAGACCA
 #1201       .......................................
               *          *   *          *          *

>wildtype    AATTAGGAAA AGCAGGATAT GTTACTAATA GAGGAAGACA
>mutated     AGCTGGGCAA GGCAGGCTAC GTGACCAACC GAGGACGACA
 #1241       .......................................
              ** *  *  *       *  *   * *  **   *

>wildtype    AAAAGTTGTC ACCCTAACTG ACACAACAAA TCAGAAGACT
>mutated     GAAAGTGGTG ACCCTGACTG ACACCACCAA CCAGAAGACT
 #1281       .......................................
             *      * *      *        *  *  *
```

FIG. 2C

```
>wildtype    GAGTTACAAG CAATTTATCT AGCTTTGCAG GATTCGGGAT
>mutated     GAGCTGCAAG CCATCTACCT AGCTCTGCAA GACAGCGGAC
#1321        ..........................................
               * *      *    *  *     *   *    ****   *

>wildtype    TAGAAGTAAA CATAGTAACA GACTCACAAT ATGCATTAGG
>mutated     TGGAAGTGAA CATCGTGACA GACTCACAGT ACGCACTGGG
#1361        ..........................................
              *      *     *  *               *   *  *

>wildtype    AATCATTCAA GCACAACCAG ATCAAAGTGA ATCAGAGTTA
>mutated     CATCATCCAA GCACAACCAG ACCAATCCGA GTCAGAGCTG
#1401        ..........................................
             *    *              *  ***   *      *  *

>wildtype    GTCAATCAAA TAATAGAGCA GTTAATAAAA AAGGAAAAGG
>mutated     GTGAACCAGA TCATCGAGCA GCTGATCAAG AAGGAGAAAG
#1441        ..........................................
               *  *  * *  *  *     * *  *  *     *  *

>wildtype    TCTATCTGGC ATGGGTACCA GCACACAAAG GAATTGGAGG
>mutated     TGTACCTGGC ATGGGTACCA GCACACAAAG GAATTGGAGG
#1481        ..........................................
              * *

>wildtype    AAATGAACAA GTAGATAAAT TAGTCAGTGC TGGAATCAGG
>mutated     AAATGAACAA GTAGATAAAT TAGTCAGTGC TGGGATCCGG
#1521        ..........................................
                                                 *  *

>wildtype    AAAGTACTAT TTTTAGATGG AATAGATAAG GCCCAAGATG
>mutated     AAGGTGCTGT TCCTGGACGG GATCGATAAG GCCCAAGATG
#1561        ..........................................
               *  * *   ** *   *   * *

>wildtype    AACATGAGAA ATATCACAGT AATTGGAGAG CAATGGCTAG
>mutated     AACATGAGAA GTACCACTCC AACTGGCGCG CTATGGCCAG
#1601        ..........................................
                        *  * ***    *   *  *    *     *

>wildtype    TGATTTTAAC CTGCCACCTG TAGTAGCAAA AGAAATAGTA
>mutated     CGACTTCAAC CTGCCACCTG TAGTAGCAAA AGAAATAGTA
#1641        ..........................................
             *  *  *

>wildtype    GCCAGCTGTG ATAAATGTCA GCTAAAAGGA GAAGCCATGC
>mutated     GCCAGCTGTG ATAAATGTCA GCTAAAAGGA GAAGCCATGC
#1681        ..........................................

>wildtype    ATGGACAAGT AGACTGTAGT CCAGGAATAT GGCAACTAGA
>mutated     ATGGACAAGT AGACTGTAGT CCAGGAATAT GGCAGCTGGA
#1721        ..........................................
                                                 *  *
```

FIG. 2D

```
>wildtype      TTGTACACAT TTAGAAGGAA AAGTTATCCT GGTAGCAGTT
>mutated       CTGCACGCAC CTGGAGGGGA AGGTGATCCT GGTAGCAGTT
 #1761         ..........................................
               *  *  *   *      *   *   *

>wildtype      CATGTAGCCA GTGGATATAT AGAAGCAGAA GTTATTCCAG
>mutated       CATGTAGCCA GTGGATATAT AGAAGCAGAA GTTATCCCTG
 #1801         ..........................................
                                                    * *

>wildtype      CAGAAACAGG GCAGGAAACA GCATATTTTC TTTTAAAATT
>mutated       CTGAAACTGG GCAGGAAACA GCATATTTTC TTTTAAAATT
 #1841         ..........................................
                *      *

>wildtype      AGCAGGAAGA TGGCCAGTAA AAACAATACA TACAGACAAT
>mutated       AGCAGGAAGA TGGCCAGTAA AAACAATACA CACGGACAAC
 #1881         ..........................................
                                                * *   *

>wildtype      GGCAGCAATT TCACCAGTGC TACGGTTAAG GCCGCCTGTT
>mutated       GGAAGCAACT TCACTGGTGC TACGGTTAAG GCCGCCTGTT
 #1921         ..........................................
                 * *    *     * **

>wildtype      GGTGGGCGGG AATCAAGCAG GAATTTGGAA TTCCCTACAA
>mutated       GGTGGGCGGG AATCAAGCAG GAATTTGGAA TTCCCTACAA
 #1961         ..........................................

>wildtype      TCCCCAAAGT CAAGGAGTAG TAGAATCTAT GAATAAAGAA
>mutated       TCCCCAATCG CAAGGAGTCG TGGAGAGCAT GAACAAGGAG
 #2001         ..........................................
                      ***        *   *  ****     *  *  *

>wildtype      TTAAAGAAAA TTATAGGACA GGTAAGAGAT CAGGCTGAAC
>mutated       CTGAAGAAGA TCATCGGACA AGTGAGGGAT CAGGCTGAGC
 #2041         ..........................................
               * *       *  * *     *  *   *             *

>wildtype      ATCTTAAGAC AGCAGTACAA ATGGCAGTAT TCATCCACAA
>mutated       ACCTGAAGAC AGCAGTGCAG ATGGCAGTGT TCATCCACAA
 #2081         ..........................................
                * *              * *        *

>wildtype      TTTTAAAAGA AAAGGGGGGA TTGGGGGGTA CAGTGCAGGG
>mutated       CTTCAAAAGA AAAGGGGGGA TTGGGGGGTA CAGTGCAGGG
 #2121         ..........................................
               *  *

>wildtype      GAAAGAATAG TAGACATAAT AGCAACAGAC ATACAAACTA
>mutated       GAAAGGATCG TGGACATCAT CGCCACCGAC ATCCAAACCA
 #2161         ..........................................
                    *  *   *      *   *  *  *     *    *
```

FIG. 2E

```
>wildtype    AAGAATTACA AAAACAAATT ACAAAAATTC AAAATTTTCG
>mutated     AGGAGCTGCA GAAGCAGATC ACCAAGATCC AGAACTTCCG
#2201        ..........  ..........  ..........  ..........
                *  **  *    *   *   *    *   *   *    *   *

>wildtype    GGTTTATTAC AGGGACAGCA GAAATCCACT TTGGAAAGGA
>mutated     GGTGTACTAC CGCGACAGCC GCAACCCACT GTGGAAGGGA
#2241        ..........  ..........  ..........  ..........
                *  *   *     *  *      *   *      *      *

>wildtype    CCAGCAAAGC TCCTCTGGAA AGGTGAAGGG GCAGTAGTAA
>mutated     CCAGCAAAGC TCCTCTGGAA GGGAGAGGGG GCAGTGGTGA
#2281        ..........  ..........  ..........  ..........
                                      *  *  *        *  *

>wildtype    TACAAGATAA TAGTGACATA AAAGTAGTGC CAAGAAGAAA
>mutated     TCCAGGACAA CAGTGACATC AAAGTGGTGC CAAGGCGCAA
#2321        ..........  ..........  ..........  ..........
              *   *  *   *           *        *     ** *

>wildtype    AGCAAAGATC ATTAGGGATT ATGGAAAACA GATGGCAGGT
>mutated     GGCCAAGATC ATCCGCGACT ATGGAAAACA GATGGCAGGT
#2361        ..........  ..........  ..........  ..........
              *  *          ** *  *

>wildtype    GATGATTGTG TGGCAAGTAG ACAGGATGAG GATTAGAACA
>mutated     GATGATTGTG TGGCAAGTAG ACAGGATGAG GATTAGAACC
#2401        ..........  ..........  ..........  ..........
                                                           *

>wildtype    TGGAAAAGTT TAGTAAAACA CCATATG    (SEQUENCE ID NO: 2)
>mutated     TGGAAGAGCC TGGTGAAGCA CCATATG    (SEQUENCE ID NO: 3)
#2441        ..........  ..........  .......
                  *  **   *   *  *
```

FIG. 2F

```
ATGGGCGTGAGAAACTCCGTCTTGTCAGGGAAGAAAGCAGATGAATTAG
AAAAAATTAGGCTACGACCCAACGGAAAGAAAAAGTACATGTTGAAGC
ATGTAGTATGGGCAGCAAATGAATTAGATAGATTTGGATTAGCAGAAAG
CCTGTTGGAGAACAAAGAAGGATGTCAAAAAATACTTTCGGTCTTAGCT
CCATTAGTGCCAACAGGCTCAGAAAATTTAAAAAGCCTTTATAATACTG
TCTGCGTCATCTGGTGCATTCACGCAGAAGAGAAAGTGAAACACACTGA
GGAAGCAAAACAGATAGTGCAGAGACACCTAGTGGTGGAAACAGGAAC
CACCGAAACCATGCCGAAGACCTCTCGACCAACAGCACCATCTAGCGGC
AGAGGAGGAAACTACCCAGTACAGCAGATCGGTGGCAACTACGTCCAC
CTGCCACTGTCCCCGAGAACCCTGAACGCTTGGGTCAAGCTGATCGAGG
AGAAGAAGTTCGGAGCAGAAGTAGTGCCAGGATTCCAGGCACTGTCAG
AAGGTTGCACCCCCTACGACATCAACCAGATGCTGAACTGCGTTGGAGA
CCATCAGGCGGCTATGCAGATCATCCGTGACATCATCAACGAGGAGGCT
GCAGATTGGGACTTGCAGCACCCACAACCAGCTCCACAACAAGGACAA
CTTAGGGAGCCGTCAGGATCAGACATCGCAGGAACCACCTCCTCAGTTG
ACGAACAGATCCAGTGGATGTACCGTCAGCAGAACCCGATCCCAGTAGG
CAACATCTACCGTCGATGGATCCAGCTGGGTCTGCAGAAATGCGTCCGT
ATGTACAACCCGACCAACATTCTAGATGTAAAACAAGGGCCAAAAGAG
CCATTTCAGAGCTATGTAGACAGGTTCTACAAAAGTTTAAGAGCAGAAC
AGACAGATGCAGCAGTAAAGAATTGGATGACTCAAACACTGCTGATTCA
AAATGCTAACCCAGATTGCAAGCTAGTGCTGAAGGGGCTGGGTGTGAAT
CCCACCCTAGAAGAAATGCTGACGGCTTGTCAAGGAGTAGGGGGGCCG
GGACAGAAGGCTAGATTAATGGCAGAAGCCCTGAAAGAGGCCCTCGCA
CCAGTGCCAATCCCTTTTGCAGCAGCCCAACAGAGGGGACCAAGAAAGC
CAATTAAGTGTTGGAATTGTGGGAAGAGGGACACTCTGCAAGGCAATG
CAGAGCCCCAAGAAGACAGGGATGCTGGAAATGTGGAAAAATGGACCA
TGTTATGGCCAAATGCCCAGACAGACAGGCGGGTTTTTAGGCCTTGGT
CCATGGGGAAAGAAGCCCCGCAATTTCCCCATGGCTCAAGTGCATCAGG
GGCTGATGCCAACTGCTCCCCCAGAGGACCCAGCTGTGGATCTGCTAAA
GAACTACATGCAGTTGGGCAAGCAGCAGAGAGAAAGCAGAGAGAAG
CAGAGAGAAGCCTTACAAGGAGGTGACAGAGGATTTGCTGCACCTCAAT
TCTCTCTTTGGAGGAGACCAGTAG    (SEQUENCE ID NO: 4)
```

FIG. 3

```
SIV gag       ------------------------------------
  #1          ....................................
              ATGGGCGTGAGAAACTCCGTCTTGTCAGGGAAGAAAGCAG SIV gag       ------------------------------------
  #41         ....................................
              ATGAATTAGAAAAAATTAGGCTACGACCCAACGGAAAGAA SIV gag       ------------------------------------
  #81         ....................................
              AAAGTACATGTTGAAGCATGTAGTATGGGCAGCAAATGAA SIV gag       ------------------------------------
  #121        ....................................
              TTAGATAGATTTGGATTAGCAGAAAGCCTGTTGGAGAACA SIV gag       ------------------------------------
  #161        ....................................
              AAGAAGGATGTCAAAAAATACTTTCGGTCTTAGCTCCATT SIV gag       ------------------------------------
  #201        ....................................
              AGTGCCAACAGGCTCAGAAAATTTAAAAAGCCTTTATAAT SIV gag       ------------------------------------
  #241        ....................................
              ACTGTCTGCGTCATCTGGTGCATTCACGCAGAAGAGAAAG SIV gag       ------------------------------------
SIVgagDX..                               ----------
  #281        ....................................
              TGAAACACACTGAGGAAGCAAAACAGATAGTGCAGAGACA SIV gag       -------------------A--A-----T-----A--A
SIVgagDX..    -------------------C--C-----C-----G--G
  #321        ....................................
              CCTAGTGGTGGAAACAGGAACMACMGAAACYATGCCRAAR SIV gag       --AAG-A-------------------------------
SIVgagDX..    --CTC-C-------------------------------
  #361        ....................................
              ACMWSTMGACCAACAGCACCATCT

```
SIV gag    -T-----------A--A--A-----------T--------
SIVgagDX..-C-----------G--G--C-----------C--------
#401       ................................
           AYTACCCAGTACARCARATMGGTGGTAACTAYGTCCACCT SIV gag    ----T-AAG----------AT-A--T--C-----A--AT--
SIVgagDX..----C-GTC----------CC-G--C--T-----C--GC--
#441       ................................
           GCCAYTRWSCCCGAGAACMYTRAAYGCYTGGGTMAARYTG SIV gag    --A-----A-----A--T---------------------
SIVgagDX..--C-----G-----G--C---------------------
#481       ................................
           ATMGAGGARAAGAARTTYGGAGCAGAAGTAGTGCCAGGAT SIV gag    -T----------------------------T-----T--
SIVgagDX..-C----------------------------C-----C--
#521       ................................
           TYCAGGCACTGTCAGAAGGTTGCACCCCCTAYGACATYAA SIV gag    T------T-A--T--T--G----------A---------
SIVgagDX..C------C-G--C--C--T----------G---------
#561       ................................
           YCAGATGYTRAAYTGYGTKGGAGACCATCARGCGGCTATG SIV gag    -----T---A-A--T--T--A------------------
SIVgagDX..-----C---C-T--C--C--C------------------
#601       ................................
           CAGATYATCMGWGAYATYATMAACGAGGAGGCTGCAGATT SIV gag    ----------------------------------------
SIVgagDX..----------------------------------------
#641       ................................
           GGGACTTGCAGCACCCACAACCAGCTCCACAACAAGGACA SIV gag    ------------------------T--T--------A--T
SIVgagDX..------------------------C--C--------C--C
#681       ................................
           ACTTAGGGAGCCGTCAGGATCAGAYATYGCAGGAACMACY SIV gag    AGT-----A--T-----A--------------A-A--A-
SIVgagDX..TCC-----T--C-----G--------------C-T--G-
#721       ................................
           WSYTCAGTWGAYGAACARATCCAGTGGATGTACMGWCARC
```

FIG. 4B

```
SIV gag      -------C--A--------------T---A-GA-------
SIVgagDX..   -------G--C--------------C---C-TC-------
#761         ............................................
             AGAACCCSATMCCAGTAGGCAACATYTACMGKMGATGGAT SIV gag      ---A-----GT----A--A--T--CA-A-----T-----A
SIVgagDX..   ---G-----TC----G--G--C--TC-T-----C-----G
#801         ............................................
             CCARCTGGGKYTGCARAARTGYGTYMGWATGTAYAACCCR SIV gag      --A-------------------------------------
SIVgagDX..   --C-------------------------------------
#841         ............................................
             ACMAACATTCTAGATGTAAAACAAGGGCCAAAAGAGCCAT SIV gag      ----------------------------------------
881         ............................................
             TTCAGAGCTATGTAGACAGGTTCTACAAAAGTTTAAGAGC SIV gag      ----------------------------------------
921         ............................................
             AGAACAGACAGATGCAGCAGTAAAGAATTGGATGACTCAA SIV gag      ----------------------------------------
961         ............................................
             ACACTGCTGATTCAAAATGCTAACCCAGATTGCAAGCTAG SIV gag      ----------------------------------------
1001        ............................................
             TGCTGAAGGGGCTGGGTGTGAATCCCACCCTAGAAGAAAT SIV gag      ----------------------------------------
1041        ............................................
             GCTGACGGCTTGTCAAGGAGTAGGGGGGCCGGGACAGAAG SIV gag      ----------------------------------------
1081        ............................................
             GCTAGATTAATGGCAGAAGCCCTGAAAGAGGCCCTCGCAC SIV gag      ----------------------------------------
1121        ............................................
             CAGTGCCAATCCCTTTTGCAGCAGCCCAACAGAGGGGACC SIV gag      ----------------------------------------
1161        ............................................
             AAGAAAGCCAATTAAGTGTTGGAATTGTGGGAAAGAGGGA
```

FIG. 4C

| | |
|---|---|
| SIV gag #1201 | ``------------------------------------``<br>``....................................``<br>CACTCTGCAAGGCAATGCAGAGCCCCAAGAAGACAGGGAT |
| SIV gag #1241 | ``------------------------------------``<br>``....................................``<br>GCTGGAAATGTGGAAAAATGGACCATGTTATGGCCAAATG |
| SIV gag #1281 | ``------------------------------------``<br>``....................................``<br>CCCAGACAGACAGGCGGGTTTTTTAGGCCTTGGTCCATGG |
| SIV gag #1321 | ``------------------------------------``<br>``....................................``<br>GGAAAGAAGCCCCGCAATTTCCCCATGGCTCAAGTGCATC |
| SIV gag #1361 | ``------------------------------------``<br>``....................................``<br>AGGGGCTGATGCCAACTGCTCCCCCAGAGGACCCAGCTGT |
| SIV gag #1401 | ``------------------------------------``<br>``....................................``<br>GGATCTGCTAAAGAACTACATGCAGTTGGGCAAGCAGCAG |
| SIV gag #1441 | ``------------------------------------``<br>``....................................``<br>AGAGAAAAGCAGAGAGAAAGCAGAGAGAAGCCTTACAAGG |
| SIV gag #1481 | ``------------------------------------``<br>``....................................``<br>AGGTGACAGAGGATTTGCTGCACCTCAATTCTCTCTTTGG |
| SIV gag #1521 | ``------------------------------------``<br>``....................................``<br>AGGAGACCAGTAG (SEQUENCE ID NO: 5) |

FIG. 4D

```
   1 CCTGGCCATT GCATACGTTG TATCCATATC ATAATATGTA CATTTATATT GGCTCATGTC CAACATTACC
  71 GCCATGTTGA CATTGATTAT TGACTAGTTA TTAATAGTAA TCAATTACGG GGTCATTAGT TCATAGCCCA
 141 TATATGGAGT TCCGCGTTAC ATAACTTACG GTAAATGGCC CGCCTGGCTG ACCGCCCAAC GACCCCCGCC
 211 CATTGACGTC AATAATGACG TATGTTCCCA TAGTAACGCC AATAGGGACT TTCCATTGAC GTCAATGGGT
 281 GGAGTATTTA CGGTAAACTG CCCACTTGGC AGTACATCAA GTGTATCATA TGCCAAGTAC GCCCCCTATT
 351 GACGTCAATG ACGGTAAATG GCCCGCCTGG CATTATGCCC AGTACATGAC CTTATGGGAC TTTCCTACTT
 421 GGCAGTACAT CTACGTATTA GTCATCGCTA TTACCATGGT GATGCGGTTT TGGCAGTACA TCAATGGGCG
 491 TGGATAGCGG TTTGACTCAC GGGGATTTCC AAGTCTCCAC CCCATTGACG TCAATGGGAG TTTGTTTTGG
 561 CACCAAAATC AACGGGACTT TCCAAAATGT CGTAACAACT CCGCCCCATT GACGCAAATG GCGGTAGGC
 631 GTGTACGGTG GAGGTCTAT ATAAGCAGAG CTCGTTTAGT GAACCGTCAG ATCGCCTGGA GACGCCATCC
                                                                  SalI     (758)
 701 ACGCTGTTTT GACCTCCATA GAAGACACCG GGACCGATCC AGCCTCCGCG GGCGCGCGTC GACAGAGAGA
 771 TGGGTGCGAG AGCGTCAGTA TTAAGCGGGG GAGAATTAGA TCGATGGGAA AAAATTCGGT TAAGGCCAGG
 841 GGGAAAGAAG AAGTACAAGC TAAAGCACAT CGTATGGGCA AGCAGGGAGC TAGAACGATT CGCAGTTAAT
 911 CCTGGCCTGT TAGAAACATC AGAAGGCTGT AGACAAATAC TGGGACAGCT ACAACCATCC CTTCAGACAG
 981 GATCAGAGGA GCTTCGATCA CTATACAACA CAGTAGCAAC CCTCTATTGT GTGCACCAGC GGATCGAGAT
1051 CAAGGACACC AAGGAAGCTT TAGACAAGAT AGAGGAAGAG CAAAACAAGT CCAAGAAGAA GGCCCAGCAG
1121 GCAGCAGCTG ACACAGGACA CAGCAATCAG GTCAGCCAAA ATTACCCTAT AGTGCAGAAC ATCCAGGGGC
1191 AAATGGTACA TCAGGCCATA TCACCTAGAA CTTTAAATGC ATGGGTAAAA GTAGTAGAAG AAGGCTTT
1261 CAGCCCAGAA GTGATACCCA TGTTTTCAGC ATTATCAGAA GGAGCCACCC CACAGGACCT GAACACGATG
1331 TTGAACACCG TGGGGGGACA TCAAGCAGCC ATGCAAATGT TAAAAGAGAC CATCAATGAG GAAGCTGCAG
1401 AATGGGATAG AGTGCATCCA GTGCATGCAG GGCCTATTGC ACCAGGCCAG ATGAGAGAAC CAAGGGGAAG
1471 TGACATAGCA GGAACTACTA GTACCCTTCA GGAACAAATA GGATGGATGA CAAATAATCC ACCTATCCCA
1541 GTAGGAGAGA TCTACAAGAG GTGGATAATC CTGGGATTGA ACAAGATCGT GAGGATGTAT AGCCCTACCA
1611 GCATTCTGGA CATAAGACAA GGACCAAAGG AACCCTTTAG AGACTATGTA GACCGGTTCT ATAAAACTCT
1681 AAGAGCTGAG CAAGCTTCAC AGGAGGTAAA AAATTGGATG ACAGAAACCT TGTTGGTCCA AAATGCGAAC
1751 CCAGATTGTA AGACCATCCT GAAGGCTCTC GGCCCAGCGG CTACACTAGA AGAAATGATG ACAGCATGTC
1821 AGGGAGTAGG AGGACCCGGC CATAAGGCAA GAGTTTTGGC CGAGGCGATG AGCCAGGTGA CGAACTCGGC
```

FIG. 9A

```
1891  GACCATAATG ATGCAGAGAG GCAACTTCCG GAACCAGCGG AAGATCGTCA AGTGCTTCAA TTGTGGCAAA
1961  GAAGGGCACA CCGCCAGGAA CTGCCGGGCC CCCCGGAAGA AGGGCTGTTG GAAATGTGGA AAGGAAGGAC
2031  ACCAAATGAA AGATTGTACT GAGAGACAGG CTAATTTTTT AGGGAAGATC TGGCCTTCCT ACAAGGGAAG
2101  GCCAGGGAAT TTTCTTCAGA GCAGACCAGA GCCAACAGCC CCACCAGAAG AGAGCTTCAG GTCTGGGGTA
2171  GAGACAACAA CTCCCCCTCA GAAGCAGGAG CCGATAGACA AGGAACTGTA TCCTTTAACT TCCCTCAGAT
2241  CACTCTTTGG CAACGACCCC TCGTCACAGT AAGGATCGGG GGCAACTCA AGGAAGCGCT GCTCGATACA
2311  GGAGCAGATG ATACAGTATT AGAAGAAATG AGTTTGCCAG GAAGATGGAA ACCAAAAATG ATAGGGGGGA
2381  TCGGGGGCTT CATCAAGGTG AGGCAGTACG ACCAGATACT CATAGAAATC TGTGGACATA AAGCTATAGG
2451  TACAGTATTA GTAGGACCTA CACCTGTCAA CATAATTGGA AGAAATCTGT TGACCCAGAT CGGCTGCACC
2521  TTGAACTTCC CCATCAGCCC TATTGAGACG GTGCCCGTGA AGTTGAAGCC GGGGATGGAC GGCCCCAAGG
2591  TCAAGCAATG GCCATTGACG AAAGAGAAGA TCAAGGCCTT AGTCGAAATC TGTACAGAGA TGGAGAAGGA
2661  AGGGAAGATC AGCAAGATCG GGCCTGAGAA CCCCTACAAC ACTCCAGTCT TCGCAATCAA GAAGAAGGAC
2731  AGTACCAAGT GGAGAAAGCT GGTGGACTTC AGAGAGCTGA ACAAGAGAAC TCAGGACTTC TGGGAAGTTC
2801  AGCTGGGCAT CCCACATCCC GCTGGGTTGA AGAAGAAGAA GTCAGTGACA GTGCTGGATG TGGGTGATGC
2871  CTACTTCTCC GTTCCCTTGG ACGAGGACTT CAGGAAGTAC ACTGCCTTCA CGATACCTAG CATCAACAAC
2941  GAGACACCAG GCATCCGCTA CCAGTACAAC GTGCTGCCAC AGGGATGGAA GGGATCACCA GCCATCTTTC
3011  AAAGCAGCAT GACCAAGATC CTGGAGCCCT TCCGCAAGCA AAACCCAGAC ATCGTGATCT ATCAGTACAT
3081  GGACGACCTC TACGTAGGAA GTGACCTGGA GATCGGGCAG CACAGGACCA AGATCGAGGA GCTGAGACAG
3151  CATCTGTTGA GGTGGGGACT GACCACACCA GACAAGAAGC ACCAGAAGGA ACCTCCCTTC CTGTGGATGG
3221  GCTACGAACT GCATCCTGAC AAGTGGACAG TGCAGCCCAT CGTGCTGCCT GAGAAGGACA GCTGGACTGT
3291  GAACGACATA CAGAAGCTCG TGGGCAAGTT GAACTGGGCA AGCCAGATCT ACCCAGGCAT CAAAGTTAGG
3361  CAGCTGTGCA AGCTGCTTCG AGGAACCAAG GCACTGACAG AAGTGATCCC ACTGACAGAG GAAGCAGAGC
3431  TAGAACTGGC AGAGAACCGA GAGATCCTGA AGGAGCCAGT ACATGGAGTG TACTACGACC CAAGCAAGGA
3501  CCTGATCGCA GAGATCCAGA AGCAGGGGCA AGGCCAATGG ACCTACCAAA TCTACCAGGA GCCCTTCAAG
3571  AACCTGAAGA CAGGCAAGTA CGCAAGGATG AGGGGTGCCC ACACCAACGA TGTGAAGCAG CTGACAGAGG
3641  CAGTGCAGAA GATCACCACA GAGAGCATCG TGATCTGGGG CAAGACTCCC AAGTTCAAGC TGCCCATACA
3711  GAAGGAGACA TGGGAGACAT GGTGGACCGA GTACTGGCAA GCCACCTGGA TCCCTGAGTG GGAGTTCGTG
```

FIG. 9B

```
3781 AACACCCCTC CCTTGGTGAA ACTGTGGTAT CAGCTGGAGA AGGAACCCAT CGTGGGAGCA GAGACCTTCT
3851 ACGTGGATGG GGCAGCCAAC AGGGAGACCA AGCTGGGCAA GGCAGGCTAC GTGACCAACC GAGGACGACA
3921 GAAAGTGGTG ACCCTGACTG ACACCACCAA CCAGAAGACT GAGCTGCAAG CCATCTACCT AGCTCTGCAA
3991 GACAGCGGAC TGGAAGTGAA CATCGTGACA GACTCACAGT ACGCACTGGG CATCATCCAA GCACAACCAG
4061 ACCAATCCGA GTCAGAGCTG TGAACCAGA TCATCGAGCA GCTGATCAAG AAGGAGAAAG TGTACCTGGC
4131 ATGGGTACCA GCACACAAAG GAATTGGAGG AAATGAACAA GTAGATAAAT TAGTCAGTGC TGGGATCCGG
4201 AAGGTGCTGT TCCTGGACGG GATCGATAAG GCCCAAGATG AACATGAGAA GTACCACTCC AACTGGCGCG
4271 CTATGGCCAG CGACTTCAAC CTGCCACCTG TAGTAGCAAA AGAAATAGTA GCCAGCTGTG ATAAATGTCA
4341 GCTAAAAGGA GAAGCCATGC ATGGACAAGT AGACTGTAGT CCAGGAATAT GGCAGCTGGA CTGCACGCAC
4411 CTGGAGGGGA AGGTGATCCT GGTAGCAGTT CATGTAGCCA GTGGATATAT AGAAGCAGAA GTTATCCCTG
4481 CTGAAACTGG GCAGGAAACA GCATATTTTC TTTTAAAATT AGCAGGAAGA TGGCCAGTAA AAACAATACA
4551 CACGGACAAC GGAAGCAACT TCACTGGTGC TACGGTTAAG GCCGCCTGTT GGTGGGCGGG AATCAAGCAG
4621 GAATTTGGAA TTCCCTACAA TCCCCAATCG CAAGGAGTCG TGGAGAGCAT GAACAAGGAG CTGAAGAAGA
4691 TCATCGGACA AGTGAGGGAT CAGGCTGAGC ACCTGAAGAC AGCAGTGCAG ATGGCAGTGT TCATCCACAA
4761 CTTCAAAAGA AAAGGGGGGA TTGGGGGGTA CAGTGCAGGG GAAAGGATCG TGGACATCAT CGCCACCGAC
4831 ATCCAAACCA AGGAGCTGCA GAAGCAGATC ACCAAGATCC AGAACTTCCG GGTGTACTAC CGCGACAGCC
4901 GCAACCCACT GTGGAAGGGA CCAGCAAAGC TCCTCTGGAA GGGAGAGGGG GCAGTGGTGA TCCAGGACAA
4971 CAGTGACATC AAAGTGGTGC AAGGCGCAA GGCCAAGATC ATCCGCGACT ATGGAAAACA GATGGCAGGT
5041 GATGATTGTG TGGCAAGTAG ACAGGATGAG GATTAGAACC TGGAAGAGCC TGGTGAAGCA CCATATGGCG
                    NheI  (5117)
           BstBI   (5111)
5111 TTCGAAGCTA GCCTCGAGAT CCAGATCTGC TGTGCCTTCT AGTTGCCAGC CATCTGTTGT TTGCCCCTCC
5181 CCCGTGCCTT CCTTGACCCT GGAAGGTGCC ACTCCCACTG TCCTTTCCTA ATAAAATGAG GAAATTGCAT
5251 CGCATTGTCT GAGTAGGTGT CATTCTATTC TGGGGGGTGG GGTGGGGCAG CACAGCAAGG GGAGGATTG
5321 GGAAGACAAT AGCAGGCATG CTGGGGATGC GGTGGGCTCT ATGCGTACCC AGGTGCTGAA GAATTGACCC
5391 GGTTCCTCCT GGGCCAGAAA GAAGCAGGCA CATCCCCTTC TCTCTGACAC ACCCTGTCCA CGCCCCTGGT
5461 TCTTAGTTCC AGCCCCACTC ATAGGACACT CATAGCTCAG GAGGGCTCCG CCTTCAATCC CACCCGCTAA
5531 AGTACTTGGA GCGGTCTCTC CCTCCCTCAT CAGCCCACCA AACCAAACCT AGCCTCCAAG AGTGGGAAGA
```

FIG. 9C

```
5601  AATTAAAGCA AGATAGGCTA TTAAGTGCAG AGGGAGAGAA AATCCCTCCA ACATGTGAGG AAGTAATGAG
5671  AGAAATCATA GAATTTCTTC CGCTTCCTCG CTCACTGACT CGCTGCGCTC GGTCGTTCGG CTGCGGCGAG
      ────────▶
5741  CGGTATCAGC TCACTCAAAG GCGGTAATAC GGTTATCCAC AGAATCAGGG GATAACGCAG GAAAGAACAT
5811  GTGAGCAAAA GGCCAGCAAA AGGCCAGGAA CCGTAAAAAG GCCGCGTTGC TGGCGTTTTT CCATAGGCTC
5881  CGCCCCCCTG ACGAGCATCA CAAAAATCGA CGCTCAAGTC AGAGGTGGCG AAACCCGACA GGACTATAAA
5951  GATACCAGGC GTTTCCCCCT GGAAGCTCCC TCGTGCGCTC TCCTGTTCCG ACCCTGCCGC TTACCGGATA
6021  CCTGTCCGCC TTTCTCCCTT CGGGAAGCGT GGCGCTTTCT CAATGCTCAC GCTGTAGGTA TCTCAGTTCG
6091  GTGTAGGTCG TTCGCTCCAA GCTGGGCTGT GTGCACGAAC CCCCCGTTCA GCCCGACCGC TGCGCCTTAT
6161  CCGGTAACTA TCGTCTTGAG TCCAACCCGG TAAGACACGA CTTATCGCCA CTGGCAGCAG CCACTGGTAA
6231  CAGGATTAGC AGAGCGAGGT ATGTAGGCGG TGCTACAGAG TTCTTGAAGT GGTGGCCTAA CTACGGCTAC
6301  ACTAGAAGGA CAGTATTTGG TATCTGCGCT CTGCTGAAGC CAGTTACCTT CGGAAAAAGA GTTGGTAGCT
6371  CTTGATCCGG CAAACAAACC ACCGCTGGTA GCGGTGGTTT TTTTGTTTGC AAGCAGCAGA TTACGCGCAG
6441  AAAAAAAGGA TCTCAAGAAG ATCCTTTGAT CTTTTCTACG GGGTCTGACG CTCAGTGGAA CGAAAACTCA
6511  CGTTAAGGGA TTTTGGTCAT GAGATTATCA AAAAGGATCT TCACCTAGAT CCTTTTAAAT TAAAAATGAA
6581  GTTTTAAATC AATCTAAAGT ATATATGAGT AAACTTGGTC TGACAGTTAC CAATGCTTAA TCAGTGAGGC
6651  ACCTATCTCA GCGATCTGTC TATTTCGTTC ATCCATAGTT GCCTGACTCC GGGGGGGGGG GGCGCTGAGG
6721  TCTGCCTCGT GAAGAAGGTG TTGCTGACTC ATACCAGGCC TGAATCGCCC CATCATCCAG CCAGAAAGTG
6791  AGGGAGCCAC GGTTGATGAG AGCTTTGTTG TAGGTGGACC AGTTGGTGAT TTTGAACTTT TGCTTTGCCA
6861  CGGAACGGTC TGCGTTGTCG GAAGATGCG TGATCTGATC CTTCAACTCA GCAAAAGTTC GATTTATTCA
6931  ACAAAGCCGC CGTCCCGTCA AGTCAGCGTA ATGCTCTGCC AGTGTTACAA CCAATTAACC AATTCTGATT
7001  AGAAAAACTC ATCGAGCATC AAATGAAACT CATCTTTATT CATCAGGA TTATCAATAC CATATTTTTG
  271 ◀PhePheGlu AspLeuMetL euHisPheGl nLeuLysAsn MetAspProA snAspIleGl yTyrLysGln
7071  AAAAAGCCGT TTCTGTAATG AAGGAGAAAA CTCACCGAGG CAGTTCCATA GGATGGCAAG ATCCTGGTAT
  248 ◀PheLeuArgL ysGlnLeuSe rProSerPhe GluGlyLeuC ysAsnTrpLe uIleAlaLeu AspGlnTyrA
7141  CGGTCTGCGA TTCGACTCG TCCAACATCA ATACAACCTA TTAATTTCCC CTCGTCAAAA ATAAGGTTAT
  224 ◀rgAspAlaIl eGlyValArg GlyValAspI leCysGlyIl eLeuLysGly GluAspPheI leLeuAsnAs
7211  CAAGTGAGAA ATCACCATGA GTGACGACTG AATCCGGTGA GAATGGCAAA AGCTTATGCA TTTCTTTCCA
  201 ◀pLeuSerPhe AspGlyHisT hrValValSe rAspProSer PheProLeuL euLysHisMe tGluLysTrp
7281  GACTTGTTCA ACAGGCCAGC CATTACGCTC GTCATCAAAA TCACTCGCAT CAACCAAACC GTTATTCATT
  178 ◀ValGlnGluV alProTrpGl yAsnArgGlu AspAspPheA spSerAlaAs pValLeuGly AsnAsnMetA
7351  CGTGATTGCG CCTGAGCGAG ACGAAATACG CGATCGCTGT TAAAAGGACA ATTACAAACA GGAATCGAAT
  154 ◀rgSerGlnAl aGlnAlaLeu ArgPheValA rgAspSerAs nPheProCys AsnCysValP roIleSerHi
7421  GCAACCGGCG CAGGAACACT GCCAGCGCAT CAACAATATT TCACCTGAA TCAGGATATT CTTCTAATAC
  131 ◀sLeuArgArg LeuPheValA laLeuAlaAs pValLeuSer GluGlySerA spProTyrGl uGluLeuVal
7491  CTGGAATGCT GTTTTCCCGG GGATCGCAGT GGTGAGTAAC CATGCATCAT CAGGAGTACG GATAAAATGC
  108 ◀GlnPheAlaT hrLysGlyPr oIleAlaThr ThrLeuLeuT rpAlaAspAs pProThrArg IlePheHisL
7561  TTGATGGTCG GAAGAGGCAT AAATTCCGTC AGCCAGTTTA GTCTGACCAT CTCATCTGTA ACATCATTGG
   84 ◀ysIleThrPr oLeuProMet PheGluThrL euTrpProAsnLe uArgValMet GluAspThrV alAspAsnAl
7631  CAACGCTACC TTTGCCATGT TTCAGAAACA ACTCTGGCGC ATCGGGCTTC CCATACAATC GATAGATTGT
   61 ◀aValSerGly LysGlyHisL ysLeuPheLe uGluProAla AspProLysG lyTyrLeuAr gTyrIleThr
7701  CGCACCTGAT TGCCCGACAT TATCGCGAGC CCATTTATAC CCATATAAAT CAGCATCCAT GTTGGAATTT
   38 ◀AlaGlySerG lnGlyValAs nAspArgAla TrpLysTyrG lyTyrLeuAs pAlaAspMet AsnSerAsnL
7771  AATCGCGGCC TCGAGCAAGA CGTTTCCCGT TGAATATGGC TCATAACACC CCTTGTATTA CTGTTTATGT
   14 ◀euArgProAr gSerCysSer ThrGluArgG lnIleHisSe rMet
7841  AAGCAGACAG TTTTATTGTT CATGATGATA TATTTTTATC TTGTGCAATG TAACATCAGA GATTTTGAGA
7911  CACAACGTGG CTTTCCCCCC CCCCCCATTA TTGAAGCATT TATCAGGGTT ATTGTCTCAT GAGCGGATAC
7981  ATATTTGAAT GTATTTAGAA AAATAAACAA ATAGGGGTTC CGCGCACATT TCCCCGAAAA GTGCCACCTG
8051  ACGTCTAAGA AACCATTATT ATCATGACAT TAACCTATAA AAATAGGCGT ATCACGAGGC CCTTTCGTCT
8121  CGCGCGTTTC GGTGATGACG GTGAAAACCT CTGACACATG CAGCTCCCGG AGACGGTCAC AGCTTGTCTG
8191  TAAGCGGATG CCGGGAGCAG ACAAGCCCGT CAGGGCGCGT CAGCGGGTGT TGGCGGGTGT CGGGGCTGGC
8261  TTAACTATGC GGCATCAGAG CAGATTGTAC GTAGAGTGCA CCATATGCGG TGTGAAATAC CGCACAGATG
8331  CGTAAGGAGA AAATACCGCA TCAGATTGGC TATTGG  (SEQUENCE ID NO: 6)
```

FIG. 9D

```
   1  TGGAAGGGCT AATTTGGTCC CAAAAAAGAC AAGAGATCCT TGATCTGTGG ATCTACCACA CACAAGGCTA

71  CTTCCCTGAT TGGCAGAACT ACACACCAGG GCCAGGGATC AGATATCCAC TGACCTTTGG ATGGTGCTTC

141  AAGTTAGTAC CAGTTGAACC AGAGCAAGTA GAACAGGCCA ATAAGGAGA  GAAGAACAGC TTGTTACACC

211  CTATGAGCCA GCATGGGATG GAGGACCCGG AGGGAGAAGT ATTAGTGTGG AAGTTTGACA GCCTCCTAGC

281  ATTTCGTCAC ATGGCCCGAG AGCTGCATCC GGAGTACTAC AAAGACTGCT GACATCGAGC TTTCTACAAG

351  GGACTTTCCG CTGGGGACTT TCCAGGGAGG TGTGGCCTGG GCGGGACTGG GGAGTGGCGA GCCCTCAGAT

421  GCTACATATA AGCAGCTGCT TTTTGCCTGT ACTGGGTCTC TCTGGTTAGA CCAGATCTGA GCCTGGGAGC
                                                            ──────────────▶
 491  TCTCTGGCTA ACTAGGGAAC CCACTGCTTA AGCCTCAATA AAGCTTGCCT TGAGTGCTCA AAGTAGTGTG

561  TGCCCGTCTG TTGTGTGACT CTGGTAACTA GAGATCCCTC AGACCCTTTT AGTCAGTGTG GAAAATCTCT

631  AGCAGTGGCG CCCGAACAGG GACTTGAAAG CGAAAGTAAA GCCAGAGGAG ATCTCTCGAC GCAGGACTCG
      ───────────────────────────────▶
                BssHII (711)
 701  GCTTGCTGAA GCGCGCAcgg caagaggcga ggggcggcgC ctgACgagGa cgccaaaaat tttgactagc ClaI (830)
 771  ggaggctaga aggagagagC TCGGTGCGAG AGCGTCAGTA TCAAGCGGGG GAGAATTAGA TCGATGGGAA
      ──────────────────────────────────────────────────────────────────────────
 841  AAAATTCGGT TAAGGCCAGG GGGAAAGAAA AAATATAAAT TAAAACATAT AGTATGGGCA AGCAGGGAGC
      ▶
                                                  AccI (959)
 911  TAGAACGATT CGCAGTTAAT CCTGGCCTGT TAGAAACATC AGAAGGCTGT AGACAAATAC TGGGACAGCT 981  ACAACCATCC CTTCAGACAG GATCAGAAGA ACTTAGATCA TTATATAATA CAGTAGCAAC CCTCTATTGT 1051  GTGCATCAAA GGATAGAGAT AAAAGACACC AAGGAAGCTT TAGACAAGAT AGAGGAAGAG CAAAACAAAA
```

FIG. 10A

```
1121  GTAAGAAAAA AGCACAGCAA GCAGCAGCTG ACACAGGACA CAGCAATCAG GTCAGCCAAA ATTACCCTAT

1191  AGTGCAGAAC ATCCAGGGGC AAATGGTACA TCAGGCCATA TCACCTAGAA CTTTAAACGA TAAGCTTGGG
                                                                    ─────────────→
1261  AGTTCCGCGT TACATAACTT ACGGTAAATG GCCCGCCTGG CTGACCGCCC AACGACCCCC GCCCATTGAC

1331  GTCAATAATG ACGTATGTTC CCATAGTAAC GCCAATAGGG ACTTTCCATT GACGTCAATG GGTGGAGTAT

1401  TTACGGTAAA CTGCCCACTT GGCAGTACAT CAAGTGTATC ATATGCCAAG TACGCCCCCT ATTGACGTCA

1471  ATGACGGTAA ATGGCCCGCC TGGCATTATG CCCAGTACAT GACCTTATGG GACTTTCCTA CTTGGCAGTA

1541  CATCTACGTA TTAGTCATCG CTATTACCAT GGTGATGCGG TTTTGGCAGT ACATCAATGG GCGTGGATAG

1611  CGGTTTGACT CACGGGGATT TCCAAGTCTC CACCCCATTG ACGTCAATGG GAGTTTGTTT TGGCACCAAA

1681  ATCAACGGGA CTTTCCAAAA TGTCGTAACA ACTCCGCCCC ATTGACGCAA ATGGGCGGTA GGCGTGTACG

1751  GTGGGAGGTC TATATAAGCA GAGCTCGTTT AGTGAACCGT CAGATCGCCT GGAGACGCCA TCCACGCTGT

1821  TTTGACCTCC ATAGAAGACA CCGACTCTAG AGgatccATC TAAGTAAGCT TGGCATTCCG GTACTGTTGG
                                              ───────────→
1891  TAAAATGGAA GACGCCAAAA ACATAAAGAA AGGCCCGGCG CCATTCTATC CTCTAGAGGA TGGAACCGCT 1961  GGAGAGCAAC TGCATAAGGC TATGAAGAGA TACGCCCTGG TTCCTGGAAC AATTGCTTTT ACAGATGCAC 2031  ATATCGAGGT GAACATCACG TACGCGGAAT ACTTCGAAAT GTCCGTTCGG TTGGCAGAAG CTATGAAACG 2101  ATATGGGCTG AATACAAATC ACAGAATCGT CGTATGCAGT GAAAACTCTC TTCAATTCTT TATGCCGGTG 2171  TTGGGCCCGT TATTTATCGG AGTTGCAGTT GCGCCCGCGA ACGACATTTA TAATGAACGT GAATTGCTCA 2241  ACAGTATGAA CATTTCGCAG CCTACCGTAG TGTTTGTTTC CAAAAAGGGG TTGCAAAAAA TTTTGAACGT 2311  GCAAAAAAAA TTACCAATAA TCCAGAAAAT TATTATCATG GATTCTAAAA CGGATTACCA GGGATTTCAG
```

FIG. 10B

```
2381  TCGATGTACA CGTTCGTCAC ATCTCATCTA CCTCCCGGTT TTAATGAATA CGATTTTGTA CCAGAGTCCT

2451  TTGATCGTGA CAAAACAATT GCACTGATAA TGAATTCCTC TGGATCTACT GGGTTACCTA AGGGTGTGGC

2521  CCTTCCGCAT AGAACTGCCT GCGTCAGATT CTCGCATGCC AGAGATCCTA TTTTTGGCAA TCAAATCATT

2591  CCGGATACTG CGATTTTAAG TGTTGTTCCA TTCCATCACG GTTTTGGAAT GTTACTACA CTCGGATATT

2661  TGATATGTGG ATTTCGAGTC GTCTTAATGT ATAGATTTGA AGAAGAGCTG TTTTTACGAT CCCTTCAGGA

2731  TTACAAAATT CAAAGTGCGT TGCTAGTACC AACCCTATTT TCATTCTTCG CCAAAAGCAC TCTGATTGAC

2801  AAATACGATT TATCTAATTT ACACGAAATT GCTTCTGGGG GCGCACCTCT TTCGAAAGAA GTCGGGGAAG

2871  CGGTTGCAAA ACGCTTCCAT CTTCCAGGGA TACGACAAGG ATATGGGCTC ACTGAGACTA CATCAGCTAT

2941  TCTGATTACA CCCGAGGGGG ATGATAAACC GGGCGCGGTC GGTAAAGTTG TTCCATTTTT TGAAGCGAAG

3011  GTTGTGGATC TGGATACCGG GAAAACGCTG GGCGTTAATC AGAGAGGCGA ATTATGTGTC AGAGGACCTA

3081  TGATTATGTC CGGTTATGTA AACAATCCGG AAGCGACCAA CGCCTTGATT GACAAGGATG GATGGCTACA

3151  TTCTGGAGAC ATAGCTTACT GGGACGAAGA CGAACACTTC TTCATAGTTG ACCGCTTGAA GTCTTTAATT

ClaI (3259)
3221  AAATACAAAG GATATCAGGT GGCCCCCGCT GAATTGGAAT CGATATTGTT ACAACACCCC AACATCTTCG

3291  ACGCGGGCGT GGCAGGTCTT CCCGACGATG ACGCCGGTGA ACTTCCCGCC GCCGTTGTTG TTTTGGAGCA

3361  CGGAAAGACG ATGACGGAAA AAGAGATCGT GGATTACGTC GCCAGTCAAG TAACAACCGC GAAAAAGTTG

3431  CGCGGAGGAG TTGTGTTTGT GGACGAAGTA CCGAAAGGTC TTACCGGAAA ACTCGACGCA AGAAAAATCA

ApaI (3557)
                                                           XhoI (3548)      KpnI(3563)
3501  GAGAGATCCT CATAAAGGCC AAGAAGGGCG GAAAGTCCAA ATTGTAAcTC GAGGGGGGGC CCGGTACCTT
                                                       ──────────▶
```

FIG. 10C

```
3571  TAAGACCAAT GACTTACAAG GCAGCTGTAG ATCTTAGCCA CTTTTTAAAA GAAAAGGGGG GACTGGAAGG
3641  GCTAATTCAC TCCCAAAGAA GACAAGATAT CCTTGATCTG TGGATCTACC ACACACAAGG CTACTTCCCT
3711  GATTGGCAGA ACTACACACC AGGGCCAGGG GTCAGATATC CACTGACCTT TGGATGGTGC TACAAGCTAG
3781  TACCAGTTGA GCCAGATAAG GTAGAAGAGG CCAATAAAGG AGAGAACACC AGCTTGTTAC ACCCTGTGAG
3851  CCTGCATGGA ATGGATGACC CTGAGAGAGA AGTGTTAGAG TGGAGGTTTG ACAGCCGCCT AGCATTTCAT
3921  CACGTGGCCC GAGAGCTGCA TCCGGAGTAC TTCAAGAACT GCTGACATCG AGCTTGCTAC AAGGGACTTT
3991  CCGCTGGGGA CTTTCCAGGG AGGCGTGGCC TGGGCGGGAC TGGGGAGTGG CGAGCCCTCA GATGCTGCAT
4061  ATAAGCAGCT GCTTTTTGCC TGTACTGGGT CTCTCTGGTT AGACCAGATC TGAGCCTGGG AGCTCTCTGG
4131  CTAACTAGGG AACCCACTGC TTAAGCCTCA ATAAAGCTTG CCTTGAGTGC TTCAAGTAGT GTGTGCCCGT
4201  CTGTTGTGTG ACTCTGGTAA CTAGAGATCC CTCAGACCCT TTTAGTCAGT GTGGAAAATC TCTAGCACCC
4271  CCCAGGAGGT AGAGGTTGCA GTGAGCCAAG ATCGCGCCAC TGCATTCCAG CCTGGGCAAG AAAACAAGAC
4341  TGTCTAAAAT AATAATAATA AGTTAAGGGT ATTAAATATA TTTATACATG GAGGTCATAA AAATATATAT
4411  ATTTGGGCTG GGCGCAGTGG CTCACACCTG CGCCCGGCCC TTTGGGAGGC CGAGGCAGGT GGATCACCTG
4481  AGTTTGGGAG TTCCAGACCA GCCTGACCAA CATGGAGAAA CCCCTTCTCT GTGTATTTTT ATGAGATTTT
4551  ATTTTATGTG TATTTTATTC ACAGGTATTT CTGGAAAACT GAAACTGTTT TTCCTCTACT CTGATACCAC
4621  AAGAATCATC AGCACAGAGG AAGACTTCTG TGATCAAATG TGGTGGGAGA GGGAGGTTTT CACCAGCACA
4691  TGAGCAGTCA GTTCTGCCGC AGACTCGGCG GGTGTCCTTC GGTTCAGTTC CAACACCGCC TGCCTGGAGA
4761  GAGGTCAGAC CACAGGGTCA GGGCTCAGTC CCCAAGACAT AAACACCCAA GACATAAACA CCCAACAGGT
4831  CCACCCCGCC TGCTGCCCAG GCAGAGCCGA TTCACCAAGA CGGGAATTAG GATAGAGAAA GAGTAAGTCA
4901  CACAGAGCCG GCTGTGCGGG AGAACGGAGT TCTATTATGA CTCAAATCAG TCTCCCCAAG CATTCGGGGA
4971  TCAGAGTTTT TAAGGATAAC TTAGTGTGTA GGGGGCCAGT GAGTTGGAGA TGAAAGCGTA GGGAGTCGAA
5041  GGTGTCCTTT TGCGCCGAGT CAGTTCCTGG GTGGGGGCCA CAAGATCGGA TGAGCCAGTT TATCAATCCG
5111  GGGGTGCCAG CTGATCCATG GAGTGCAGGG TCTGCAAAAT ATCTCAAGCA CTGATTGATC TTAGGTTTTA
5181  CAATAGTGAT GTTACCCCAG GAACAATTTG GGGAAGGTCA GAATCTTGTA GCCTGTAGCT GCATGACTCC
5251  TAAACCATAA TTTCTTTTTT GTTTTTTTTT TTTTATTTTT GAGACAGGGT CTCACTCTGT CACCTAGGCC
5321  GGAGTGCAGT GGTGCAATCA CAGCTCACTG CAGCCCCTAG AGCGGCCGCC ACCGCGGTGG AGCTCCAATT
5391  CGCCCTATAG TGAGTCGTAT TACAATTCAC TGGCCGTCGT TTTACAACGT CGTGACTGGG AAAACCCTGG
5461  CGTTACCCAA CTTAATCGCC TTGCAGCACA TCCCCCTTTC GCCAGCTGGC GTAATAGCGA AGAGGCCCGC
5531  ACCGATCGCC CTTCCCAACA GTTGCGCAGC CTGAATGGCG AATGGCGCGA AATTGTAAAC GTTAATATTT
5601  TGTTAAAATT CGCGTTAAAT TTTTGTTAAA TCAGCTCATT TTTTAACCAA TAGGCCGAAA TCGGCAAAAT
5671  CCCTTATAAA TCAAAAGAAT AGACCGAGAT AGGGTTGAGT GTTGTTCCAG TTTGGAACAA GAGTCCACTA
5741  TTAAAGAACG TGGACTCCAA CGTCAAAGGG CGAAAAACCG TCTATCAGGG CGATGGCCCA CTACGTGAAC
5811  CATCACCCTA ATCAAGTTTT TTGGGGTCGA GGTGCCGTAA AGCACTAAAT CGGAACCCTA AAGGGACCCC
5881  CCGATTTAGA GCTTGACGGG GAAAGCCGGC GAACGTGGCG AGAAAGGAAG GGAAGAAAGC GAAAGGAGCG
```

FIG. 10D

```
5951  GGCGCTAGGG CGCTGGCAAG TGTAGCGGTC ACGCTGCGCG TAACCACCAC ACCCGCCGCG CTTAATGCGC
6021  CGCTACAGGG CGCGTCCCAG GTGGCACTTT TCGGGGAAAT GTGCGCGGAA CCCCTATTTG TTTATTTTTC
6091  TAAATACATT CAAATATGTA TCCGCTCATG AGACAATAAC CCTGATAAAT GCTTCAATAA TATTGAAAAA
6161  GGAAGAGTAT GAGTATTCAA CATTTCCGTG TCGCCCTTAT TCCCTTTTTT GCGGCATTTT GCCTTCCTGT
6231  TTTTGCTCAC CCAGAAACGC TGGTGAAAGT AAAAGATGCT GAAGATCAGT TGGGTGCACG AGTGGGTTAC
6301  ATCGAACTGG ATCTCAACAG CGGTAAGATC CTTGAGAGTT TTCGCCCCGA AGAACGTTTT CCAATGATGA
6371  GCACTTTTAA AGTTCTGCTA TGTGGCGCGG TATTATCCCG TATTGACGCC GGGCAAGAGC AACTCGGTCG
6441  CCGCATACAC TATTCTCAGA ATGACTTGGT TGAGTACTCA CCAGTCACAG AAAAGCATCT TACGGATGGC
6511  ATGACAGTAA GAGAATTATG CAGTGCTGCC ATAACCATGA GTGATAACAC TGCGGCCAAC TTACTTCTGA
6581  CAACGATCGG AGGACCGAAG GAGCTAACCG CTTTTTTGCA CAACATGGGG GATCATGTAA CTCGCCTTGA
6651  TCGTTGGGAA CCGGAGCTGA ATGAAGCCAT ACCAAACGAC GAGCGTGACA CCACGATGCC TGTAGCAATG
6721  GCAACAACGT TGCGCAAACT ATTAACTGGC GAACTACTTA CTCTAGCTTC CCGGCAACAA TTAATAGACT
6791  GGATGGAGGC GGATAAAGTT GCAGGACCAC TTCTGCGCTC GGCCCTTCCG GCTGGCTGGT TTATTGCTGA
6861  TAAATCTGGA GCCGGTGAGC GTGGGTCTCG CGGTATCATT GCAGCACTGG GGCCAGATGG TAAGCCCTCC
6931  CGTATCGTAG TTATCTACAC GACGGGGAGT CAGGCAACTA TGGATGAACG AAATAGACAG ATCGCTGAGA
7001  TAGGTGCCTC ACTGATTAAG CATTGGTAAC TGTCAGACCA AGTTTACTCA TATATACTTT AGATTGATTT
7071  AAAACTTCAT TTTTAATTTA AAAGGATCTA GGTGAAGATC CTTTTTGATA ACTTCATGAC CAAAATCCCT
7141  TAACGTGAGT TTTCGTTCCA CTGAGCGTCA GACCCCGTAG AAAAGATCAA AGGATCTTCT TGAGATCCTT
7211  TTTTTCTGCG CGTAATCTGC TGCTTGCAAA CAAAAAAACC ACCGCTACCA GCGGTGGTTT GTTTGCCGGA
7281  TCAAGAGCTA CCAACTCTTT TTCCGAAGGT AACTGGCTTC AGCAGAGCGC AGATACCAAA TACTGTCCTT
7351  CTAGTGTAGC CGTAGTTAGG CCACCACTTC AAGAACTCTG TAGCACCGCC TACATACCTC GCTCTGCTAA
7421  TCCTGTTACC AGTGGCTGCT GCCAGTGGCG ATAAGTCGTG TCTTACCGGG TTGGACTCAA GACGATAGTT
7491  ACCGGATAAG GCGCAGCGGT CGGGCTGAAC GGGGGGTTCG TGCACACAGC CCAGCTTGGA GCGAACGACC
7561  TACACCGAAC TGAGATACCT ACAGCGTGAG CTATGAGAAA GCGCCACGCT TCCCGAAGGG AGAAAGGCGG
7631  ACAGGTATCC GGTAAGCGGC AGGGTCGGAA CAGGAGAGCG CACGAGGGAG CTTCCAGGGG GAAACGCCTG
7701  GTATCTTTAT AGTCCTGTCG GGTTTCGCCA CCTCTGACTT GAGCGTCGAT TTTTGTGATG CTCGTCAGGG
7771  GGGCGGAGCC TATGGAAAAA CGCCAGCAAC GCGGCCTTTT TACGGTTCCT GGCCTTTTGC TGGCCTTTTG
7841  CTCACATGTT CTTTCCTGCG TTATCCCCTG ATTCTGTGGA TAACCGTATT ACCGCCTTTG AGTGAGCTGA
7911  TACCGCTCGC CGCAGCCGAA CGACCGAGCG CAGCGAGTCA GTGAGCGAGG AAGCGGAAGA GCGCCCAATA
7981  CGCAAACCGC CTCTCCCCGC GCGTTGGCCG ATTCATTAAT GCAGCTGGCA CGACAGGTTT CCCGACTGGA
8051  AAGCGGGCAG TGAGCGCAAC GCAATTAATG TGAGTTAGCT CACTCATTAG GCACCCCAGG CTTTACACTT
8121  TATGCTTCCG GCTCGTATGT TGTGTGGAAT TGTGAGCGGA TAACAATTTC ACACAGGAAA CAGCTATGAC
8191  CATGATTACG CCAAGCTCGG AATTAACCCT CACTAAAGGT AACAAAAGCT GCTGCAGGGT CCCTAACTGC
8261  CAAGCCCCAC AGTGTGCCCT GAGGCTGCCC CTTCCTTCTA GCGGCTGCCC CCACTCGGCT TTGCTTTCCC
8331  TAGTTTCAGT TACTTGCGTT CAGCCAAGGT CTGAAACTAG GTGCGCACAC AGCGGTAAGA CTGCGAGAGA
8401  AAGAGACCAG CTTTACAGGG GGTTTATCAC AGTGCACCCT GACAGTCGTC AGCCTCACAG GGGGTTTATC
8471  ACATTGCACC CTGACAGTCG TCAGCCTACA AGGGGGTTTA TCACAGTGCA CCCTTACAAT CATTCCATTT
8541  GATTCACAAT TTTTTTAGTC TCTACTGTGC CTAACTTGTA AGTTAAATTT GATCAGAGGT GTGTTCCCAG
8611  AGGGGAAAAC AGTATATACA GGGTTCAGTA CTATCGCATT TCAGGCCTCC ACCTGGGTCT TGGAATGTGT
8681  CCCCCGAGGG GTGATGACTA CCTCAGTTGG ATCTCCACAG GTCACAGTGA CACAAGATAA CCAAGACACC
8751  TCCCAAGGCT ACCACAATGG GCCGCCCTCC ACGTGCACAT GGCCGGAGGA ACTGCCATGT CGGAGGTGCA
8821  AGCACACCTG CGCATCAGAG TCCTTGGTGT GGAGGGAGGG ACCAGCGCAG CTTCCAGCCA TCCACCTGAT
8891  GAACAGAACC TAGGGAAAGC CCCAGTTCTA CTTACACCAG GAAAGGC  (SEQUENCE ID NO: 8)
```

FIG. 10E

| | |
|---|---|
| 1 | TGGAAGGGCT AATTTGGTCC CAAAAAAGAC AAGAGATCCT TGATCTGTGG ATCTACCACA CACAAGGCTA |
| 71 | CTTCCCTGAT TGGCAGAACT ACACACCAGG GCCAGGGATC AGATATCCAC TGACCTTTGG ATGGTGCTTC |
| 141 | AAGTTAGTAC CAGTTGAACC AGAGCAAGTA GAAGAGGCCA AATAAGGAGA GAAGAACAGC TTGTTACACC |
| 211 | CTATGAGCCA GCATGGGATG GAGGACCCGG AGGGAGAAGT ATTAGTGTGG AAGTTTGACA GCCTCCTAGC |
| 281 | ATTTCGTCAC ATGGCCCGAG AGCTGCATCC GGAGTACTAC AAAGACTGCT GACATCGAGC TTTCTACAAG |
| 351 | GGACTTTCCG CTGGGGACTT TCCAGGGAGG TGTGGCCTGG GCGGGACTGG GGAGTGGCGA GCCCTCAGAT |
| 421 | GCTACATATA AGCAGCTGCT TTTTGCCTGT ACTGGGTCTC TCTGGTTAGA CCAGATCTGA GCCTGGGAGC |
| 491 | TCTCTGGCTA ACTAGGGAAC CCACTGCTTA AGCCTCAATA AAGCTTGCCT TGAGTGCTCA AAGTAGTGTG |
| 561 | TGCCCGTCTG TTGTGTGACT CTGGTAACTA GAGATCCCTC AGACCCTTTT AGTCAGTGTG GAAAATCTCT |
| 631 | AGCAGTGGCG CCCGAACAGG GACTTGAAAG CGAAAGTAAA GCCAGAGGAG ATCTCTCGAC GCAGGACTCG |
| 701 | GCTTGCTGAA GCGCGCacgg caagaggcga ggggcggcgC ctgACgagGa cgccaaaaat tttgactagc |
| 771 | ggaggctaga aggagagagC TCGGTGCGAG AGCGTCAGTA TTAAGCGGGG GAGAATTAGA TCGATGGGAA |
| 841 | AAAATTCGGT TAAGGCCAGG GGGAAAGAAG AAGTACAAGC TAAAGCACAT CGTATGGGCA AGCAGGGAGC |
| 911 | TAGAACGATT CGCAGTTAAT CCTGGCCTGT TAGAAACATC AGAAGGCTGT AGACAAATAC TGGGACAGCT |
| 981 | ACAACCATCC CTTCAGACAG GATCAGAGGA GCTTCGATCA CTATACAACA CAGTAGCAAC CCTCTATTGT |
| 1051 | GTGCACCAGC GGATCGAGAT CAAGGACACC AAGGAAGCTT TAGACAAGAT AGAGGAAGAG CAAAACAAGT |
| 1121 | CCAAGAAGAA GGCCCAGCAG CAGCAGCTG ACACAGGACA CAGCAATCAG GTCAGCCAAA ATTACCCTAT |

Annotations on line 701: BssHII (711)
Annotations on line 771: ClaI (830)
Annotations on line 911: AccI (959)

FIG. 11A

```
1191  AGTGCAGAAC ATCCAGGGGC AAATGGTACA TCAGGCCATA TCACCTAGAA CTTTAAACGA TAAGCTTGGG
      ─────────────────────────────────────────────────────────────────────────▶
1261  AGTTCCGCGT TACATAACTT ACGGTAAATG GCCCGCCTGG CTGACCGCCC AACGACCCCC GCCCATTGAC

1331  GTCAATAATG ACGTATGTTC CCATAGTAAC GCCAATAGGG ACTTTCCATT GACGTCAATG GGTGGAGTAT

1401  TTACGGTAAA CTGCCCACTT GGCAGTACAT CAAGTGTATC ATATGCCAAG TACGCCCCCT ATTGACGTCA

1471  ATGACGGTAA ATGGCCCGCC TGGCATTATG CCCAGTACAT GACCTTATGG GACTTTCCTA CTTGGCAGTA

1541  CATCTACGTA TTAGTCATCG CTATTACCAT GGTGATGCGG TTTTGGCAGT ACATCAATGG GCGTGGATAG

1611  CGGTTTGACT CACGGGGATT TCCAAGTCTC CACCCCATTG ACGTCAATGG GAGTTTGTTT TGGCACCAAA

1681  ATCAACGGGA CTTTCCAAAA TGTCGTAACA ACTCCGCCCC ATTGACGCAA ATGGGCGGTA GGCGTGTACG

1751  GTGGGAGGTC TATATAAGCA GAGCTCGTTT AGTGAACCGT CAGATCGCCT GGAGACGCCA TCCACGCTGT

1821  TTTGACCTCC ATAGAAGACA CCGACTCTAG AGgatccATC TAAGTAAGCT TGGCATTCCG GTACTGTTGG
      ─────────────────────────────────────────────────────────────────────────▶
1891  TAAAATGGAA GACGCCAAAA ACATAAAGAA AGGCCCGGCG CCATTCTATC CTCTAGAGGA TGGAACCGCT 1961  GGAGAGCAAC TGCATAAGGC TATGAAGAGA TACGCCCTGG TTCCTGGAAC AATTGCTTTT ACAGATGCAC 2031  ATATCGAGGT GAACATCACG TACGCGGAAT ACTTCGAAAT GTCCGTTCGG TTGGCAGAAG CTATGAAACG 2101  ATATGGGCTG AATACAAATC ACAGAATCGT CGTATGCAGT GAAAACTCTC TTCAATTCTT TATGCCGGTG 2171  TTGGGCGCGT TATTTATCGG AGTTGCAGTT GCGCCCGCGA ACGACATTTA TAATGAACGT GAATTGCTCA 2241  ACAGTATGAA CATTTCGCAG CCTACCGTAG TGTTTGTTTC CAAAAAGGGG TTGCAAAAAA TTTTGAACGT 2311  GCAAAAAAAA TTACCAATAA TCCAGAAAAT TATTATCATG GATTCTAAAA CGGATTACCA GGGATTTCAG 2381  TCGATGTACA CGTTCGTCAC ATCTCATCTA CCTCCCGGTT TTAATGAATA CGATTTTGTA CCAGAGTCCT
```

FIG. 11B

```
2451  TTGATCGTGA CAAAACAATT GCACTGATAA TGAATTCCTC TGGATCTACT GGGTTACCTA AGGGTGTGGC

2521  CCTTCCGCAT AGAACTGCCT GCGTCAGATT CTCGCATGCC AGAGATCCTA TTTTTGGCAA TCAAATCATT

2591  CCGGATACTG CGATTTTAAG TGTTGTTCCA TTCCATCACG GTTTTGGAAT GTTTACTACA CTCGGATATT

2661  TGATATGTGG ATTTCGAGTC GTCTTAATGT ATAGATTTGA AGAAGAGCTG TTTTTACGAT CCCTTCAGGA

2731  TTACAAAATT CAAAGTGCGT TGCTAGTACC AACCCTATTT TCATTCTTCG CCAAAAGCAC TCTGATTGAC

2801  AAATACGATT TATCTAATTT ACACGAAATT GCTTCTGGGG GCGCACCTCT TTCGAAAGAA GTCGGGGAAG

2871  CGGTTGCAAA ACGCTTCCAT CTTCCAGGGA TACGACAAGG ATATGGGCTC ACTGAGACTA CATCAGCTAT

2941  TCTGATTACA CCCGAGGGGG ATGATAAACC GGGCGCGGTC GGTAAAGTTG TTCCATTTTT TGAAGCGAAG

3011  GTTGTGGATC TGGATACCGG GAAAACGCTG GCGTTAATC AGAGAGGCGA ATTATGTGTC AGAGGACCTA

3081  TGATTATGTC CGGTTATGTA AACAATCCGG AAGCGACCAA CGCCTTGATT GACAAGGATG GATGGCTACA

3151  TTCTGGAGAC ATAGCTTACT GGGACGAAGA CGAACACTTC TTCATAGTTA CCGCTTGAA GTCTTTAATT
                                                                    ClaI (3259)
3221  AAATACAAAG GATATCAGGT GGCCCCCGCT GAATTGGAAT CGATATTGTT ACAACACCCC AACATCTTCG

3291  ACGCGGGCGT GGCAGGTCTT CCCGACGATG ACGCCGGTGA ACTTCCCGCC GCCGTTGTTG TTTTGGAGCA

3361  CGGAAAGACG ATGACGGAAA AAGAGATCGT GGATTACGTC GCCAGTCAAG TAACAACCGC GAAAAGTTG

3431  CGCGGAGGAG TTGTGTTTGT GGACGAAGTA CCGAAAGGTC TTACCGGAAA ACTCGACGCA AGAAAAATCA
                                                                    ApaI (3557)
                                                          XhoI (3548)     KpnI(3563)
3501  GAGAGATCCT CATAAAGGCC AAGAAGGGCG GAAAGTCCAA ATTGTAAcTC GAGGGGGGGC CCGGTACCTT

3571  TAAGACCAAT GACTTACAAG GCAGCTGTAG ATCTTAGCCA CTTTTTAAAA GAAAAGGGGG GACTGGAAGG
```

FIG. 11C

```
3641  GCTAATTCAC TCCCAAAGAA GACAAGATAT CCTTGATCTG TGGATCTACC ACACACAAGG CTACTTCCCT

3711  GATTGGCAGA ACTACACACC AGGGCCAGGG GTCAGATATC CACTGACCTT TGGATGGTGC TACAAGCTAG

3781  TACCAGTTGA GCCAGATAAG GTAGAAGAGG CCAATAAAGG AGAGAACACC AGCTTGTTAC ACCCTGTGAG

3851  CCTGCATGGA ATGGATGACC CTGAGAGAGA AGTGTTAGAG TGGAGGTTTG ACAGCCGCCT AGCATTTCAT

3921  CACGTGGCCC GAGAGCTGCA TCCGGAGTAC TTCAAGAACT GCTGACATCG AGCTTGCTAC AAGGGACTTT

3991  CCGCTGGGGA CTTTCCAGGG AGGCGTGGCC TGGGCGGGAC TGGGGAGTGG CGAGCCCTCA GATGCTGCAT

4061  ATAAGCAGCT GCTTTTTGCC TGTACTGGGT CTCTCTGGTT AGACCAGATC TGAGCCTGGG AGCTCTCTGG
                                                ──────────▶

4131  CTAACTAGGG AACCCACTGC TTAAGCCTCA ATAAAGCTTG CCTTGAGTGC TTCAAGTAGT GTGTGCCCGT
      ──────────────────────────────▶

4201  CTGTTGTGTG ACTCTGGTAA CTAGAGATCC CTCAGACCCT TTTAGTCAGT GTGGAAAATC TCTAGCACCC
      ──────────────────────────────▶
4271  CCCAGGAGGT AGAGGTTGCA GTGAGCCAAG ATCGCGCCAC TGCATTCCAG CCTGGGCAAG AAAACAAGAC
4341  TGTCTAAAAT AATAATAATA AGTTAAGGGT ATTAAATATA TTTATACATG GAGGTCATAA AAATATATAT
4411  ATTTGGGCTG GGCGCAGTGG CTCACACCTG CGCCCGGCCC TTTGGGAGGC CGAGGCAGGT GGATCACCTG
4481  AGTTTGGGAG TTCCAGACCA GCCTGACCAA CATGGAGAAA CCCCTTCTCT GTGTATTTTT AGTAGATTTT
4551  ATTTATGTG TATTTTATTC ACAGGTATTT CTGGAAAACT GAAACTGTTT TTCCTCTACT CTGATACCAC
4621  AAGAATCATC AGCACAGAGG AAGACTTCTG TGATCAAATG TGGTGGGAGA GGGAGGTTTT CACCAGCACA
4691  TGAGCAGTCA GTTCGCCGC AGACTCGGCG GGTGTCCTTC GGTTCAGTTC CAACACCGCC TGCCTGGAGA
4761  GAGGTCAGAC CACAGGGTGA GGGCTCAGTC CCCAAGACAT AAACACCCAA GACATAAACA CCCAACAGGT
4831  CCACCCCGCC TGCTGCCCAG GCAGAGCCGA TTCACCAAGA CGGGAATTAG GATAGAGAAA GAGTAAGTCA
4901  CACAGAGCCG GCTGTGCGGG AGAACGGAGT TCTATTATGA CTCAAATCAG TCTCCCCAAG CATTCGGGGA
4971  TCAGAGTTTT TAAGGATAAC TTAGTGTGTA GGGGGCCAGT GAGTTGGAGA TGAAAGCGTA GGGAGTCGAA
5041  GCTGTCCTTT TGCGCCGAGT CAGTTCCTGG GTGGGGGCCA CAAGATCGGA TGAGCCAGTT TATCAATCCG
5111  GGGGTGCCAG CTGATCCATG GAGTGCAGGG TCTGCAAAAT ATCTCAAGCA CTGATTGATC TTAGGTTTTA
5181  CAATAGTGAT GTTACCCCAG GAACAATTTG GGGAAGGTCA GAATCTTGTA GCCTGTAGCT GCATGACTCC
5251  TAAACCATAA TTTCTTTTTT GTTTTTTTT TTTATTTTT GAGACAGGGT CTCACTCTGT CACCTAGGCT
5321  GGAGTGCAGT GGTGCAATCA CAGCTCACTG CAGCCCCTAG AGCGGCCGCC ACCGCGGTGG AGCTCCAATT
5391  CGCCCTATAG TGAGTCGTAT TACAATTCAC TGGCCGTCGT TTTACAACGT CGTGACTGGG AAAACCCTGG
5461  CGTTACCCAA CTTAATCGCC TTGCAGCACA TCCCCCTTTC GCCAGCTGGC GTAATAGCGA AGAGGCCCGC
5531  ACCGATCGCC CTTCCCAACA GTTGCGCAGC CTGAATGGCG AATGGCGCGA AATTGTAAAC GTTAATATTT
5601  TGTTAAAATT CGCGTTAAAT TTTTGTTAAA TCAGCTCATT TTTTAACCAA TAGGCCGAAA TCGGCAAAAT
5671  CCCTTATAAA TCAAAAGAAT AGACCGAGAT AGGGTTGAGT GTTGTTCCAG TTTGGAACAA GAGTCCACTA
5741  TTAAAGAACG TGGACTCCAA CGTCAAAGGG CGAAAAACCG TCTATCAGGG CGATGGCCCA CTACGTGAAC
5811  CATCACCCTA ATCAAGTTTT TTGGGGTCGA GGTGCCGTAA AGCACTAAAT CGGAACCCTA AAGGGAGCCC
5881  CCGATTTAGA GCTTGACGGG GAAAGCCGGC GAACGTGGCG AGAAAGGAAG GGAAGAAAGC GAAAGGAGCG
5951  GGCGCTAGGG CGCTGGCAAG TGTAGCGGTC ACGCTGCGCG TAACCACCAC ACCCGCCGCG CTTAATGCGC
6021  CGCTACAGGG CGCGTCCCAG GTGCACTTT TCGGGGAAAT GTGCGCGGAA CCCCTATTTG TTTATTTTTC
6091  TAAATACATT CAAATATGTA TCCGCTCATG AGACAATAAC CCTGATAAAT GCTTCAATAA TATTGAAAAA
```

FIG. 11D

```
6161  GGAAGAGTAT GAGTATTCAA CATTTCCGTG TCGCCCTTAT TCCCTTTTTT GCGGCATTTT GCCTTCCTGT
6231  TTTTGCTCAC CCAGAAACGC TGGTGAAAGT AAAAGATGCT GAAGATCAGT TGGGTGCACG AGTGGGTTAC
6301  ATCGAACTGG ATCTCAACAG CGGTAAGATC CTTGAGAGTT TTCGCCCCGA AGAACGTTTT CCAATGATGA
6371  GCACTTTTAA AGTTCTGCTA TGTGGCGCGG TATTATCCCG TATTGACGCC GGGCAAGAGC AACTCGGTCG
6441  CCGCATACAC TATTCTCAGA ATGACTTGGT TGAGTACTCA CCAGTCACAG AAAAGCATCT TACGGATGGC
6511  ATGACAGTAA GAGAATTATG CAGTGCTGCC ATAACCATGA GTGATAACAC TGCGGCCAAC TTACTTCTGA
6581  CAACGATCGG AGGACCGAAG GAGCTAACCG CTTTTTTGCA CAACATGGGG GATCATGTAA CTCGCCTTGA
6651  TCGTTGGGAA CCGGAGCTGA ATGAAGCCAT ACCAAACGAC GAGCGTGACA CCACGATGCC TGTAGCAATG
6721  GCAACAACGT TGCGCAAACT ATTAACTGGC GAACTACTTA CTCTAGCTTC CCGGCAACAA TTAATAGACT
6791  GGATGGAGGC GGATAAAGTT GCAGGACCAC TTCTGCGCTC GGCCCTTCCG GCTGGCTGGT TTATTGCTGA
6861  TAAATCTGGA GCCGGTGAGC GTGGGTCTCG CGGTATCATT GCAGCACTGG GGCCAGATGG TAAGCCCTCC
6931  CGTATCGTAG TTATCTACAC GACGGGGAGT CAGGCAACTA TGGATGAACG AAATAGACAG ATCGCTGAGA
7001  TAGGTGCCTC ACTGATTAAG CATTGGTAAC TGTCAGACCA AGTTTACTCA TATATACTTT AGATTGATTT
7071  AAAACTTCAT TTTTAATTTA AAAGGATCTA GGTGAAGATC CTTTTTGATA ATCTCATGAC CAAAATCCCT
7141  TAACGTGAGT TTTCGTTCCA CTGAGCGTCA GACCCCGTAG AAAAGATCAA AGGATCTTCT TGAGATCCTT
7211  TTTTTCTGCG CGTAATCTGC TGCTTGCAAA CAAAAAAACC ACCGCTACCA GCGGTGGTTT GTTTGCCGGA
7281  TCAAGAGCTA CCAACTCTTT TTCCGAAGGT AACTGGCTTC AGCAGAGCGC AGATACCAAA TACTGTCCTT
7351  CTAGTGTAGC CGTAGTTAGG CCACCACTTC AAGAACTCTG TAGCACCGCC TACATACCTC GCTCTGCTAA
7421  TCCTGTTACC AGTGGCTGCT GCCAGTGGCG ATAAGTCGTG TCTTACCGGG TTGGACTCAA GACGATAGTT
7491  ACCGGATAAG GCGCAGCGGT CGGGCTGAAC GGGGGGTTCG TGCACACAGC CCAGCTTGGA GCGAACGACC
7561  TACACCGAAC TGAGATACCT ACAGCGTGAG CTATGAGAAA GCGCCACGCT TCCCGAAGGG AGAAAGGCGG
7631  ACAGGTATCC GGTAAGCGGC AGGGTCGGAA CAGGAGAGCG CACGAGGGAG CTTCCAGGGG GAAACGCCTG
7701  GTATCTTTAT AGTCCTGTCG GGTTTCGCCA CCTCTGACTT GAGCGTCGAT TTTTGTGATG CTCGTCAGGG
7771  GGGCGGAGCC TATGGAAAAA CGCCAGCAAC GCGGCCTTTT TACGGTTCCT GGCCTTTTGC TGGCCTTTTG
7841  CTCACATGTT CTTTCCTGCG TTATCCCCTG ATTCTGTGGA TAACCGTATT ACCGCCTTTG AGTGAGCTGA
7911  TACCGCTCGC CGCAGCCGAA CGACCGAGCG CAGCGAGTCA GTGAGCGAGG AAGCGGAAGA GCGCCCAATA
7981  CGCAAACCGC CTCTCCCCGC GCGTTGGCCG ATTCATTAAT GCAGCTGGCA CGACAGGTTT CCCGACTGGA
8051  AAGCGGGCAG TGAGCGCAAC GCAATTAATG TGAGTTAGCT CACTCATTAG GCACCCCAGG CTTTACACTT
8121  TATGCTTCCG GCTCGTATGT TGTGTGGAAT TGTGAGCGGA TAACAATTTC ACACAGGAAA CAGCTATGAC
8191  CATGATTACG CCAAGCTCGG AATTAACCCT CACTAAAGGG AACAAAAGCT GCTGCAGGGT CCCTAACTGC
8261  CAAGCCCCAC AGTGTGCCCT GAGGCTGCCC CTTCCTTCTA GCGGCTGCCC CCACTCGGCT TTGCTTTCCC
8331  TAGTTTCAGT TACTTGCGTT CAGCCAAGGT CTGAAACTAG GTGCCGCACAG AGCGGTAAGA CTGCGAGAGA
8401  AAGAGACCAG CTTTACAGGG GGTTTATCAC AGTGCACCCT GACAGTCGTC AGCCTCACAG GGGGTTTATC
8471  ACATTGCACC CTGACACCGTCG TCAGCCTCAC AGGGGGTTTA TCACAGTGCA CCCTTACAAT CATTCCATTT
8541  GATTCACAAT TTTTTTAGTC TCTACTGTGC CTAACTTGTA AGTTAAATTT GATCAGAGGT GTGTTCCCAG
8611  AGGGGAAAAC AGTATATACA GGGTTCAGTA CTATCGCATT TCAGGCCTCC ACCTGGGTCT TGGAATGTGT
8681  CCCCCGAGGG GTGATGACTA CCTCAGTTGG ATCTCCACAG GTCACAGTGA CACAAGATAA CCAAGACACC
8751  TCCCAAGGCT ACCACAATGG GCCGCCCTCC ACGTGCACAT GGCCGGAGGA ACTGCCATGT CGGAGGTGCA
8821  AGCACACCTG CGCATCAGAG TCCTTGGTGT GGAGGGAGGG ACCAGCGCAG CTTCCAGCCA TCCACCTGAT
8891  GAACAGAACC TAGGGAAAGC CCCAGTTCTA CTTACACCAG GAAAGGC (SEQUENCE ID NO: 9)
```

FIG. 11E

```
mBCwCN frag    ---------- ---------- --------C- --AC---G-- ----------
m2BCwCN frag   ---------- ---------- --------C- ---G---G-- ----------
BC/HXB2        ---------- ---------- ---------- ---------- ----------
BC/NL43        ---------- ---------- ---------- ---------- ----------
#1             .......... .......... .......... .......... ..........
               CGCGCACGGC AAGAGGCGAG GGGCGGCGAC TGGTGAGTAC GCCAAAAATT mBCwCN frag    ---------- ---------- --------C- C--------- ----------
m2BCwCN frag   ---------- ---------- ---------- ---------- ----------
BC/HXB2        -------T-- ---------- ---------- ---------- ----------
BC/NL43        ---------- ---------- ---------- ---------- -----G----
#51            .......... .......... .......... .......... ..........
               TTGACTAGCG GAGGCTAGAA GGAGAGAGAT GGGTGCGAGA GCGTCAGTAT mBCwCN frag    ---------- ---------- ---------- ---------- ----------
m2BCwCN frag   ---------- ---------- ---------- ---------- ----------
BC/HXB2        ---------- ---------- ---------- ---------- ----------
BC/NL43        ---------- ---------- AA-------- ---------- ----------
#101           .......... .......... .......... .......... ..........
               TAAGCGGGGG AGAATTAGAT CG
```

| | |
|---|---|
| mBCwCN frag | SEQUENCE ID NO: 10 |
| m2BCwCn frag | SEQUENCE ID NO: 11 |
| BC/HXB2 | SEQUENCE ID NO: 12 |
| BC/NL43 | SEQUENCE ID NO: 13 |
| Consensus | SEQUENCE ID NO: 14 |

FIG. 12

Plasmid map: pCMVkanR-R-SIVgp160CTE (6978 bp)

Features (clockwise):
- BsrGI (37)
- SnaBI (432)
- SacII (746)
- PstI (1329)
- XcmI (1778)
- PmlI (2134)
- BspMI (2378)
- Eam1105I (2502)
- PpuMI (2979)
- Bsu36I (3208)
- EcoRI (3412)
- BamHI (3418)
- Eco47III (3457)
- BstEII (3673)
- BsaBI (3740)
- SphI (3948)
- KpnI (3976)
- BstXI (4060)
- XmnI (4293)
- StuI (5368)
- SgfI (5992)
- PvuI (5993)
- BsrFI (6036)
- SspI (6067)
- SmaI (6118)
- NruI (6335)
- DraIII (6523)

Labeled regions: kanamycin resistance gene, gp160, gp41, RRE, ENV-stop, SRV-CTE, ALL-STOP, BGH pA

FIG. 16

```
                                          BsrGI (37)
   1  CCTGGCCATTGCATACGTTGTATCCATATCATAATATGTACATTTATATTGGCTCATGTCCAACATTACCGCCATGTTGA
  81  CATTGATTATTGACTAGTTATTAATAGTAATCAATTACGGGGTCATTAGTTCATAGCCCATATATGGAGTTCCGCGTTAC
 161  ATAACTTACGGTAAATGGCCCGCCTGGCTGACCGCCCAACGACCCCCGCCCATTGACGTCAATAATGACGTATGTTCCCA
 241  TAGTAACGCCAATAGGGACTTTCCATTGACGTCAATGGGTGGAGTATTTACGGTAAACTGCCCACTTGGCAGTACATCAA
 321  GTGTATCATATGCCAAGTACGCCCCCTATTGACGTCAATGACGGTAAATGGCCCGCCTGGCATTATGCCCAGTACATGAC
                                          SnaBI (432)
 401  CTTATGGGACTTTCCTACTTGGCAGTACATCTACGTATTAGTCATCGCTATTACCATGGTGATGCGGTTTTGGCAGTACA
 481  TCAATGGGCGTGGATAGCGGTTTGACTCACGGGGATTTCCAAGTCTCCACCCCATTGACGTCAATGGGAGTTTGTTTTGG
 561  CACCAAAATCAACGGGACTTTCCAAAATGTCGTAACAACTCCGCCCCATTGACGCAAATGGGCGGTAGGCGTGTACGGTG
 641  GGAGGTCTATATAAGCAGAGCTCGTTTAGTGAACCGTCAGATCGCCTGGAGACGCCATCCACGCTGTTTTGACCTCCATA
                   SacII (746)
 721  GAAGACACCGGGACCGATCCAGCCTCCGCGGGCCGCGCTAAGTATGGGATGTCTTGGGAATCAGCTGCTTATCGCCATCT

1▶MetGlyCysLeuGlyAsnGlnLeuLeuIleAlaIleL
 801  TGCTTTTAAGTGTCTATGGGATCTATTGTACTCTATATGTCACAGTCTTTTATGGTGTACCAGCTTGGAGGAATGCGACA

13▶euLeuLeuSerValTyrGlyIleTyrCysThrLeuTyrValThrValPheTyrGlyValProAlaTrpArgAsnAlaThr
 881  ATTCCCCTCTTTTGTGCAACCAAGAATAGGGATACTTGGGGAACAACTCAGTGCCTACCAGATAATGGTGATTATTCAGA

40▶IleProLeuPheCysAlaThrLysAsnArgAspThrTrpGlyThrThrGlnCysLeuProAspAsnGlyAspTyrSerGl
 961  AGTGGCCCTTAATGTTACAGAAAGCTTTGATGCCTGGAATAATACAGTCACAGAACAGGCAATAGAGGATGTATGGCAAC

66▶uValAlaLeuAsnValThrGluSerPheAspAlaTrpAsnAsnThrValThrGluGlnAlaIleGluAspValTrpGlnL
1041  TCTTTGAGACCTCAATAAAGCCTTGTGTAAAATTATCCCCATTATGCATTACTATGAGATGCAATAAAAGTGAGACAGAT

93▶euPheGluThrSerIleLysProCysValLysLeuSerProLeuCysIleThrMetArgCysAsnLysSerGluThrAsp
1121  AGATGGGGATTGACAAAATCAATAACAACAACAGCATCAACAACATCAACGACAGCATCAGCAAAAGTAGACATGGTCAA

120▶ArgTrpGlyLeuThrLysSerIleThrThrThrAlaSerThrThrSerThrThrAlaSerAlaLysValAspMetValAs
1201  TGAGACTAGTTCTTGTATAGCCCAGGATAATTGCACAGGCTTGGAACAAGAGCAAATGATAAGCTGTAAATTCAACATGA

146▶nGluThrSerSerCysIleAlaGlnAspAsnCysThrGlyLeuGluGlnGluGlnMetIleSerCysLysPheAsnMetT
                                          PstI (1329)
1281  CAGGGTTAAAAAGAGACAAGAAAAAAGAGTACAATGAAACTTGGTACTCTGCAGATTTGGTATGTGAACAAGGGAATAAC

173▶hrGlyLeuLysArgAspLysLysLysGluTyrAsnGluThrTrpTyrSerAlaAspLeuValCysGluGlnGlyAsnAsn
1361  ACTGGTAATGAAAGTAGATGTTACATGAACCACTGTAACACTTCTGTTATCCAAGAGTCTTGTGACAAACATTATTGGGA

200▶ThrGlyAsnGluSerArgCysTyrMetAsnHisCysAsnThrSerValIleGlnGluSerCysAspLysHisTyrTrpAs
1441  TGCTATTAGATTTAGGTATTGTGCACCTCCAGGTTATGCTTTGCTTAGATGTAATGACACAAATTATTCAGGCTTTATGC

226▶pAlaIleArgPheArgTyrCysAlaProProGlyTyrAlaLeuLeuArgCysAsnAspThrAsnTyrSerGlyPheMetP
1521  CTAAATGTTCTAAGGTGGTGGTCTCTTCATGCACAAGGATGATGGAGACACAGACTTCTACTTGGTTTGGCTTTAATGGA

253▶roLysCysSerLysValValValSerSerCysThrArgMetMetGluThrGlnThrSerThrTrpPheGlyPheAsnGly
1601  ACTAGAGCAGAAAATAGAACTTATATTTACTGGCATGGTAGGGATAATAGGACTATAATTAGTTTAAATAAGTATTATAA

280▶ThrArgAlaGluAsnArgThrTyrIleTyrTrpHisGlyArgAspAsnArgThrIleIleSerLeuAsnLysTyrTyrAs
1681  TCTAACAATGAAATGTAGAAGACCAGGAAATAAGACAGTTTTACCAGTCACCATTATGTCTGGATTGGTTTTCCACTCAC

306▶nLeuThrMetLysCysArgArgProGlyAsnLysThrValLeuProValThrIleMetSerGlyLeuValPheHisSerG
                                                Xcml (1778)
1761  AACCAATCAATGATAGGCCAAAGCAGGCATGGTGTTGGTTTGGAGGAAAATGGAAGGATGCAATAAAAGAGGTGAAGCAG 333▶lnProIleAsnAspArgProLysGlnAlaTrpCysTrpPheGlyIleLysTrpLysAspAlaIleLysGluValLysGln
1841  ACCATTGTCAAACATCCCAGGTATACTGGAACTAACAATACTGATAAAATCAATTTGACGGCTCCTGGAGGAGGAGATCC 360▶ThrIleValLysHisProArgTyrThrGlyThrAsnAsnThrAspLysIleAsnLeuThrAlaProGlyGlyGlyAspPr
1921  GGAAGTTACCTTCATGTGGACAAATTGCAGAGGAGAGTTCCTCTACTGTAAAATGAATTGGTTTCTAAATTGGGTAGAAG 386▶oGluValThrPheMetTrpThrAsnCysArgGlyGluPheLeuTyrCysLysMetAsnTrpPheLeuAsnTrpValGluA
2001  ATAGGAATACAGCTAACCAGAAGCCAAAGGAACAGCATAAAAGGAATTACGTGCCATGTCATATTAGACAAATAATCAAC 413▶spArgAsnThrAlaAsnGlnLysProLysGluGlnHisLysArgAsnTyrValProCysHisIleArgGlnIleIleAsn
```

FIG. 17A

```
                                                                                     PmlI (2134)
2081 ACTTGGCATAAAGTAGGCAAAAATGTTTATTTGCCTCCAAGAGAGGGAGACCTCACGTGTAACTCCACAGTGACCAGTCT

440▶ Thr TrpHisLysVal GlyLysAsnVal TyrLeuProProArgGluGlyAspLeuThr CysAsnSer Thr Val Thr Ser Le
2161 CATAGCAAACATAGATTGGATTGATGGAAACCAAACTAATATCACCATGAGTGCAGAGGTGGCAGAACTGTATCGATTGG

466▶ uIleAlaAsnIleAspTrpIleAspGlyAsnGlnThrAsnIleThrMetSerAlaGluValAlaGluLeuTyrArgLeuG
2241 AATTGGGAGATTATAAATTAGTAGAGATCACTCCAATTGGCTTGGCCCCCACAGATGTGAAGAGGTACACTACTGGTGGC

493▶ luLeuGlyAspTyrLysLeuVal GluIleThr ProIleGlyLeuAlaProThrAspVal LysArgTyrThr Thr GlyGly
                                                            BspMI (2378)
2321 ACCCTCAAGAAATAAAAGAGGGGTCTTTGTGCTAGGGTTCTTGGGTTTTCTCGCAACGGCAGGTTCTGCAATGGGAGCCGC

520▶ Thr Ser ArgAsnLys ArgGlyVal PheVal LeuGlyPheLeuGlyPheLeuAlaThr Ala GlySer AlaMetGlyAlaAl
2401 CAGCCTGACCCTCACGGCACAGTCCCGAACTTTATTGGCTGGGATAGTCCAACAGCAGCAACAGCTGTTGGACGTGGTCA

546▶ aSer LeuThr LeuThr Ala GlnSer ArgThr LeuLeuAlaGlyIleVal GlnGlnGlnGlnLeuLeuAspVal Val L
                     Eam1105I (2502)
2481 AGAGACAACAAGAATTGTTGCGACTGACCGTCTGGGGAACAAAGAACCTCCAGACTAGGGTCACTGCCATCGAGAAGTAC

573▶ ysArgGlnGlnGluLeuLeuArgLeuThr Val TrpGlyThr LysAsnLeuGlnThr ArgVal Thr AlaIleGluLysTyr
2561 TTAAAGGACCAGGCGCAGCTGAATGCTTGGGGATGTGCGTTTAGACAAGTCTGCCACACTACTGTACCATGGCCAAATGC

600▶ LeuLysAspGlnAlaGlnLeuAsnAla TrpGlyCysAlaPheArgGlnVal CysHisThr Thr Val ProTrpProAsnAl
2641 AAGTCTAACACCAAAGTGGAACAATGAGACTTGGCAAGAGTGGGAGCGAAAGGTTGACTTCTTGGAAGAAAATATAACAG

626▶ aSer LeuThr ProLysTrpAsnAsnGluThr TrpGlnGluTrpGluArgLysVal AspPheLeuGluGluAsnIleThr A
2721 CCCTCCTAGAGGAGGCACAAATTCAACAAGAGAAGAACATGTATGAATTACAAAAGTTGAATAGCTGGGATGTGTTTGGC

653▶ laLeuLeuGluValAlaGlnIleGlnGlnGluLysAsnMetTyrGluLeuGlnLysLeuAsnSer TrpAspVal PheGly
2801 AATTGGTTTGACCTTGCTTCTTGGATAAAGTATATACAATATGGAGTTTATATAGTTGTAGGAGTAATACTGTTAAGAAT

680▶ AsnTrpPheAspLeuAlaSer TrpIleLysTyrIleGlnTyrGlyVal TyrIleValVal GlyVal IleLeuArgI l
2881 AGTGATCTATATAGTACAAATGCTAGCTAAGTTAAGGCAGGGGTATAGGCCAGTGTTCTCTTCCCCACCCTCTTATTTCC

706▶ eVal IleTyrIleVal GlnMetLeuAlaLysLeuArgGlnGlyTyrArgProVal PheSer Ser ProProSer TyrPheG
              PpuMI (2979)
2961 AGCAGACCCATATCCAACAGGACCCGGCACTGCCAACCAGAGAAGGCAAAGAAAGAGACGGTGGAGAAGGCGGTGGCAAC

733▶ lnGlnThr HisIleGlnGlnAspProAlaLeuProThr ArgGluGlyLysGluArgAspGlyGlyGluGlyGlyAsn
3041 AGCTCCTGGCCTTGGCAGATAGAATATATCCACTTTCTTATTCGTCAGCTTATTAGACTCTTGACTTGGCTATTCAGTAA

760▶ Ser Ser TrpProTrpGlnIleGluTyrIleHisPheLeuIleArgGlnLeuIleArgLeuLeuThr TrpLeuPheSerAs
3121 CTGTAGGACTTTGCTATCGAGAGTATACCAGATCCTCCAACCAATACTCCAGAGGCTCTCTGCGACCCTACAGAGGATTC

786▶ nCysArgThr LeuLeuSer ArgVal TyrGlnIleLeuGlnProIleLeuGlnArgLeuSer AlaThr LeuGlnArgIleA
              Bsu36I (3208)
3201 GAGAAGTCCTCAGGACTGAACTGACCTACCTACAATATGGGTGGAGCTATTTCCATGAGGCGGTCCAGGCCGTCTGGAGA

813▶ rgGluVal LeuArgThr GluLeuThr TyrLeuGlnTyrGlyTrpSer TyrPheHisGluAlaVal GlnAlaVal TrpArg
3281 TCTGCGACAGAGACTCTTGCGGGCGCGTGGGGAGACTTATGGGAGACTCTTAGGAGAGGTGGAAGATGGATACTCGCAAT

840▶ Ser AlaThr GluThr LeuAlaGlyAlaTrpGlyAspLeuTrpGluThr LeuArgArgGlyGlyArgTrpIleLeuAlaIl
                                                     BamHI (3418)
                                              EcoRI (3412)
3361 CCCCAGGAGGATTAGACAAGGGCTTGAGCTCACTCTCTTGTGAGGGACAGAGAATTCGGATCCactagttctagaCTCGA
                                                             ◀━━━━━
866▶ eProArgArgIleArgGlnGlyLeuGluLeuThr LeuLeu・・・
              Eco47III (3457)
3441 GGGGGGGCCCGGTACGAGCGCTTAGCTAGCTAGAGACCACCTCCCCTGCGAGCTAAGCTGGACAGCCAATGACGGGTAAG 3521 AGAGTGACATTTTTCACTAACCTAAGACAGGAGGGCCGTCAGAGCTACTGCCTAATCCAAAGACGGGTAAAAGTGATAAA
                                                                     BstEII (3673)
3601 AATGTATCACTCCAACCTAAGACAGGCGCAGCTTCCGAGGGATTTGTCGTCTGTTTTATATATATTTAAAAGGGTGACCT
```

FIG. 17B

```
                                                         BsaBI (3740)
3681 GTCCGGAGCCGTGCTGCCCGGATGATGTCTTGGTCTAGACTCGAGGGGGGGCCCGGTACGATCCAGATCTGCTGTGCCTT

3761 CTAGTTGCCAGCCATCTGTTGTTTGCCCCTCCCCGTGCCTTCCTTGACCCTGGAAGGTGCCACTCCCACTGTCCTTTCC

3841 TAATAAAATGAGGAAATTGCATCGCATTGTCTGAGTAGGTGTCATTCTATTCTGGGGGGTGGGGTGGGGCAGCACAGCAA

SphI (3948)              KpnI (3976)
3921 GGGGGAGGATTGGGAAGACAATAGCAGGCATGCTGGGGATGCGGTGGGCTCTATGGGTACCCAGGTGCTGAAGAATTGAC

BstXI (4060)
4001 CCGGTTCCTCCTGGGCCAGAAAGAAGCAGGCACATCCCCTTCTCTGTGACACACCCTGTCCACGCCCCTGGTTCTTAGTT

4081 CCAGCCCCACTCATAGGACACTCATAGCTCAGGAGGGCTCCGCCTTCAATCCCACCCGCTAAAGTACTTGGAGCGGTCTC

4161 TCCCTCCCTCATCAGCCCACCAAACCAAACCTAGCCTCCAAGAGTGGGAAGAAATTAAAGCAAGATAGGCTATTAAGTGC

XmnI (4293)
4241 AGAGGGAGAGAAAATGCCTCCAACATGTGAGGAAGTAATGAGAGAAATCATAGAATTTCTTCCGCTTCCTCGCTCACTGA

4321 CTCGCTGCGCTCGGTCGTTCGGCTGCGGCGAGCGGTATCAGCTCACTCAAAGGCGGTAATACGGTTATCCACAGAATCAG
4401 GGGATAACGCAGGAAAGAACATGTGAGCAAAAGGCCAGCAAAAGGCCAGGAACCGTAAAAAGGCCGCGTTGCTGGCGTTT
4481 TTCCATAGGCTCCGCCCCCCTGACGAGCATCACAAAAATCGACGCTCAAGTCAGAGGTGGCGAAACCCGACAGGACTATA
4561 AAGATACCAGGCGTTTCCCCCTGGAAGCTCCCTCGTGCGCTCTCCTGTTCCGACCCTGCCGCTTACCGGATACCTGTCCG
4641 CCTTTCTCCCTTCGGGAAGCGTGGCGCTTTCTCAATGCTCACGCTGTAGGTATCCAGTTCGGTGTAGGTCGTTCGCTCC
4721 AAGCTGGGCTGTGTGCACGAACCCCCCGTTCAGCCCGACCGCTGCGCCTTATCCGGTAACTATCGTCTTGAGTCCAACCC
4801 GGTAAGACACGACTTATCGCCACTGGCAGCAGCCACTGGTAACAGGATTAGCAGAGCGAGGTATGTAGGCGGTGCTACAG
4881 AGTTCTTGAAGTGGTGGCCTAACTACGGCTACACTAGAAGGACAGTATTTGGTATCTGCGCTCTGCTGAAGCCAGTTACC
4961 TTCGGAAAAAGAGTTGGTAGCTCTTGATCCGGCAAACAAACCACCGCTGGTAGCGGTGGTTTTTTTGTTTGCAAGCAGCA
5041 GATTACGCGCAGAAAAAAAGGATCTCAAGAAGATCCTTTGATCTTTTCTACGGGGTCTGACGCTCAGTGGAACGAAAACT
5121 CACGTTAAGGGATTTTGGTCATGAGATTATCAAAAAGGATCTTCACCTAGATCCTTTTAAATTAAAAATGAAGTTTTAAA
5201 TCAATCTAAAGTATATATGAGTAAACTTGGTCTGACAGTTACCAATGCTTAATCAGTGAGGCACCTATCTCAGCGATCTG
5281 TCTATTTCGTTCATCCATAGTTGCCTGACTCCGGGGGGGGGGGCGCTGAGGTCTGCCTCGTGAAGAAGGTGTTGCTGAC
          StuI (5368)
5361 TCATACCAGGCCTGAATCGCCCCATCATCCAGCCAGAAAGTGAGGGAGCCACGGTTGATGAGAGCTTTGTTGTAGGTGGA
5441 CCAGTTGGTGATTTTGAACTTTTGCTTTGCCACGGAACCGGTCTGCGTTGTCGGGAAGATGCGTGATCTGATCCTTCAACT
5521 CAGCAAAAGTTCGATTTATTCAACAAAGCCGCCGTCCCGTCAAGTCAGCGTAATGCTCTGCCAGTGTTACAACCAATTAA
5601 CCAATTCTGATTAGAAAAACTCATCGAGCATCAAATGAAACTGCAATTTATTCATATCAGGATTATCAATACCATATTTT
                  271◄PhePheGluAspLeuMetLeuHisPheGlnLeuLysAsnMetAspProAsnAspIleGlyTyrLysG
5681 TGAAAAGCCGTTTCTGTAATGAAGGAGAAAACTCACCGAGGCAGTTCCATAGGATGGCAAGATCCTGGTATCGGTCTGC
      248◄lnPheLeuArgLysGlnLeuSerProSerPheGluGlyLeuCysAsnTrpLeuIleAlaLeuAspGlnTyrArgAspAla
5761 GATTCCGACTCGTCCAACATCAATACAACCTATTAATTTCCCCTCGTCAAAAATAAGGTTATCAAGTGAGAAATCACCAT
      222◄IleGlyValArgGlyValAspIleCysGlyIleLeuLeuGlyIleAspPheIleLeuAsnAspLeuSerPheAspGlyHi
5841 GAGTGACGACTGAATCCGGTGAGAATGGCAAAAGCTTATGCATTTCTTTCCAGACTTGTTCAACAGGCCAGCCATTACGC
      195◄sThrValValSerAspProSerPheProLeuLeuLysHisMetGluLysTrpValGlnValProTrpGlyAsnArgG
                                                                          PvuI (5993)
                                                                          SgfI (5992)
5921 TCGTCATCAAAAATCACTCGCATCAACCAAACCGTTATTCATTCGTGATTGCGCCTGAGCGAGACGAAATACGCGATCGCT
      168◄luAspAspPheAspSerAlaAspValLeuGlyAsnAsnMetArgSerGlnAlaGlnAlaLeuArgPheValArgAspSer
                               BsrFI (6036)                        SspI (6067)
6001 GTTAAAAGGACAATTACAAACAGGAATCGAATGCAACCGGCGCAGGAACACTGCCAGCGCATCAACAATATTTTCACCTG
      142◄AsnPheProCysAsnCysValProIleSerHisLeuArgArgLeuPheValAlaLeuAlaAspValIleAsnGluGlySe
                               SmaI (6118)
6081 AATCAGGATATTCTTCTAATACCTGGAATGCTGTTTTCCCGGGGATCGCAGTGGTGAGTAACCATGCATCATCAGGAGTA
      115◄rAspProTyrGluGluLeuValGlnPheAlaThrLysGlyProIleAlaThrThrLeuLeuTrpAlaAspAspProThrA
6161 CGGATAAAATGCTTGATGGTCGGAAGAGGCATAAATTCGTCAGCCAGTTTAGTCTGACCATCTCATCTGTAACATCATT
       88◄rgIlePheHisLysIleThrProLeuProMetPheGluThrLeuTrpAsnLeuArgValMetGluThrValAspAsn
6241 GGCAACGCTACCTTTGCCATGTTTCAGAAACAACTCTGGCGCATCGGGCTTCCCATACAATCGATAGATTGTCGCACCTG
       62◄AlaValSerGlyLysGlyHisLysLeuPheLeuGluProAlaAspProLysGlyTyrLeuArgTyrIleThrAlaGlySe
                NruI (6335)
6321 ATTGCCCGACATTATCGCGAGCCCATTTATACCCATATAAATCAGCATCCATGTTGGAATTTAATCGCGGCCTCGAGCAA
       35◄rGlnGlyValAsnArgAlaThrTrpLysTyrGlyTyrLeuAspAlaAspMetAsnSerAsnLeuArgProArgSerCysS
6401 GACGTTTCCCGTTGAATATGGCTCATAACACCCCTTGTATTACTGTTTATGTAAGCAGACAGTTTTATTGTTCATGATGA
        8◄erThrGluArgGlnIleHisSerMet
                        DraIII (6523)
6481 TATATTTTTATCTTGTGCAATGTAACATCAGAGATTTTGAGACACAACGTGGCTTTCCCCCCCCCCCCATTATTGAAGCA
6561 TTTATCAGGGTTATTGTCTCATGAGCGGATACATATTTGAATGTATTTAGAAAAATAAACAAATAGGGGTTCCGCGCACA
```

FIG. 17C

```
6641 TTTCCCCGAAAAGTGCCACCTGACGTCTAAGAAACCATTATTATCATGACATTAACCTATAAAAATAGGCGTATCACGAG
6721 GCCCTTTCGTCTCGCGCGTTTCGGTGATGACGGTGAAAACCTCTGACACATGCAGCTCCCGGAGACGGTCACAGCTTGTC
6801 TGTAAGCGGATGCCGGGAGCAGACAAGCCCGTCAGGGCGCGTCAGCGGGTGTTGGCGGGTGTCGGGGCTGGCTTAACTAT
6881 GCGGCATCAGAGCAGATTGTACTGAGAGTGCACCATATGCGGTGTGAAATACCGCACAGATGCGTAAGGAGAAAATACCG
6961 CATCAGATTGGCTATTGG
```
(SEQUENCE ID NO: 15)

FIG. 17D

MOLECULAR CLONES WITH MUTATED HIV GAG/POL, SIV GAG AND SIV ENV GENES

This is continuation-in-part of international application No. PCT/US00/34985, filed Dec. 22, 2000 which claims benifit to Provisional application No. 60/173,036, filed Dec. 23, 1999.

I. TECHNICAL FIELD

The invention relates to nucleic acids comprising mutated HIV-1 gag/pol and SIV gag gene sequences which are capable of being expressed independently of any SIV or HIV regulatory factors. The invention also relates to nucleic acids comprising a mutated SIV env gene sequence, which is capable of being expressed independently of any SIV or HIV regulatory factors. The preferred nucleic acids of the invention are capable of producing infectious viral particles.

The invention also relates to vectors, vector systems and host cells comprising the mutated HIV-1 gag, HIV-1 pol, SIV gag and/or SIV env gene sequences. The invention also relates host cells comprising these nucleic acids and/or vectors or vector systems. The invention also relates to the use of these nucleic acids, vectors, vector systems and/or host cells for use in gene therapy or as vaccines.

II. BACKGROUND

Until recently, gene therapy protocols have often relied on vectors derived from retroviruses, such as murine leukemia virus (MLV). These vectors are useful because the genes they transduce are integrated into the genome of the target cells, a desirable feature for long-term expression. However, these retroviral vectors can only transduce dividing cells, which limits their use for in vivo gene transfer in nonproliferating cells, such as hepatocytes, myofibers, hematopoietic stem cells, and neurons.

Lentiviruses are a type of retrovirus that can infect both dividing and nondividing cells. They have proven extremely efficient at providing long-term gene expression (for up to 6 months) in a variety of nondividing cells (such as, neurons and macrophages) in animal models. See, e.g., Amado et al., Science 285:674–676 (July 1999). It has been proposed that the optimal gene transfer system would include a vector based on HIV, or other lentivirus, that can integrate into the genome of nonproliferating cells. Because retroviruses integrate in the genome of the target cells, repeated transduction is unnecessary. Therefore, in contrast to an adenoviral vector capable of in vivo gene delivery, problems linked to the humoral response to injected viral antigens can be avoided. See, e.g., Naldini et al., Science, 272:263–267 (1996), p. 263.

HIV and other lentiviruses have a complex genome that, in addition to the essential structural genes (env, gag, and pol), contains regulatory (tat and rev) and accessory genes (vpr, vif vpu, and nef). HIV has evolved to efficiently infect and express its genes in human cells, and is able to infect nondividing cells such as macrophages because its preintegration complex can traverse the intact membrane of the nucleus in the target cell. This complex contains, in addition to the viral DNA, the enzyme integrase, the product of the vpr gene, and a protein encoded by the gag gene called matrix. The matrix protein enables the preintegration complex to pass into the nucleus to access the host DNA. Lentiviruses cannot efficiently transduce truly quiescent cells (cells in the $G_0$state). However, unlike murine retroviral vectors, in addition to being able to infect dividing cells, HIV-based vectors can achieve effective and sustained transduction and expression of therapeutic genes in nondividing cells, such as hematopoietic stem cells and in terminally differentiated cells such as neurons, retinal photoreceptors, muscle, and liver cells. See, e.g., Amado et al. (July 1999) and Klimatcheva et al., Frontiers in Bioscience 4:d481–496 (June 1999), and the references cited therein.

Although lentiviral vectors can be efficient gene delivery vehicles, there are safety concerns due to their origin. Therefore, the field has turned its attention to the development of vectors and production systems with built-in safety features to prevent the emergence of replication competent lentivirus (RCL). For example, in most laboratory applications, lentiviral vectors are generally created in a transient system in which a cell line is transfected with three separate constructs: a packaging construct, a transfer construct, and an envelope encoding construct. The packaging construct contains the elements necessary for vector packaging (except for env) and the enzymes required to generate vector particles. The transfer construct contains genetic cis-acting sequences necessary for the vector to infect the target cell and for transfer of the therapeutic (or reporter) gene. The lentivirus env gene is generally deleted from the packaging construct and instead the envelope gene of a different virus is supplied in a third vector "the env-coding vector", although the lentiviruses env gene may be used if it is desired that the vector be intended to infect $CD4^+$T cells. A commonly used envelope gene is that encoding the G glycoprotein of the vesicular stomatitis virus (VSV-G), which can infect a wide variety of cells and in addition confers stability to the particle and permits the vector to be concentrated to high titers (see, e.g., Naldini et al., Science 272:263–267 (1996) and Akkina et al. J. Virol. 70:2581 (1996). The use of three separate constructs and the absence of overlapping sequences between them minimizes the possibility of recombination during lentivirus (transfer) vector production. In addition, because no viral proteins are expressed by the lentiviral (transfer) vector itself, they do not trigger an effective immune response against cells expressing vector in animal models (a particular problem with vectors based on adenovirus). See, e.g., Amado et al., Science 285:674–676 (July 1999) and the references cited therein. See also Naldini et al. Science 272:263–267 (1996).

The initial packaging plasmids contained most HIV genes except for env. In an effort to improve safety, subsequent HIV vectors have been produced in which the packaging plasmid is devoid of all accessory genes. This process does not interfere with efficient vector production and significantly increases the safety of the system because potential RCLs lack the accessory genes necessary for efficient replication of HIV in humans. Although these vectors can transduce growth-arrested cell lines and neurons in vivo, they have been reported to not efficiently transduce macrophages. The accessory gene vpr is believed to be necessary for HIV infection of these cells using these HIV vectors. See, Zufferey et al., Nature Biotechnol. 15:871–875 (1997). In contrast, as discussed later herein, the HIV-based lentiviral vectors of the present invention do not need any HIV accessory genes in order to be able to infect human macrophages and the other cells tested.

The requirement of vpr or vif for efficient transduction of liver cells has also been reported. See, e.g., Kafri et al., Nature Genet. 17:314 (1997). These results indicate that the requirement of accessory genes for efficient lentivirus-mediated gene transfer is dependent on the type of cell chosen as target, suggesting that future applications of lentiviral vectors may involve vector constructs with different accessory genes, as needed.

Zufferey et al., (1997) describe an HIV vector system in which the virulence genes, env, vif, vpr, vpu, and nef have been deleted. This multiply attenuated vector conserved the ability to transduce growth-arrested cells and monocyte-derived macrophages in culture, and could efficiently deliver genes in vivo into adult neurons. The packaging plasmids described Zufferey et al. (1 997) and Naldini et al. (1996) encode Rev and Tat, in addition to Gag and Pol.

Lentiviral vectors engineered to become packaged into virions in the absence of the regulatory gene tat have also been described. See, e.g., Kim et al., J. Virol. 72:811–816 (1998) and Miyoshi et al. J. Virol. 72:8150–8157 (1998). In these vectors the tat gene has been removed from the packaging plasmid. Kim et al. state that tat is not necessary as long as the serial 5' LTR promoter is replaced with a strong constitutive promoter. It also has other advantages for HIV therapy. Replacement of the HIV-1 LTR with a constitutive HCMV promoter permits the use of anti-Tat molecules such as Tat transdominant mutants or Tat activation response element decoys as therapeutic agents, since they will not affect vector production. (see p. 814, col. 2). The removal of the tat gene eliminates an essential virulence factor that could contribute to a possible RCL. Kim et al. (1998) describe a vector system which does not contain tat, vf vpr, vpu and nef The preferred vector system includes the rev gene which, the authors state "with RRE, is required for efficient RNA handling in this system." (p. 811, col. 2). However, Kim et al. also constructed Rev independent constructs using CTE. Kim et al. state that the rev/RRE components could be removed by using a sequence such as the Mason-Pfizer monkey virus (MPMV) constitutive transport element (CTE), thereby eliminating all accessory proteins, but this leads to a significant reduction in titer.

Srinivasakumar et al., J. Virol. 71:5841–5848 (1997) describes the generation of stable HIV-1 packaging lines that constitutively express high levels of HIV-1 structural proteins in either a Rev-dependent or a Rev-independent fashion. These cell lines were used to assess gene transfer by using a HIV-1 vector expressing the hygromycin B resistance gene and to study the effects of Rev, Tat, and Nef on the vector titer. The Rev-independent cell lines were created by using gag-pol and env expression vectors that contain the MPMV CTE. This article describes the construction of four plasmids, among others: CMV gagpol-RRE and pCMVenv, which require Rev coexpression for HIV-1 structural gene expression, and pCMV gagpol-CTE and pCMVenv-CTE, which do not. To create Rev-containing and Rev-independent packaging, cell lines, CMT3 cells were transfected with vectors expressing Gag, Gag-Pol, and Env, using a calcium phosphate transfection procedure.

By creating an HIV vector which contained the MPMV CTE (pTR167-CTE) and a packaging cell line which expressed the HIV structural proteins in a Rev-independent fashion, the authors were able to obtain a HIV vector system that functions completely without Rev. The titer of the vector obtained from this system was essentially the same as that obtained from a parallel system which contained Rev. The authors state that, in this context, the CTE seemed to substitute completely for Rev-RRE functions, similar to what was previously observed in transient-expression assays with Rev-dependent constructs. This is in contrast to situations where several rounds of HIV replication were measured. In those cases, titers from CTE-containing viruses were always reduced by at least 1 log unit compared to viruses utilizing Rev and the RRE. (See, Srinivasakumar et al., p. 5847).

The authors state that the advantages of having a HIV vector system that works in the absence of Rev opens the possibility of using it as a delivery vehicle for intracellular immunization against Rev function. Genes encoding Rev antagonists that have dramatic inhibitory effects on HIV replication, such as Rev M10 or RRE decoys, could be introduced into an HIV vector and put into cells normally injectable by HIV. Expression of the "anti-Rev" gene would be expected to dampen HIV infection. Any residual HIV replication should lead to activation of the vector LTR (by Tat) and create a vector-derived RNA that would be packaged by proteins derived from the infectious virus. In this scenario, the wild-type virus would act as a helper that may allow the spread of vector particles to previously nonimmunized cells. Because of the additional vector spread, it is likely that this type of scheme will be more effective in modulating HIV infection in vivo than one based on traditional retrovirus vectors. The authors state that they are currently testing this approach in model systems. (See, Srinivasakumar et al., p. 5847).

Another development in the quest for a safe system is the so-called self-inactivating (SIN) vector. See, e.g., Yu et al., Proc Natl Acad Sci USA 83:3194–8 (1986) and Miyoshi et al., J. Virol. 72:8150 (1998). In Yu et al., a retrovirus-derived vector SIN vector was designed for the transduction of whole genes into mammalian cells. The SIN vector of Yu et al. contains a deletion of 299 base pairs in the 3' long terminal repeat (LTR), which includes sequences encoding the enhancer and promoter functions. When viruses derived from such vectors were used to infect NIH 3 T3 cells, the deletion was transferred to the 5' LTR, resulting in the transcriptional inactivation of the provirus in the infected cell. Introduction of a hybrid gene (human metallothionein-promoted c-fos) into cells via a SIN vector was not associated with rearrangements and led to the formation of an authentic mRNA transcript, which in some cases was induced by cadmium. The vector described in Miyoshi et al. also contains a deletion the 3' (downstream) LTR. A sequence within the upstream LTR serves as a promoter under which the viral genome is expressed. The deletion introduced in the downstream LTR is transferred to the upstream LTR during reverse transcription. This deletion inactivates the LTR promoter and eliminates the production of vector RNA. The gene (or genes) to be transferred (e.g., a reporter or therapeutic gene) is expressed from an exogenous viral or cellular promoter that is inserted into the lentivirus vector. An important safety feature of SIN vectors is that inactivation of the promoter activity of the LTR reduces the possibility of insertional mutagenesis (of the transfer vector) into the host genome. In addition, because the expression of the (transfer) vector RNA is eliminated, the potential for RCL production in the target cell is further minimized. SIN vectors should be particularly useful in gene transfer experiments designed to study the regulated expression of genes in mammalian cells. Absence of enhancer and promoter sequences in both LTRs of the integrated provirus should also minimize the possibility of activating cellular oncogenes and may provide a safer alternative to be used in human gene therapy. Other modifications to enhance safety and specificity include the use of specific internal promoters that regulate gene expression, either temporally or with tissue or cell specificity.

Other strategies to improve safety in human studies would be to use nonhuman lentiviruses such as simian immunodeficiency virus, bovine immunodeficiency virus, or equine infectious anemia virus. Of these, vectors derived from the feline immunodeficiency virus have been engineered to efficiently transduce nondividing human cells. See, e.g., Poeschla et al., Nature Med. 4:354–357 (1998) and WO 99/15641. In addition, White et al., J. Virol. 73:2832–2840 (April 1999) described lentiviral vectors using human and simian immunodeficient virus elements in attempt to improve safety by reducing the likelihood of recombination between packaging constructs and transfer constructs.

The development of efficient packaging lines has proven challenging because expression of the VSV-G envelope and a number of HIV proteins is toxic to cells. Recently, a producer line has been designed in which the expression of packaging genes and VSV-G, and therefore the production of vector, can be turned on at will. Kafri et al., J. Virol. 73–576–584 (1999). The cell line can be expanded for scale-up vector production when the expression of toxic genes is turned off. This cell line produces high titer vector without generating RCL. Hematopoietic stem cells transduced with an HIV vector were transplanted into rhesus macaques as described by Donahue et al. Blood 92 (suppl. 1), abstract 4648.5 (1998) with at least a 14-month follow-up. At that time the procedure proved to be safe; all animals in the study have remained healthy without evidence of circulating HIV or vector. See, Amado et al., Science 285:674–676 (July 1999).

Many gene therapy protocols have been designed to correct a number of inherited metabolic, infectious, or malignant diseases using the hematopoietic stem cell. This cell has the capacity to self-renew and to differentiate into all of the mature cells of the blood and immune systems. Many diseases that affect these systems could potentially be treated by the stable introduction of therapeutic genes into stem cells. Recently, lentiviral vectors were shown to bypass the need for ex vivo stem cell stimulation (which is necessary when using murine retroviral vectors), by mediating efficient gene transfer into very primitive human stem cells that contributed to stable, long-term reconstitution of SCID mouse bone marrow with many hematopoietic lineages. See, e.g., Miyoshi et al., Science 283:682 (1999). Similarly, in a rhesus macaque model of autologous transplantation with lentivirus-transduced stem cells, multilineage gene expression was found, suggesting transduction of an early blood cell progenitor under conditions of minimal stem cell stimulation, ordinarily insufficient for transduction with murine retroviruses. See, Donahue et al., Blood 92 (suppl. 1), abstract 4648.5 (1999) and Amado et al., Science 285:674–676 (July 1999).

In HIV infection, another advantage of lentiviral vectors designed against HIV is their potential to be mobilized by HIV in the infected patient, because the virus supplies all of the necessary elements for packaging of the vector. If these mobilized vectors contained the HIV envelope, they could efficiently transfer their genes (for example, genes custom-designed to confer resistance against HIV) into $CD4^+$ T cells, protecting them from subsequent HIV infection. Lentiviral vectors can also be designed to efficiently express their genes only in $CD4^+$ T cells that are infected with HIV (so called tat-inducible vectors). In these vectors, all HIV genes, including tat and rev, are ablated; cis-acting sequences required for integration, expression, and packaging are retained, and expression is dependent on the activity of the HIV LTR (which requires transactivation by Tat). It has been shown that in this system, vector expression is induced efficiently upon HIV infection. Moreover, in the absence of genes that confer resistance against HIV, stable integration of this vector in permissive cell lines resulted in inhibition of HIV replication. Although the mechanism of HIV inhibition has not been completely elucidated, preliminary results suggest that this vector competes with HIV at the level of reverse transcription. See, An et al., J. Virol., in press, and Amado et al., Science 285:674–676 (1999).

A number of other potential medical applications, where the modification of the genetic material of quiescent cells could result in the prevention or reversal of a disease process, are beginning to be explored. For example, the finding that lentiviral vectors can mediate stable and long-term gene transfer by direct injection of vector into the rat and mouse retina has lent support to the notion of gene therapy for the treatment of retinitis pigmentosa. This degenerative disease of the retina is characterized by photoreceptor cell death, resulting in a slow progression to blindness. Mutations in the CGMP phosphodiesterase $\beta$ subunit (PDE$\beta$) gene of rod photoreceptors lead to an autosomal recessive form of retinitis pigmentosa in humans, and in the rd mouse model of the disease. Previous studies have shown that adenovirus and adeno-associated virus-mediated PDEP subretinal gene transfer results in a delay in photoreceptor cell death. Using the rd mouse model, a recent study demonstrated that photoreceptors could be rescued in up to 50% of eyes injected with a lentivirus vector containing the murine PDE$\beta$ gene. In contrast with the short-term expression previously obtained with adenovirus vectors, PDE$\beta$ expression in this study persisted for at least 24 weeks. This finding points to the potential success of gene therapy in a disease that currently lacks effective treatment. See, Takahashi et al., J. Virol., 73:7812–7816 (September 1999) and Amado et al. Science, 285:674–676 (1999).

In nature, the expression of gag, pol, and env of HIV-1 depends on the presence of the viral Rev protein. This dependence is, at least in part, due to the presence of negatively acting sequences (inhibitory or instability elements [INS]) located within unspliced and partially spliced mRNAs. The positive interaction of Rev with the Rev-responsive element [RME] in these mRNAs counteracts the negative effects of the inhibitory sequences.

None of the above references teach or suggest that the gag and/or pol genes described therein may be replaced with the gag and/or pol genes in which the inhibitory/instability have been mutated to render their expression Rev-idependent. Furthermore, there is no disclosure of the specific HIV-1 gag/pol or SIV gag mutated genes described herein.

The gag/pol clone of the invention was made using the method for eliminating inhibitory/instability regions from a gene as first described in U.S. patent application Ser. No. 07/858,747, filed Mar. 27, 1992 (which issued as U.S. Pat. No. 6,174,666) entitled "Method of Eliminating Inhibitory/Instability Regions from mRNA" and later described in a Continuation-in-Part ("CIP") application, filed as PCT application PCT/US93/02908 on Mar. 29, 1993 and U.S. Pat. Nos. 5,972,596 and 5,965,726. The disclosure of the CIP application was published as International Publication No. WO 93/20212 on Oct. 14, 1993. (The disclosures of these patents and patent applications are specifically incorporated by reference herein in their entirety.) The method was also described in Schwartz et al., J. Virol. 66:7176–7182 (1992).

Schneider et al., J. Virol. 71:4892–4903 (1997), extend the work described in the patent applications and in Schwartz et al. by identifying and characterizing additional INS within gag, protease and pol genes and mutating them in a similar manner. Schneider et al. disclose nucleic acid constructs which contain completely mutated HIV-1 gag genes, but only partially mutated HIV-1 pol genes.

Schneider et al. demonstrate that expression vectors containing an intact or nearly intact $p55^{gag}$ region allow the production of immature viral particles in mammalian cells in the absence of any other HIV proteins. The introduction of additional mutations in the protease region allowed efficient production of Gag/protease, which resulted in processing of the Pr55$^{gag}$ precursor and production of mature Gag particles with a lentivirus-like conical-core structure.

Schneider et al. disclose that Rev-independent expression vectors allow the efficient expression of Gag proteins in many cell lines that are not able to support efficient Rev-RRE-dependent rescue of these RNAs. Schneider et al. also disclose that gag/pol expression vectors may be important for vaccination approaches against HIV-1, since the gag/pol region is more conserved than is the env region and may be important for an effective immune response against HIV and for protection against infection. They also state that efficient HIV gene expression in many cells is also of interest for possible gene transfer experiments using lentiviral vectors in nondividing or slowly dividing cells, since HIV and the other lentiviruses are able to infect quiescent cells.

Pavlakis et al., Natl Conf Hum Retroviruses Relat Infect (2nd). (1995), 91, state that Rev-independent Gag expression vectors were able to produce viral particles in human and mouse cells in the absence of any other HIV proteins, and that additional mutations in the pol region allowed the expression of the protease and the processing of the p55 gag precursor. Direct DNA injection of TAT and Rev independent Gag expression vectors in mouse muscle resulted in Gag expression detected by ELISA and in anti-gag antibody response. Several Rev-and Tat-independent Gag expression cassettes were inserted into retroviral vectors and cell lines expressing Gag or Gag fragments that are dominant negative inhibitors of HIV-1 were constructed.

Shiver et al. (1 996) describe the results of DNA vaccination of mice and non-human primates with mutated plasmid DNA encoding either mutated genes encoding HIV-1 gag (p55 gag) or env (gp120 or gp160). Both gag and env vaccine recipients exhibited antigen-specific cytotoxic and helper T lymphocyte (CTL, Th) responses. The results are stated to demonstrate that DNA vaccines elicited long-lived T cell responses in both mice and nonhuman primates that were disseminated throughout the lymphatics.

III. SUMMARY OF THE INVENTION

The invention relates to nucleic acids comprising the nucleic acid sequence of the mutated HIV-1 gag/pol gene shown in FIG. 1 (SEQUENCE ID NO: 1) and vectors and vector systems comprising these nucleic acids.

The invention also relates to nucleic acids comprising the nucleic acid sequence of the mutated SIV gag gene shown in FIG. 3 and vectors and vector systems comprising these nucleic acids.

The invention also relates to nucleic acids comprising the mutated SIV env gene shown in FIG. 17 and vectors and vector systems comprising these nucleic acids.

The invention also relates to products produced by the nucleic acids, e.g., mRNA, protein, and infectious viral particles.

The invention also relates to compositions comprising these nucleic acids and/or their expression products.

The invention also relates to host cells comprising these nucleic acids, vector systems or viral particles.

The invention also relates to uses of these nucleic acids, vector systems, host cells, expression products, and/or compositions to produce mRNA, proteins, and/or infectious viral particles, and/or to induce antibodies and/or cytotoxic or helper T lymphocytes.

The invention also relates to the use of these nucleic acid constructs, vectors, vector systems and or host cells for use in immunotherapy and immunoprophylaxis, e.g., as a vaccine, or in genetic therapy after expression, preferably in humans. The nucleic acid constructs of the invention can include or be incorporated into lentiviral vectors or other expression vectors or they may also be directly injected into tissue cells resulting in efficient expression of the encoded protein or protein fragment. These constructs may also be used for in-vivo or in-vitro gene replacement, e.g., by homologous recombination with a target gene in-situ.

IV. BRIEF DESCRIPTION OF THE DRAWINGS

FIGS. 1A–1D. DNA sequence of a mutated HIV-1 gag/pol molecular clone (SEQUENCE ID NO: 1). The gagpol terminator is located at positions 4305–4397 of SEQUENCE ID NO: 1.

FIGS. 2A–2F. Comparison of the sequence of the wild—type and mutated poi region in pCMVgagpolBNkan. Position #1 in the figure is position 2641 in plasmid pCMVgagpolBNkan. The comparison starts at position 1872 from the gag initiator ATG.

FIG. 3. DNA sequence of a mutated SIV gag molecular clone (SIVgagDX).

FIGS. 4A–4D. Comparison of the mutated SIV gag DNA sequence in SIVgagDX with the wild type SIV sequence from Simian (macaque) immunodeficiency virus isolate 239, clone lambda siv 239-1 (GenBank accession No. M33262).

FIG. 5. Schematic diagram of some components of sample versions of a lentiviral system. BGH poly (A): bovine growth hormone poly (A) signal; MSD: mutated splice donor site; ψ: encapsidation signal; SD, splice donor site; SA, splice acceptor site; "X" indicates that the ATG codon of the partial gag gene sequence is mutated so that translation of this gene does not occur.

Figure 6:
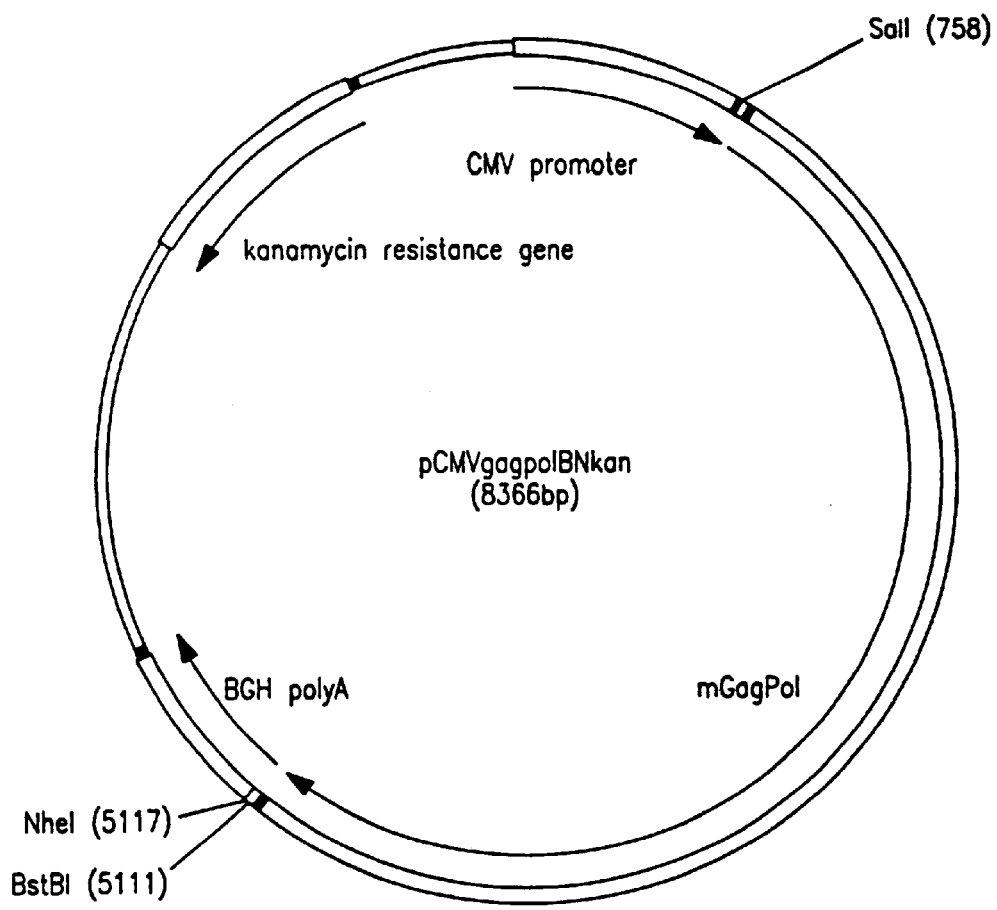

FIG. 6. Schematic diagram of the packaging construct pCMVgagpolBNkan.

Figure 7:
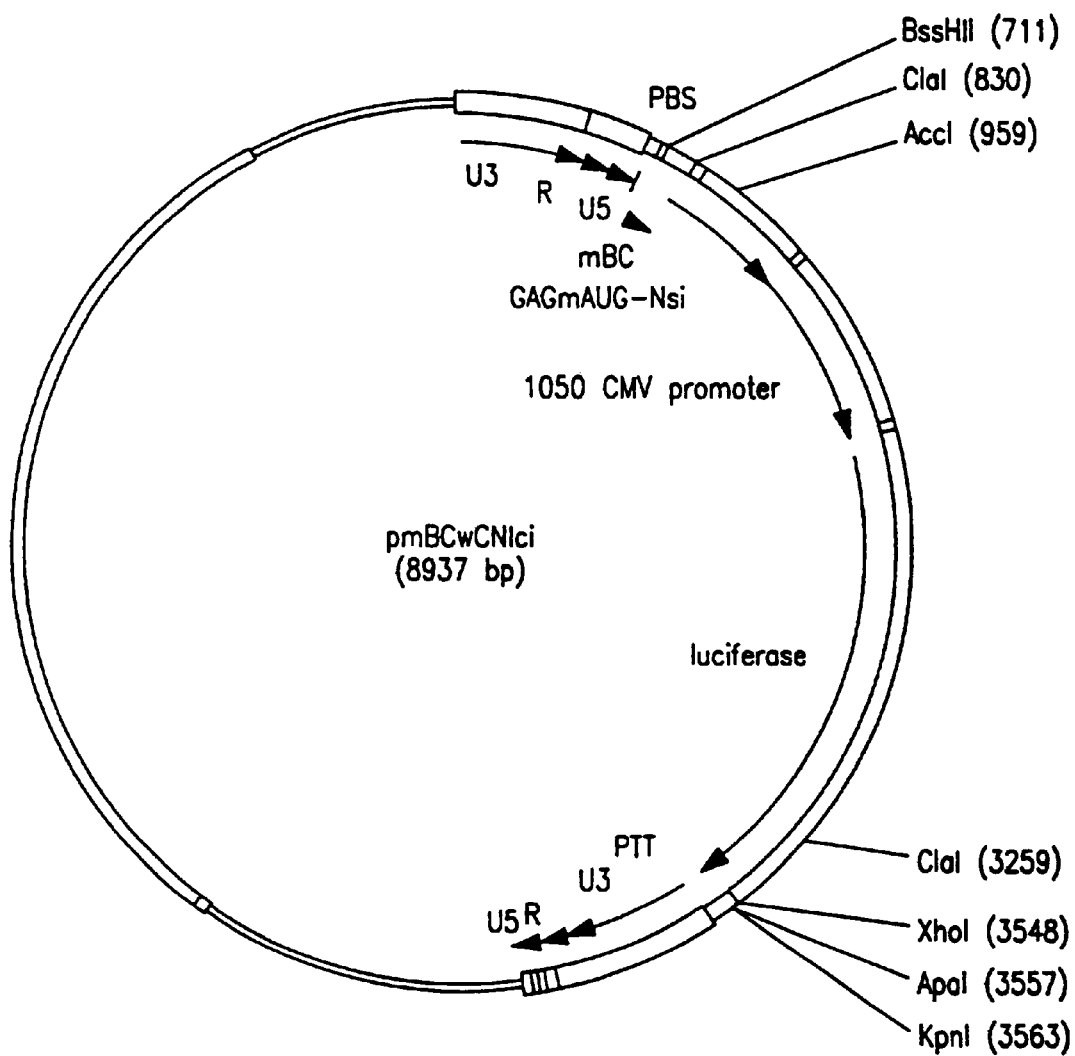

FIG. 7. Schematic diagram of transfer construct 1: pmB-CwCNluci. The packaging signal, the CMV promoter and the coding region for the luciferase gene are flanked by the 5' and 3 HIV-1 LTRs, which provide promoter and polyadenylation signals, as indicated by the arrows. Three consecutive arrows indicate the U5, R, and U3 regions of the LTR, respectively. The transcribed portions of the LTRs are shown in black. Some restriction endonuclease cleavage sites are also indicated.

Figure 8:
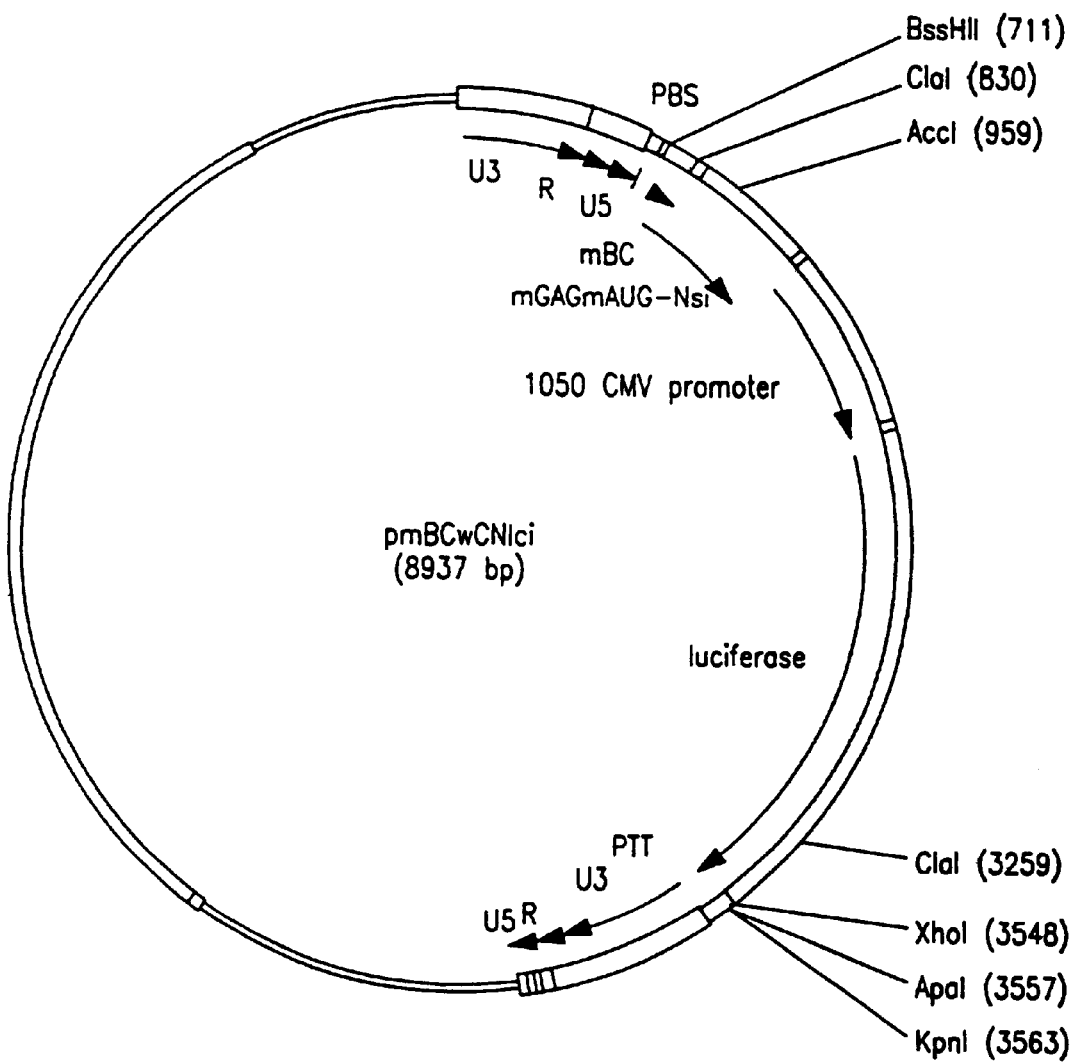

FIG. 8. Schematic diagram of transfer construct 1: pmBCmCNluci. Symbols are as above.

FIGS. 9A–9D. DNA sequence of packaging construct pCMVgagpolBNkan.

FIGS. 10A–10E. DNA sequence of transfer construct 1: pmBCwCNluci.

FIGS. 11A–11E. DNA sequence of transfer construct 1: pmBCmCNluci.

FIG. 12. Nucleotide sequence of the region BssHII (711) to ClaI (830) in wild-type HIV-1 molecular clones HXB2 and NL4-3, and in the transfer constructs. The translation initiator signal for Gag protein (ATG) is underlined. pmB-CwCNluci and pmBCmCNluci (transfer constructs 1 and 2) contain the sequence mBCwCN. Transfer construct 3 contains the sequence m2BCwCN. In contrast to the sequence mBCwCN, m2BCwCN has different mutations at the 5' splice site region and has an intact Gag ATG.

Figure 13:
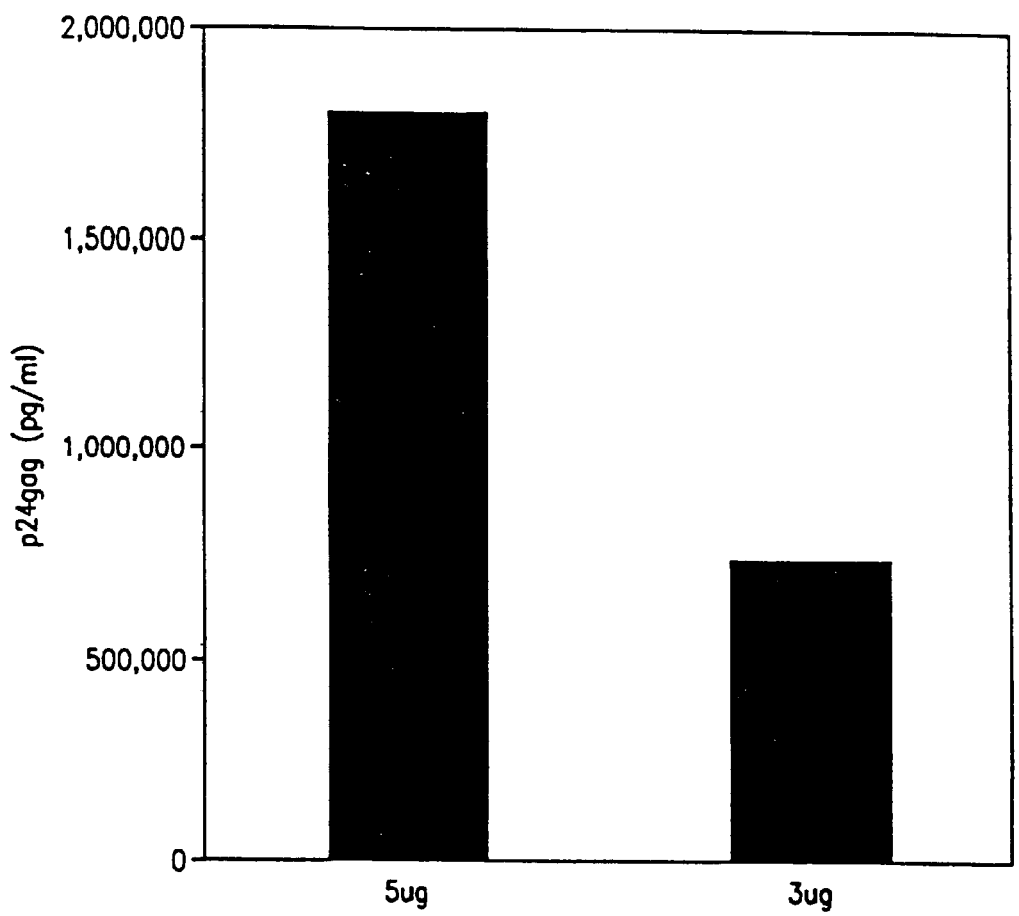

FIG. 13. Bar graph showing levels of gag protein that is released from cells upon transient transfection with pCMVgagpolBNkan (labeled pCMVBNKan in the figure).

Figure 14:
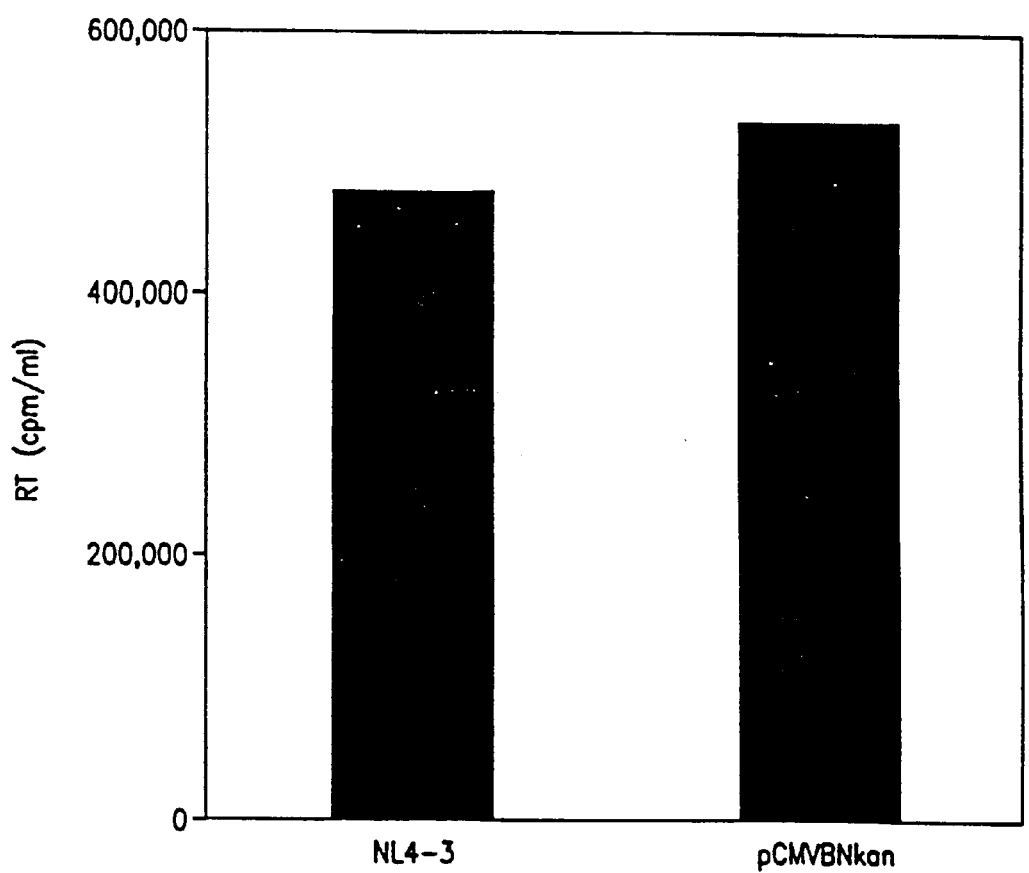
Figure 15A:
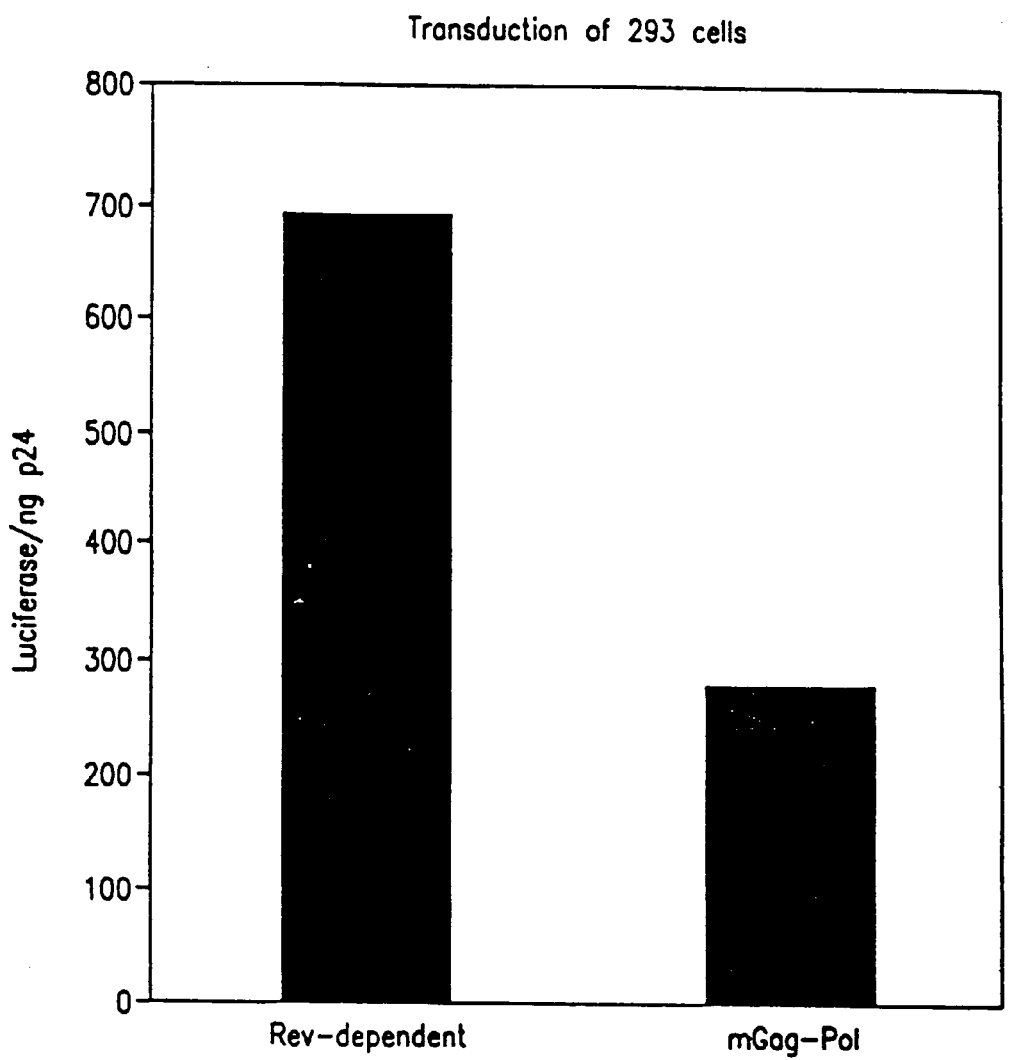
Figure 15B:
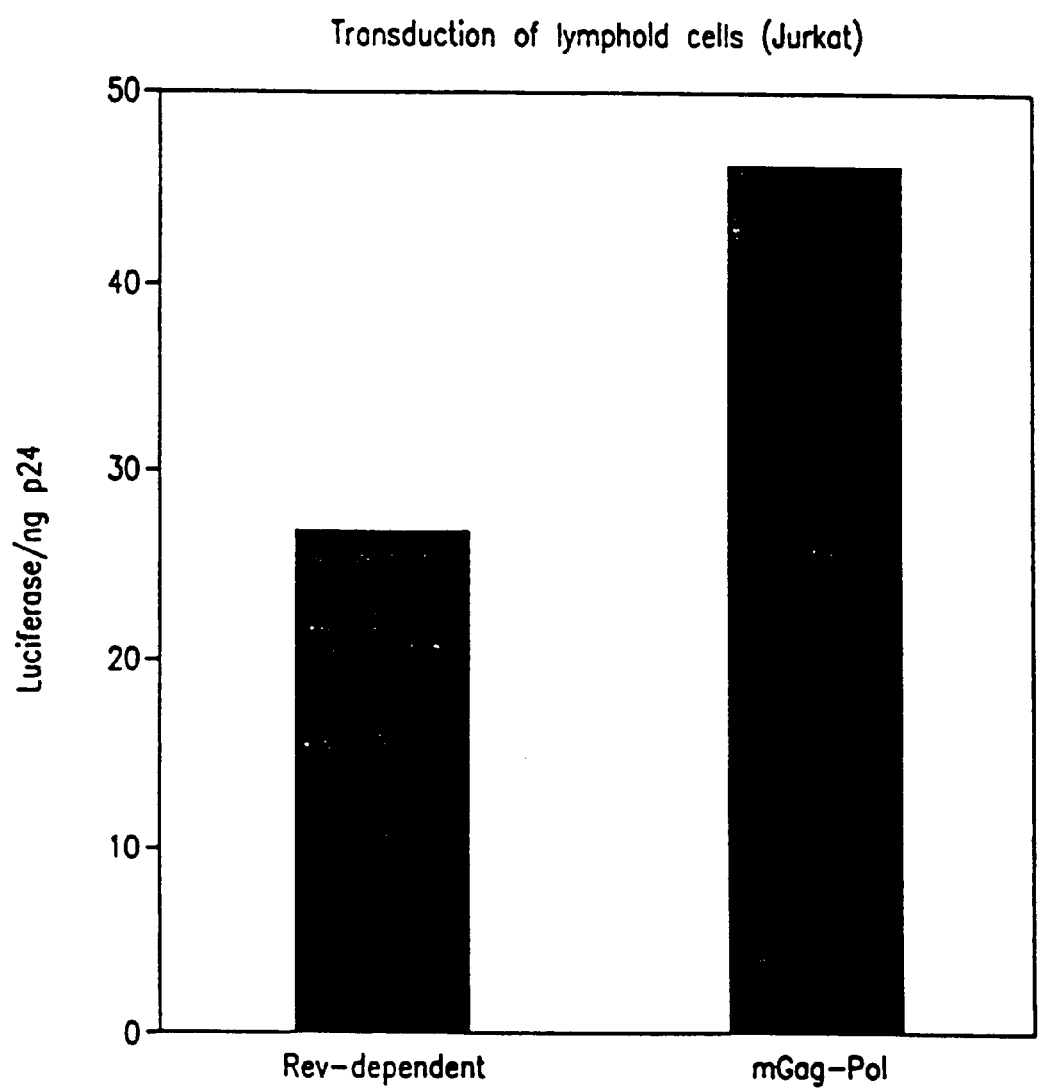
Figure 15C:
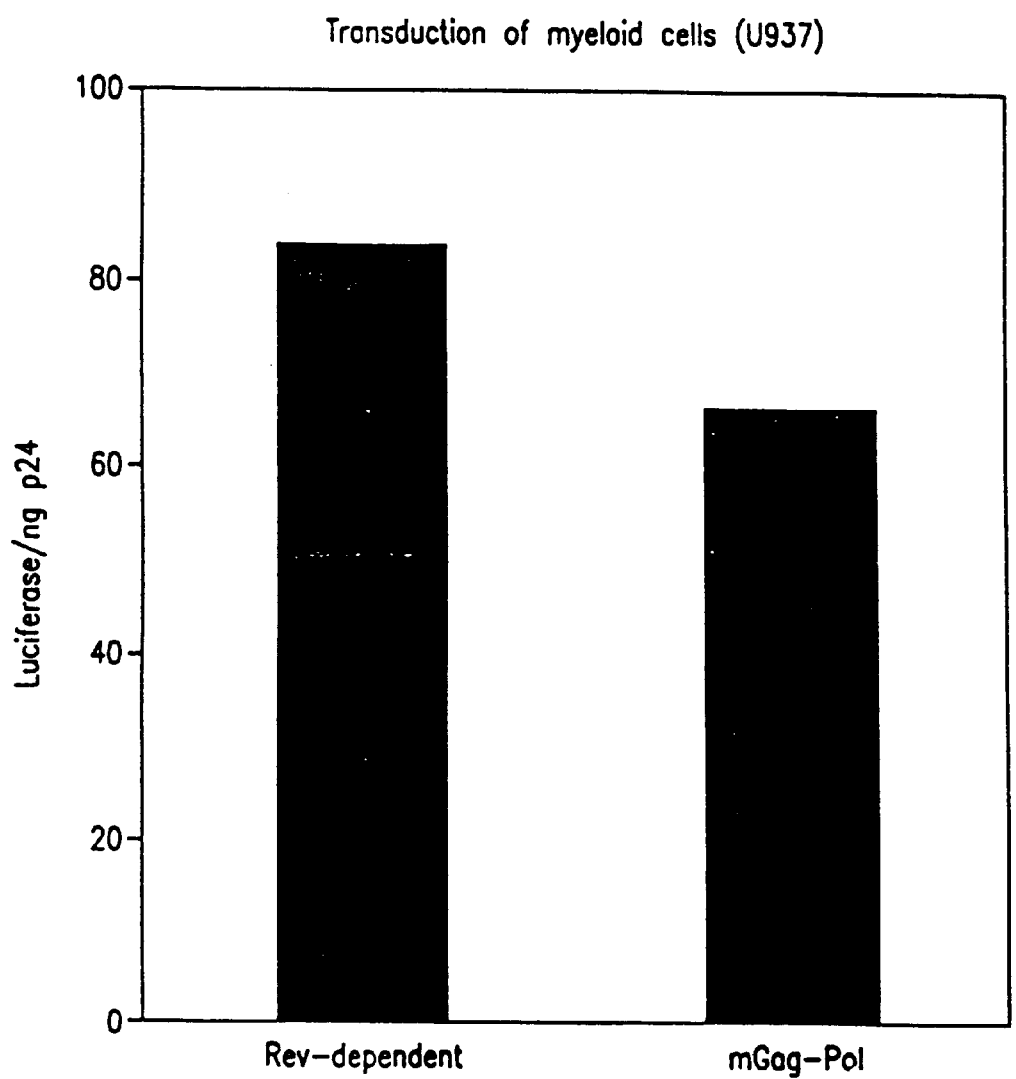
Figure 15D:
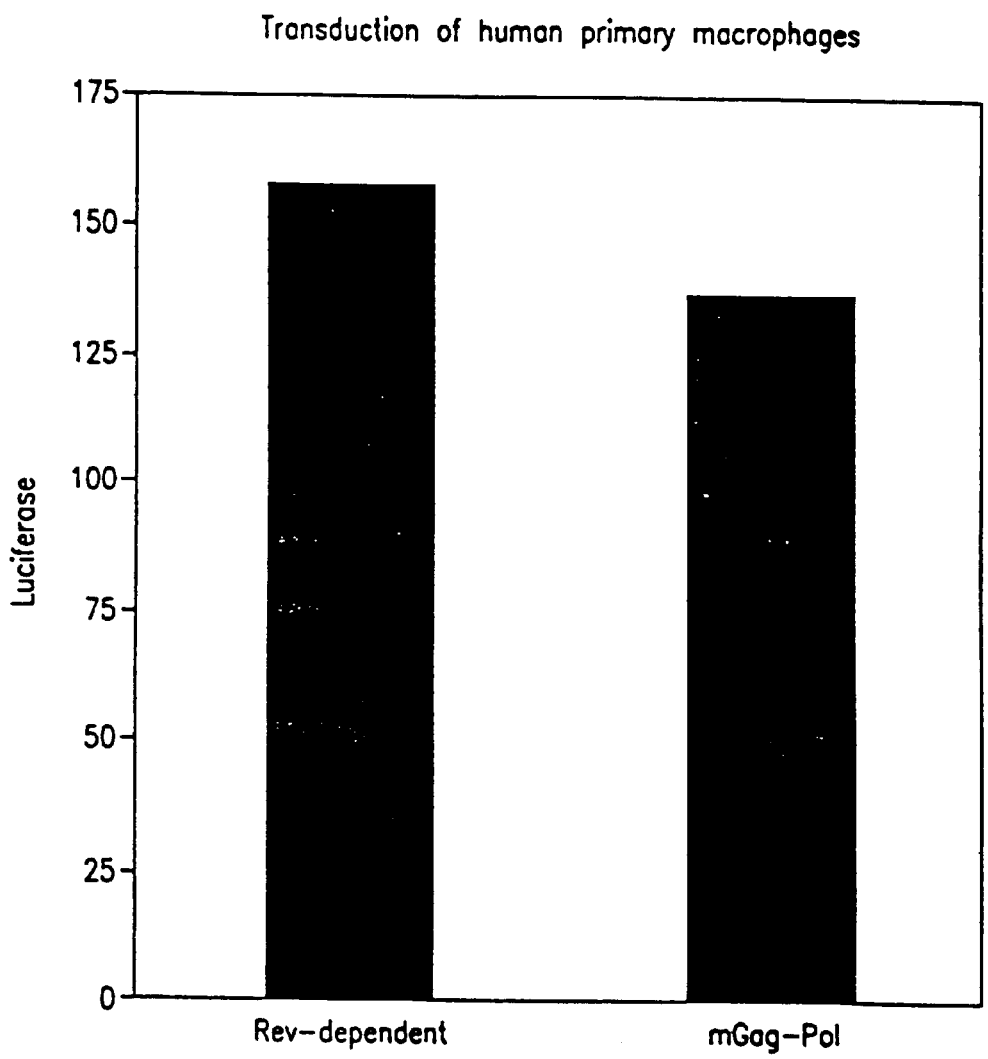

FIG. 14. Bar graph showing reverse transcriptase activity from the Rev-independent gag-pol HIV-1 vector pCMVgag-polBNkan (labeled pCMVBNKan in the figure).

FIGS. 15A–15D. Bar graphs showing the amount of luciferase per nanogram of p24 Gag protein detected in cells transducted with PCMVgagpolBNkan Rev-independent gag-HIV-1 based retroviral vectors. The results show that with PCMVgagpolBNkan Rev-independent gag-HIV-1 based retroviral vectors display high transduction efficiency in (A) 293 cells, (B) human lymphoid cells, (C) human myeloid cells (U937), as well as (D) non-dividing cells such as primary human macrophages.

FIG. 16. Schematic diagram of the SIV envelope encoding vector CMVkan/R-R-SIVgp160CTE.

FIGS. 17A–17D. DNA sequence of the SIV envelope encoding vector CMVkan/R-R-SIVgp160CTE containing a mutated SIV env gene.

V. MODES FOR CARRYING OUT THE INVENTION

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

One aspect of the invention comprises vectors that encode the Gag and/or Pol of HIV-1 in a Rev-independent manner. An example of such a vector which is described herein is the plasmid pCMVgagpolBNkan, which encodes the complete Gag and Pol of HIV-1 in a Rev-independent manner, and also contains a gene conferring kanamycin resistance. This plasmid is Tat and Rev-independent and was generated by eliminating the inhibitory/instability sequences present in the gag/pol mRNA without altering the amino acid sequence of the proteins coded by the genes.

The gag/pol clone of the invention is a DNA construct of the gag/pol region of HIV which has had the inhibitory/instability regions removed. The construct is expected to be useful as a component a new type of lentivirus vector for use in gene therapy or as a vaccine.

The gag, pol or gag/pol sequences of the invention can be highly expressed in human and other mammalian cells in the absence of any other regulatory and structural protein of HIV, including Rev. When the gag/pol sequences are combined with a sequence encoding an envelope protein, such as the VSV G protein or the HIV envelope protein (e.g., in the same vector or in another expression vector), infectious virus is produced after transfection into human cells. When a gene encoding a non-HIV envelope protein is used, for example, in the presence of the HIV gag/pol gene, the virus particles produced would contains only the HIV proteins Gag and Pol.

Lentiviral vectors or vector systems based on the gag, pol or gag/pol sequences of this invention, as exemplified by the Rev-independent pCMVgagpol BNkan construct described herein, may be used for gene therapy in vivo (e.g., parenteral inoculation of high titer vector) or ex vivo (e.g., in vitro transduction of patient's cells followed by reinfusion into the patient of the transduced cells). These procedures are been already used in different approved gene therapy protocols.

The HIV gag/pol clone and SIV gag clone of the invention were made using the method for eliminating inhibitory/instability regions from a gene as described in U.S. Pat. No. 6,174,666, and also in related U.S. Pat. Nos. 5,972,596 and 5,965,726, which are incorporated by reference herein. This method does not require the identification of the exact location or knowledge of the mechanism of function of the INS. Generally, the mutations are such that the amino acid sequence encoded by the mRNA is unchanged, although conservative and non-conservative amino acid substitutions are also envisioned where the protein encoded by the mutated gene is substantially similar to the protein encoded by the non-mutated gene. The mutated genes can be synthetic (e.g., synthesized by chemical synthesis), semi-synthetic (e.g., a combination of genomic DNA, cDNA, or PCR amplified DNA and synthetic DNA), or recombinantly produced. The genes also may optionally not contain introns. The nucleic acids of the invention may also contain Rev-independent fragments of these genes which retain the desired function (e.g., for antigenicity of Gag or Pol, particle formation (Gag) or enzymatic activity (Pol)), or they may also contain Rev-independent variants which have been mutated so that the encoded protein loses a function that is unwanted in certain circumstances. In the latter case, for example, the gene may be modified to encode mutations (at the amino acid level) in the active site of reverse transcriptase or integrase proteins to prevent reverse transcription or integration. Rev-independent fragments of the gag gene are described in U.S. patent application Ser. No. 07/858,747, filed Mar. 27, 1992, and also in related U.S. Pat. Nos. 5,972,596 and 5,965,726, which are incorporated by reference herein.

In addition to being capable of producing HIV Gag and Pol proteins in the absence of Rev regulatory protein in a cell in vivo, the HIV gag/pol clone and SIV gag clone of the invention are also capable of producing HIV Gag and Pol proteins in the absence of any added cis acting transport element, such as CTE or CTE-like elements (collectively referred herein as RNA Transport Elements (RTE)). Experiments indicate that the mutated vectors of the invention for SIV gag are far superior to those adding CTE (see Qiu et al., J. Virol. 73:9145–52 (1999)).

The expression of the proteins encoded by these vectors after transfection into human cells may be monitored at both the level of RNA and protein production. RNA levels are quantitated by methods known in the art, e.g., Northern blots, S1 mapping or PCR methods. Protein levels may also be quantitated by methods known in the art, e.g., western blot or ELISA or fluorescent detection methods. A fast non-radioactive ELISA protocol can be used to detect gag protein (DUPONT or COULTER gag antigen capture assay).

At least three types of lentiviral vectors based on the gag/pol genes of the invention for use in gene therapy and/or as a vaccine are envisioned, i.e., lentiviral vectors having
 a) no round of replication (i.e., a zero replication system)
 b) one round of replication
 c) a fully replicating system For a system with no round of replication, a gag/pol gene, or separate gag and pol genes, or fragments of these genes, expressed using appropriate transcription units, e.g., a CMV promoter and a BGH poly (A) site. This will allow expression of the gag/pol unit (or gag or pol or fragment(s) thereof) for vaccine purposes. This expression can be accomplished without the production of any functional retroviral enzymes, provided that the appropriate mutation(s), e.g., a missense mutation, are introduced. In a zero replication system, a virus stock will be administered to the cells or animals of interest. For example, if one creates and uses a virus stock with the exemplified system using the packaging vector PCMVgagpolBNkan, the transfer construct pmBCwCNluci or pmBCmCNluci, and the envelope containing vector pHCMV-G, one obtains a zero replication system. The virus particles produced by such system can infect cells, and the reverse transcribed transfer construct DNA will go into the nucleus but, because the coding regions for viral structural proteins are not present, there will be no virus expression and replication (0 rounds). If one transfects cells in vivo with the same 3 DNAs, they will go to the nucleus, express viral proteins, make infectious virus particles and go out and infect another cell or cells (1 round). Since in vivo delivery of three plasmids may result in lower expression, at least two different embodiments are envisioned. In the first, two plasmids may be used, e.g., MV1 shown in FIG. 5 and an envelope expression plasmid such as pHCMV-G. Other plasmids encoding functional envelopes from HIV, SIV, or other retroviruses can also be used. Transfection by the two plasmids results in infectious virus that can infect and integrate into new cells (1 round). The infected cells produce gagpol but virus propagation is not possible in the absence of env.

For a system with one round of replication, at least two additional embodiments are envisioned. In the first method, a combination of the genes, e.g., a gag/pol gene, an env encoding gene and, preferably, a gene encoding a reporter protein or other polynucleotide or protein of interest, are delivered into the cells of interest in vivo. As discussed above for the exemplified system, if one transfects cells in vivo with the same 3 DNAs, they will go to the nucleus, express viral proteins, make infectious virus particles, be released and infect another cell or cells (1 round).

In another embodiment, the same result (i.e., only one round of replication) can be obtained by using transfer vectors that have deletions in the 3' LTR and in which a heterologous-promoter (e.g., the CMV-promoter, or inducible promoter, or tissue-specific promoter), is used in place of the '3' LTR promoter. The mutations in the 3' LTR making it inactive upon reverse transcription and integration. This is because the integrated provirus derives both its 5' LTR and its 3' LTR from the 3' LTR of the starting (transfer) construct. (This is a well-known property of all retroviruses and has been used to make self-inactivating vectors (SIN)). There are several reasons one may want to inactivate the incoming LTR promoter, one of which is to use a different tissue specific or regulated promoter for expression of a gene of interest in the integrated provirus. Note that, with SIN vectors, if one uses a viral stock made in vitro after transfection into cells and collection of infectious virus, there will be no round of replication. If one transfects cells with the DNAs in vivo, there will be one round of replication. If functional gag, pol, or env are not included in the DNA mix, there will not be any infection at all (i.e., infectious viruses will not be made).

A fully replicating Rev-independent system has not been constructed yet, although it is expected that a functional system can be constructed using Rev-independent gag/pol and env sequences. If desired, extra posttranscriptional control elements such as the CTE element, which can replace Rev and give infectious virus (see e.g., Zolotukhin et al., J. Virol.68:944–7952 (1994)) are included. The fully replicating system should be in one piece, containing the LTR, packaging signal, gag/pol, splice site, env, tat, one or more CTE or CTE-like elements (if desired for optimal results), and LTR. Tat is thought to be required in this construct, at least in non-permissive cells. Such a system is depicted in FIG. 5, (construct MV2). In this system, a cell or animal of interest (preferably human) would be infected with virus stock that then propagates. CTE or CTE-like elements (depicted in construct MV2 as RTE (RNA Transport Elements)) are desirable since they have been shown to improve expression, and since many retroviruses require the presence of posttranscriptional control elements. There are several types of CTE and CTE-like elements, and these elements appear to work via a different pathway from the Rev-RRE pathway. See, e.g., Tabernero et al., J. Virol. 71:95–101 (1997). See also, Pavlakis and Nappi, PCT/US99/11082, filed May 22, 1999, published as WO 99/61596 on Dec. 2, 1999 (and incorporated herein by reference), which describes a new type of post-transcriptional control element that is able to replace CTE and HIV RRE/Rev. The Pavlakis-Nappi element does not work in the same way as CTE and does not have any sequence or structure homology.

In a preferred embodiment, a lentiviral system of the invention comprises the following three components:

1. a packaging vector containing nucleic acid sequences encoding the elements necessary for vector packaging such as structural proteins (except for HIV env) and the enzymes required to generate vector particles, the packaging vector comprising at least a mutated HIV or SIV gag/pol gene of the invention;

2. a transfer vector containing genetic cis-acting sequences necessary for the vector to infect the target cell and for transfer of the therapeutic or reporter or other gene(s) of interest, the transfer vector comprising the encapsidation signal and the gene(s) of interest or a cloning site for inserting the gene(s) of interest; and 3. a vector containing sequences encoding an element necessary for targeting the viral particle to the intended recipient cell, preferably the gene encoding the G glycoprotein of the vesicular stomatis virus (VSV-G) or amphotrophic MuLV or lentiviral envs.

Using the CMV promoter or other strong, high efficiency, promoter instead of the HIV-1 LTR promoter in the packaging vector, high expression of gag, pol or gag/pol can be achieved in the total absence of any other viral protein. The exchange of the HIV-1 LTR promoter with other promoters is beneficial in the packaging vector or other vectors if constitutive expression is desirable and also for expression in other mammalian cells, such as mouse cells, in which the HIV-1 promoter is weak. Vectors containing the sequences of the invention can be used for the Rev independent production of HIV-1 Gag/Pol, HIV-1 Gag, HIV-1 Pol, and SIV Gag proteins. In certain embodiments, the presence of heterologous promoters will also be desired in the transfer vector and the envelope encoding vector, when such vectors are used.

The gene(s) of interest are chosen according to the effect sought to be achieved. For gene therapy purposes there will be at least one therapeutic gene encoding a gene product which is active against the condition it is desired to treat or prevent. Alternatively or additionally, there may be a gene which acts as a marker by encoding a detectable product. Therapeutic genes may encode, for example, an anti-sense RNA, a ribozyme, a transdominant negative mutant of a target protein, a toxin, a conditional toxin, an antigen that induces antibodies or helper T-cells or cytotoxic T-cells, a single chain antibody or a tumor suppresser protein. See, e.g., WO 98/17816.

An even more extensive list of genes of interest for use in lentiviral vectors is described, e.g., in WO 99/04026 on page 10, line 20 to page 12, line 7. Table 2 of Klimatcheva et al.

(1999) also provides a list of disorders and target cells for gene therapy, as well as a number of lentiviral vectors used by others. This list includes genetic/metabolic deficiencies, viral infection and cancer. Inherited genetic defects such as adenosine deaminase deficiency, familial hypercholesterolemia, cystic fibrosis, mucopolysaccharidosis type VII, types I and II diabetes, classical phenylketonuria and Gaucher disease are diseases which are listed as being possible to overcome by lentiviral vector-mediated gene therapy because they constitute single-gene deficiencies for which the involved genes are known. Viral diseases are also listed as constituting appropriate targets for lentiviral gene delivery. In particular, a number of gene therapy approaches have been proposed for the treatment of HIV infection and, for some of these strategies, phase I studies have recently begun in humans. The article states that preliminary studies have dealt with defective murine oncoviruses for delivery of anti-sense RNAs, ribozymes and transdominant proteins against HIV replication.

In any of the vectors, but preferably in the transfer vector, an inserted gene could have an internal ribosomal entry site (IRES), e.g., from picornaviral RNA. An IRES will be used in circumstances that one wants to express two proteins from the same promoter. For example one protein of interest and a marker gene, e.g., green fluorescent protein (GFP) or a marker gene and a drug resistance gene (e.g. the firefly luciferase gene and neomycin phosphotransferase gene) as described on p. 58 of WO 99/04026, for example. Using an IRES the expression of the two proteins is coordinated. A further gene or genes may also be present under the control of a separate promoter. Such a gene may encode for example a selectable marker, or a further therapeutic agent which may be among the therapeutic agents listed above. Expression of this gene may be constitutive; in the case of a selectable marker this may be useful for selecting successfully transfected packaging cells, or packaging cells which are producing particularly high titers of the retroviral vector particles. Alternatively or additionally, the selectable marker may be useful for selecting cells which have been successfully infected with the lentiviral vector and have the provirus integrated into their own genome.

One way of performing gene therapy is to extract cells from a patient, infect the extracted cells with a lentiviral vector and reintroduce the cells back into the patient. A selectable marker may be used to provide a means for enriching for infected or transduced cells or positively selecting for only those cells which have been infected or transduced, before reintroducing the cells into the patient. This procedure may increase the chances of success of the therapy. Selectable markers may be for instance drug resistance genes, metabolic enzyme genes, or any other selectable markers known in the art. Typical selection genes encode proteins that confer resistance to antibiotics and other toxic substances, e.g., histidinol, puromycin, hygromycin, neomycin, methotrexate etc. and cell surface markers.

However, it will be evident that for many gene therapy applications of lentiviral vectors, selection for expression of a marker gene may not be possible or necessary. Indeed expression of a selection marker, while convenient for in vitro studies, could be deleterious in vivo because of the inappropriate induction of cytotoxic T lymphocytes (CTLs) directed against the foreign marker protein. Also, it is possible that for in vivo applications, vectors without any internal promoters will be preferable. The presence of internal promoters can affect for example the transduction titres obtainable from a packaging cell line and the stability of the integrated vector. Thus, single transcription unit vectors, which may be bi-cistronic or poly-cistronic, coding for one or two or more therapeutic genes, may be the preferred vector designed for use in vivo. See, e.g., WO 98/17816.

Suitable host or producer cells for use in the invention are well known in the art. May lentiviruses have already been split into replication defective genomes and packaging components. For those which have not the technology is available for doing so. The producer cell encodes the viral components not encoded by the vector genome such as the Gag, Pol and Env proteins. The gag, pol and env genes may be introduced into the producer cell transiently, or may be stably integrated into the cell genome to give a packaging cell line. The lentiviral vector genome is then introduced into the packaging cell line by transfection or transduction to create a stable cell line that has all of the DNA sequences required to produce a lentiviral vector particle. Another approach is to introduce the different DNA sequences that are required to produce lentiviral vector particle, e.g., the env coding constrict, the gag-pol coding construct and the transfer construct into the cell simultaneously by transient triple transfection.

Target cells identified by Klimatcheva et al. (1999), and the references cited therein, include airway epithelial cells for cystic fibrosis; retinal photoreceptor cells for retinitis pigmentosa; progenitors for red blood cells, macrophages, and lymphocytes for hematopoietic disorders, sickle cell anemia, $\beta$-thalassemia, lysosomal storage disorders, mucopolysaccharidoses, and severe combined immunodeficiency syndrome; bone marrow cells and macrophages for Gaucher's disease; liver cells for familial hypercholesterolaemia; T-lymphocytes and macrophages for HIV infection; brain tissue, neurons, and glial cells for neurodegenerative diseases such as Parkinson's and Alzheimer's diseases; endothelial cells and cardiac myocytes for cardiovascular diseases; and cancer cells in various tissues (e.g. liver or brain) for cancer. Target cells for other diseases would be apparent to one of skill in the art.

Vaccines and pharmaceutical compositions comprising at least one of the nucleic acid sequences, vectors, vector systems, or transduced or transfected host cells of the invention and a physiologically acceptable carrier are also part of the invention.

As used herein, the term "transduction" generally refers to the transfer of genetic material into the host via infection, e.g., in this case by the lentiviral vector. The term "transfection" generally refers to the transfer of isolated genetic material into cells via the use of specific transfection agents (e.g., calcium phosphate, DEAE Dextran, lipid formulations, gold particles, and other microparticles) that cross the cytoplasmic membrane and deliver some of the genetic material into the cell nucleus.

Systems similar to those described herein can be produced using elements of lentiviruses in addition to the HIV and/or SIV genes described herein.

Pharmaceutical Compositions

The pharmaceutical compositions of the invention contain a pharmaceutically and/or therapeutically effective amount of at least one nucleic acid construct, vector, vector system, viral particle/virus stock, or host cell (i.e., agents) of the invention. In one embodiment of the invention, the effective amount of an agent of the invention per unit dose is an amount sufficient to cause the detectable expression of the gene of interest. In another embodiment of the invention, the effective amount of agent per unit dose is an amount sufficient to prevent, treat or protect against deleterious effects (including severity, duration, or extent of symptoms) of the condition being treated. The effective amount of agent per unit dose depends, among other things, on the species of mammal inoculated, the body weight of the mammal and the chosen inoculation regimen, as is well known in the art. The dosage of the therapeutic agents which will be most suitable for prophylaxis or treatment will also vary with the form of administration, the particular agent chosen and the physiological characteristics of the particular patient under treatment. The dose is administered at least once. Subsequent doses may be administered as indicated.

To monitor the response of individuals administered the compositions of the invention, mRNA or protein expression levels may be determined. In many instances it will be sufficient to assess the expression level in serum or plasma obtained from such an individual. Decisions as to whether to administer another dose or to change the amount of the composition administered to the individual may be at least partially based on the expression levels.

The term "unit dose" as it pertains to the inocula refers to physically discrete units suitable as unitary dosages for mammals, each unit containing a predetermined quantity of active material (e.g., nucleic acid, virus stock or host cell) calculated to produce the desired effect in association with the required diluent. The titers of the virus stocks to be administered to a cell or animal will depend on the application and on type of delivery (e.g., in vivo or ex vivo). The virus stocks can be concentrated using methods such as centrifugation. The titers to be administered ex vivo are preferably in the range of 0.001 to 1 infectious unit/cell. Another method of generating viral stocks is to cocultivate stable cell lines expressing the virus with the target cells. This method has been used to achieve better results when using traditional retroviral vectors because the cells can be infected over a longer period of time and they have the chance to be infected with multiple copies of the vector.

For in vivo administration of nucleic acid constructs, vectors, vector systems, virus stocks, or cells which have been transduced or transfected ex vivo, the dose is to be determined by dose escalation, with the upper dose being limited by the onset of unacceptable adverse effects. Preliminary starting doses may be extrapolated from experiments using lentiviral vectors in animal models, by methods known in the art, or may be extrapolated from comparisons with known retroviral (e.g., adenoviral) doses. Generally, small dosages will be used initially and, if necessary, will be increased by small increments until the optimum effect under the circumstances is reached. Exemplary dosages are within the range of $10^8$ up to approximately $5 \times 10^{15}$ particles.

Inocula are typically prepared as a solution in a physiologically acceptable carrier such as saline, phosphate-buffered saline and the like to form an aqueous pharmaceutical composition.

The agents of the invention are generally administered with a physiologically acceptable carrier or vehicle therefor. A physiologically acceptable carrier is one that does not cause an adverse physical reaction upon administration and one in which the nucleic acids are sufficiently soluble to retain their activity to deliver a pharmaceutically or therapeutically effective amount of the compound. The pharmaceutically or therapeutically effective amount and method of administration of an agent of the invention may vary based on the individual patient, the indication being treated and other criteria evident to one of ordinary skill in the art. A therapeutically effective amount of a nucleic acid of the invention is one sufficient to prevent, or attenuate the severity, extent or duration of the deleterious effects of the condition being treated without causing significant adverse side effects. The route(s) of administration useful in a particular application are apparent to one or ordinary skill in the art.

Routes of administration of the agents of the invention include, but are not limited to, parenteral, and direct injection into an affected site. Parenteral routes of administration include but are not limited to intravenous, intramuscular, intraperitoneal and subcutaneous. The route of administration of the agents of the invention is typically parenteral and is preferably into the bone marrow, into the CSF intramuscular, subcutaneous, intradermal, intraocular, intracranial, intranasal, and the like. See, e.g., WO 99/04026 for examples of formulations and routes of administration.

The present invention includes compositions of the agents described above, suitable for parenteral administration including, but not limited to, pharmaceutically acceptable sterile isotonic solutions. Such solutions include, but are not limited to, saline and phosphate buffered saline for nasal, intravenous, intramuscular, intraperitoneal, subcutaneous or direct injection into a joint or other area.

In providing the agents of the present invention to a recipient mammal, preferably a human, the dosage administered will vary depending upon such factors as the mammal's age, weight, height, sex, general medical condition, previous medical history and the like.

The administration of the pharmaceutical compositions of the invention may be for either "prophylactic" or "therapeutic" purpose. When provided prophylactically, the compositions are provided in advance of any symptom. The prophylactic administration of the composition serves to prevent or ameliorate any subsequent deleterious effects (including severity, duration, or extent of symptoms) of the condition being treated. When provided therapeutically, the composition is provided at (or shortly after) the onset of a symptom of the condition being treated.

For all therapeutic, prophylactic and diagnostic uses, one or more of the agents of the invention, as well as antibodies and other necessary reagents and appropriate devices and accessories, may be provided in kit form so as to be readily available and easily used.

Where immunoassays are involved, such kits may contain a solid support, such as a membrane (e.g., nitrocellulose), a bead, sphere, test tube, rod, and so forth, to which a receptor such as an antibody specific for the target molecule will bind. Such kits can also include a second receptor, such as a labeled antibody. Such kits can be used for sandwich assays to detect toxins. Kits for competitive assays are also envisioned.

VI. INDUSTRIAL APPLICABILITY

Mutated genes of this invention can be expressed in the native host cell or organism or in a different cell or organism. The mutated genes can be introduced into a vector such as a plasmid, cosmid, phage, virus or mini-chromosome and inserted into a host cell or organism by methods well known in the art. In general, the mutated genes or constructs containing these mutated genes can be utilized in any cell, either eukaryotic or prokaryotic, including mammalian cells (e.g., human (e.g., HeLa), monkey (e.g., Cos), rabbit (e.g., rabbit reticulocytes), rat, hamster (e.g., CHO and baby hamster kidney cells) or mouse cells (e.g., L cells), plant cells, yeast cells, insect cells or bacterial cells (e.g., E. coli. The vectors which can be utilized to clone and/or express these mutated genes are the vectors which are capable of replicating and/or expressing the mutated genes in the host cell in which the mutated genes are desired to be replicated and/or expressed. See, e.g., F. Ausubel et al., *Current Protocols in Molecular Biology*, Greene Publishing Associates and Wiley-Interscience (1992) and Sambrook et al. (1989) for examples of appropriate vectors for various types of host cells. The native promoters for such genes can be replaced with strong promoters compatible with the host into which the gene is inserted. These promoters may be inducible. The host cells containing these mutated genes can be used to express large amounts of the protein useful in enzyme preparations, pharmaceuticals, diagnostic reagents, vaccines and therapeutics.

Mutated genes or constructs containing the mutated genes may also be used for in-vivo or in-vitro gene therapy. For example, a mutated gene of the invention will produce an mRNA in situ to ultimately increase the amount of protein expressed. Such gene include viral genes and/or cellular genes. Such a mutated gene is expected to be useful, for example, in the development of a vaccine and/or genetic therapy.

The constructs and/or proteins made by using constructs encoding the mutated gag, env, and pol genes could be used, for example, in the production of diagnostic reagents, vaccines and therapies for AIDS and AIDS related diseases. The inhibitory/instability elements in the HIV-1 gag gene may be involved in the establishment of a state of low virus production in the host. HIV-1 and the other lentiviruses cause chronic active infections that are not cleared by the immune system. It is possible that complete removal of the inhibitory/instability sequence elements from the lentiviral genome would result in constitutive expression. This could prevent the virus from establishing a latent infection and escaping immune system surveillance. The success in increasing expression of the entire gag/pol gene by eliminating the inhibitory sequence element suggests that one could produce lentiviruses without any negative elements. Such lentiviruses could provide a novel approach towards attenuated vaccines.

For example, vectors expressing high levels of Gag can be used in immunotherapy and immunoprophylaxis, after expression in humans. Such vectors include retroviral vectors and also include direct injection of DNA into muscle cells or other receptive cells, resulting in the efficient expression of gag, using the technology described, for example, in Wolff et al., *Science* 247:1465–1468 (1990), Wolff et al., *Human Molecular Genetics* 1(6):363–369 (1992) and Ulmer et al., *Science* 259:1745–1749 (1993). Further, the gag constructs could be used in transdominant inhibition of HIV expression after the introduction into humans. For this application, for example, appropriate vectors or DNA molecules expressing high levels of $p55^{gag}$ or $p37^{gag}$ would be modified to generate transdominant gag mutants, as described, for example, in Trono et al., *Cell* 59:113–120 (1989). The vectors would be introduced into humans, resulting in the inhibition of HIV production due to the combined mechanisms of gag transdominant inhibition and of immunostimulation by the produced gag protein. In addition, the gag constructs of the invention could be used in the generation of new retroviral vectors based on the expression of lentiviral gag proteins. Lentiviruses have unique characteristics that may allow the targeting and efficient infection of non-dividing cells. Similar applications are expected for vectors expressing high levels of env.

Identification of similar inhibitory/instability elements in SIV indicates that this virus is a convenient model to test these hypotheses. SIV similarly modified could be used in place of HIV in an effort to further minimize the possibility of rearrangement events that would lead to the generation of infectious HIV.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

Rev-Independent HIV-1 Gag/Pol Molecular Clone

FIG. 1 shows the DNA sequence of a Rev-independent HIV-1 gag/pol molecular clone. This DNA sequence shown encodes the complete Gag and Pol of HIV-1 and can be expressed in a Rev-independent manner when operably linked to a promoter. The Rev-independent gag sequence was described in U.S. Pat. Nos. 6,174,666, 5,972,596 and 5,965,726 and the Rev-independent pol sequence was generated by eliminating the inhibitory/instability sequences using the methods described in those,patents. Others have reportedly made Rev independent gag sequences by optimizing codon usage for human cells (see, e.g., WO 98/34640).

FIG. 2 shows an alignment of the sequence of the wild-type and mutated pol region in pCMVgagpolBNkan. Position #1 in the figure is position 2641 in plasmid pCMVgagpolBNkan.

The elimination of INS in gag, pol and env regions allows the expression of high levels of authentic HIV-1 structural proteins in the absence of the Rev regulatory factor of HIV-1.

EXAMPLE 2

Rev-Independent SIV Gag Molecular Clone

FIG. 3 shows the DNA sequence of a Rev-independent SIV gag molecular clone, SIVgagDX. FIG. 4 shows the comparison of wild type (WT) and mutant (SIVgagDX) sequences. The wild type SIV sequence is from Simian (macaque) immunodeficiency virus isolate 239, clone lambda siv 239-1 (GenBank accession No. M33262).

EXAMPLE 3

Rev-Independent SIV Env Molecular Clone

FIG. 16 shows a schematic diagram, and FIG. 17 shows the DNA sequence, of the "env-coding" vector CMVkan/R-R-SIVgp160CTE, which is an example of a vector comprising a mutated lentiviral env gene sequence which is capable of being expressed independently of any SIV or HIV regulatory factors. "CMV" denotes the cytomegalovirus promoter, "SRV-CTE" denotes the constitutive transport element (CTE) of Simian Retrovirus Type 1; "all-STOP" denotes a sequence providing translational stops in all three reading frames; "BGH terminator" denotes the bovine growth hormone polyadenylation signal. Other posttranscriptional control elements can be used instead of the indicated SRV-CTE, for example the one described by Pavlakis and Nappi, PCT/US99/11082, filed May 22, 1999, which was published as WO 99/61596 on Dec. 2, 1999 (and which is incorporated herein by reference).

As mentioned previously above, such a vector encoding a lentiviral env gene may be used if it is desired that the vector infect CD4+T cells. Also as mentioned previously above, the CTE element (i.e., the SRV-CTE element in the case of vector CMVkan/R-R-SIVgp160CTE), can be replaced with another post-transcriptional control element, such as the Pavlakis-Nappi element, that is able to replace CTE and HIV RRE/Rev. See Pavlakis and Nappi, PCT/US99/11082, filed May 22, 1999, which was published as WO 99/61596 on Dec. 2, 1999 (and which is incorporated herein by reference).

EXAMPLE 4

Lentivirial Vector System

FIG. 5 is a schematic of some of the components of a preliminary version of the Rev-independent lentiviral vector system exemplified herein, including a packaging construct and three different transfer vectors which may be used. In the lentiviral system exemplified herein, the packaging construct also contains the gene for kanamycin resistance. The lentiviral system exemplified herein also contains the vector pHCMV-G, which is shown in FIG. 5.

In the packaging construct shown in FIG. 5, "CMV" denotes the cytomegalovirus promoter, "Gag" denotes the gag gene, which generates components of the virion core, "Pro" denotes "protease" "RT" denotes "reverse transcriptase," "Int" denotes "integrase" and "BGH poly (A)" denotes the bovine growth hormone polyadenylation signal. The protease, reverse transcriptase, and integrase genes comprise the "pol" gene. In transfer construct 1, "LTR" denotes the HIV "long terminal repeat", which contains a HIV promoter; "mSD" denotes "mutated splice donor site," which is present in the construct so that splicing of the RNA transcript does not occur; "ψ" denotes the encapsidation signal; "wGA" denotes part of the wild-type gag gene which contains sequences believed to be necessary for encapsidation; "X" indicates that the ATG codon of the partial gag gene sequence is mutated so that translation of this gene does not occur; "CMV" denotes the cytomegalovirus promoter and luciferase is used as a reporter gene. Luciferase can be replaced with any gene of interest. Another HIV LTR is present at the 3' end of transfer construct 1. Replacement of this LTR in constructs such as the transfer construct 1, 2, or 3 with a promoter-enhancer deleted HIV LTR leads to inactivation of LTR after integration. Transfer construct 2 is similar to transfer construct 1, the difference being that a mutated part of the gag gene (denoted "mGa") is used instead of the wild-type part of the gag gene. Transfer construct 3 (pm2BCwCNluci) has different mutations at the 5' splice site and has an intact ATG codon so that translation of part of the mutated gag gene occurs. Transfer construct 3 also has a 5' CMV promoter instead of a 5' LTR promoter. This construct is expressed independent of the presence of HIV Tat protein. The transfer constructs expressed from the LTR promoter are partially dependent on Tat protein. In 293 cells significant expression can be achieved in the absence of Tat. See, e.g., Valentin et al., Proc. Natl Acad. Sci. U S A. 95:8886–91 (1988).

EXAMPLE 5

Generation of Packaging Construct pCMVgagpol BNkan

FIG. 6 shows a schematic map of the packaging construct pCMV gagpolBNKan. The nucleotide numbering is that of the HXB2R sequence (Genbank accession number K03455 and M38432), where +1 is the start of transcription.

The sequence in HIV-1 gag/pol region was mutated in order to eliminate all the INS. The fragment from the beginning of gag to BsrGI site in pol and the fragment KE [KpnI(3700)-EcoRI(4194)] were previously mutated described in Schneider et al., J. Virol. 71:4892–4903 (1997) and in U.S. Pat. Nos. 6,174,666, 5,972,596 and 5,965,726.

To generate pCMVgagpolBNkan, three fragments within HIV-1 pol region were mutated. They are fragment BP [BsrGI(2207)PflMI(3032)], fragment PK [PflMI(3032)-KpnI(3700)] and fragment EN [EcoRI(4194)-NdeI(4668)]. Mutagenesis was performed using a modified version of the method described by Ho et al., Gene 77:51–59 (1989) and DNA shuffling (Zhao and Arnold, Nucl. Acid Res. 25(6), 1307–1308 (1997). Sixteen oligonucleotides extending over the complete sequence of the three fragments were designed. Six oligos corresponded to fragment BP, six to fragment PK, and four to fragment EN (the oligonucleotides ranged from 130 to 195 bases in length; adjacent oligos overlapped by twenty nucleotides). Each fragment was assembled in two steps:

1) PCR; the reaction was carried out in standard pfu buffer with 10 pmol of each purified big oligo, 0.2 mM of each dNTPs and 2.5 u pfu DNA polymerase enzyme (Stratagene) in a 50 μl final volume. The PCR program was: 3 min 96° C. followed by 50 cycles of 1 min 94° C., 1 min 55° C., and 1 min +5 s/cycle 72° C., ended by 7 min at 72° C. After PCR, the big oligonucleotides were removed from the assembled mutated fragment.

2) The second step was to specifically amplify the assembled products with 30 mer primers located at the 5' and 3' end of each mutated fragment. One microliter of the assembled PCR product was used as template in a 25-cycle PCR reaction with 50 pmol of each primer, 1×pfu buffer, 0.2 mM of each dNTP and 2.5 u pfu DNA polymerase in a 50 μl final volume. The PCR program was: 3 min 96° C., 10 cycles of 30 s 94° C., 30 s 55° C., 45 s 72° C., followed by another 14 new line cycles of 30 s 94° C., 30 s 55° C., 45 s +20 s/cycle 72° C., and finally 7 min 72° C. This program gave a single PCR product of the correct size. The amplified BP, PK and EN fragments were individually cloned into PCR-script™ vector using PCR-script™ Amp SK(+) Cloning Kit (Stratagene). Clones were randomly selected and sequenced. The correct BP, PK and EN fragments together with fragment KE previously mutated by Schneider et al. were ligated between BsrGI and KpnI site of p55AM1-R5 (which was previously described in Schneider et al., J. Virol. 71: 4892–4903 (1997)) to produce a completely mutated gagpol ORF. The new plasmid containing the completely mutated gag/pol was named pLTRgagpolBN. BN stands for the modification of the fragment between BsrGI and NdeI. The mutated gag/pol was then cloned into a CMVkan vector containing the cytomegalovirus major late promoter (GenBank accession no. X17403) and the kanamycin resistance gene, resulting in pCMVgagpolBNkan. The plasmid backbone comes from pVR1332 provided by Vical Inc., and described in Hartikka et al., Hum Gene Ther. 7:1205–17 (1996).

It is understood that different plasmid backbones can be used, e.g., to provide good expression in vivo, in the case of DNA injection, for example.

EXAMPLE 6

Construction of Transfer Vectors pmBCwCNluci and pmBCmCNluci

The HIV-1 sequence BC, between BssHII (257) and ClaI (376), contains the major splice donor site and the encapsidation signal. Six oligos (33 to 46 bases) were designed to introduce mutations on the splice donor site and the AUG start codon of gag. The BC fragment was assembled, amplified and sequenced as described in the section concerning the construction of pCMVgagpolBN.

The mutated BC fragment and a fragment of wild type gag between ClaI (376) and Nsi (793) were placed between the BssHII and Nsi sites of p55RRE (Schneider et al., J. Virol. 71:4892–4903 (1997)) to generate pmBCwCN. In parallel, the fragment between ClaI (376) and NsiI sites of mutated gag from p55BM1-10SD+ was used to generate pmBCmCN. (p55BM1–10OSD+ is similar to p55BM1-10, which is described in Schneider et al. (1997), but contains in addition the intact splice donor and encapsidation site upstream of gag). The region between NsiI and XhoI containing 3' part of gag and RRE in pmBCwCN and pmBCmCN was replaced by a ClaI-XhoI fragment containing CMV promoter and luciferase gene from pHR'-CMVluci (vector from D. Trono) to generate pmBCwCNluci and pmBCmCNluci (which are shown as transfer constructs 1 and 2 in FIG. 5, and schematically depicted in FIGS. 7 and 8, respectively). The sequences of these plasmids are shown in FIGS. 10 and 11, respectively. Different versions of these plasmids have also been created, by standard procedures, with variations in the region of the encapsidation site, the first splice donor site, and the initiator gag AUG. For example, the transfer construct pm2BcwCNluci (which is shown as transfer construct 3 in FIG. 5) has different mutations in the 5' splice site region and has an intact ATG. A comparison of the sequences in the BssHII-Cla I region of transfer constructs 1 and 2 (mBCwCN frag), transfer construct 3 (m2BCwCN frag), HXB2 and NL43 is shown in FIG. 12.

EXAMPLE 7

Preparation of Viral Particles

Lentiviral particles were generated by transient cotransfection of 293 human kidney cells with a combination of three plasmids: pCMVgagpolBNkan, pmBCwCNluci or pmBCmCNluci (transfer vector) and pHCMV-G (Yee et al., Proc. Natl. Acad. Sci., USA, 91:9564–9568 (1994) a plasmid coding for the envelope VSV-G (glycoprotein of vesicular stomatitis virus).

The day before the transfection, 293 cells were plated at a density of $10^6$ cells/plate on a 60 mm plate. Plasmid DNA was transfected by the Ca-phosphate precipitation method in the following proportions: 3 µg packaging construct, 6 µg transfer construct and 100 ng VSV-G encoding construct, pHCMV-G. [Note that the LTR promoter can be expressed in 293 cells in the absence of Tat with a moderate decrease in efficiency. The transfer constructs can be fully Tat independent after replacement of the LTR promoter with a CMV (see, e.g., transfer construct 3 in FIG. 5) or other promoter in such a way that the mRNA start site is at the beginning of the LTR R region.] In the present experiments for preparation of viral particles 500 ng of a Tat expression plasmid was included in the transfection.

Cells were washed the day after transfection and were kept in DMEM medium for another 48 hours before the supernatants were harvested. Supernatants were spun at 1,200 rpm for 7 mins to eliminate any floating cells. pCMVgagpolBNkan produces high levels of Gag protein that is efficiently released from the cells (FIG. 13), and also produces high levels of functional Pol as judged by levels of reverse transcriptase activity similar to those found upon expression of complete HIV-1 (FIG. 14).

Supernatants from 293 transfected cells were used to transduce several human cell lines (293, Jurkat, U937) and non-dividing human primary macrophages.

EXAMPLE 8

Cell Transduction

Transduction was performed by incubating for 3–4 hours at 37° C. the target cells with 1–2 ml of supernatant containing the retroviral vectors. The amount of retroviral vector present in the supernatant was normalized by p24 content (measured by ELISA). Equal amounts of p24 gag protein were used for infection of cells. This way, differences in production of the different preparations was minimized.

The macrophages used for transduction were isolated from the peripheral blood of healthy donors by adherence to plastic. Cells were cultured in RPMI +20% fetal calf serum (FCS) +10% human serum (HS). After 1 week, non-adherent cells were washed off with PBS and the macrophages were kept in culture for another 1–2 weeks in the absence of human serum. The cells were washed 2–4 times with PBS before transduction.

Cells were harvested 48 hours after transduction (seven days for primary macrophages) and the transduction efficiency was determined by measuring luciferase activity in cell extracts from the cultures. The results of the transduction experiments in 293 Jurkat, U937 and primary macrophages are shown in FIGS. 15A–D. These results demonstrate that Rev-independent gag-HIV-1 based retroviral vectors display high transduction efficiency in (A) 293 cells, (B) human lymphoid cells, (C) human myeloid cells (U937), as well as (D) non-dividing cells such as primary human macrophages.

EXAMPLE 9

Use Of Nucleic Acids of the Invention In Immunoprophylaxis or Immunotherapy

In postnatal gene therapy, new genetic information has been introduced into tissues by indirect means such as removing target cells from the body, infecting them with viral vectors carrying the new genetic information, and then reimplanting them into the body; or by direct means such as encapsulating formulations of DNA in liposomes; entrapping DNA in proteoliposomes containing viral envelope receptor proteins; calcium phosphate co-precipitating DNA; and coupling DNA to a polylysine-glycoprotein carrier complex. In addition, in vivo infectivity of cloned viral DNA sequences after direct intrahepatic injection with or without formation of calcium phosphate coprecipitates has also been described. mRNA sequences containing elements that enhance stability have also been shown to be efficiently translated in Xenopus laevis embryos, with the use of cationic lipid vesicles. See, e.g., J. A. Wolff, et al., Science 247:1465–1468 (1990) and references cited therein.

Recently, it has also been shown that injection of pure RNA or DNA directly into skeletal muscle results in significant expression of genes within the muscle cells. J. A. Wolff, et al., Science 247:1465–1468 (1990). Forcing RNA or DNA introduced into muscle cells by other means such as by particle-acceleration (N. -S. Yang, et al. Proc. Natl. Acad. Sci. USA 87:9568–9572 (1990); S. R. Williams et al., Proc. Natl. Acad. Sci. USA 88:2726–2730 (1991)) or by viral transduction should also allow the DNA or RNA to be stably maintained and expressed. In the experiments reported in Wolff et al., RNA or DNA vectors were used to express reporter genes in mouse skeletal muscle cells, specifically cells of the quadriceps muscles. Protein expression was readily detected and no special delivery system was required for these effects. Polynucleotide expression was also obtained when the composition and volume of the injection fluid and the method of injection were modified from the described protocol. For example, reporter enzyme activity was reported to have been observed with 10 to 100 µl of hypotonic, isotonic, and hypertonic sucrose solutions, Opti-MEM, or sucrose solutions containing 2 mM $CaCl_2$ and also to have been observed when the 10- to 100-µl injections were performed over 20 min. with a pump instead of within 1 min.

Enzymatic activity from the protein encoded by the reporter gene was also detected in abdominal muscle injected with the RNA or DNA vectors, indicating that other muscles can take up and express polynucleotides. Low amounts of reporter enzyme were also detected in other tissues (liver, spleen, skin, lung, brain and blood) injected with the RNA and DNA vectors. Intramuscularly injected plasmid DNA has also been demonstrated to be stably expressed in non-human primate muscle. S. Jiao et al., *Hum. Gene Therapy* 3:21–33 (1992).

It has been proposed that the direct transfer of genes into human muscle in situ may have several potential clinical applications. Muscle is potentially a suitable tissue for the heterologous expression of a transgene that would modify disease states in which muscle is not primarily involved, in addition to those in which it is. For example, muscle tissue could be used for the heterologous expression of proteins that can immunize, be secreted in the blood, or clear a circulating toxic metabolite. The use of RNA and a tissue that can be repetitively accessed might be useful for a reversible type of gene transfer, administered much like conventional pharmaceutical treatments. See J. A. Wolff, et al., *Science* 247:1465–1468 (1990) and S. Jiao et al., *Hum. Gene Therapy* 3:21–33 (1992).

It had been proposed by J. A. Wolff et al., supra, that the intracellular expression of genes encoding antigens might provide alternative approaches to vaccine development. This hypothesis has been supported by a recent report that plasmid DNA encoding influenza A nucleoprotein injected into the quadriceps of BALB/c mice resulted in the generation of influenza A nucleoprotein-specific cytotoxic T lymphocytes (CTLs) and protection from a subsequent challenge with a heterologous strain of influenza A virus, as measured by decreased viral lung titers, inhibition of mass loss, and increased survival. J. B. Ulmer et al., *Science* 259:1745–1749 (1993).

Therefore, it appears that the direct injection of RNA or DNA vectors encoding the viral antigen can be used for endogenous expression of the antigen to generate the viral antigen for presentation to the immune system without the need for self-replicating agents or adjuvants, resulting in the generation of antigen-specific CTLs and protection from a subsequent challenge with a homologous or heterologous strain of virus.

CTLs in both mice and humans are capable of recognizing epitopes derived from conserved internal viral proteins and are thought to be important in the immune response against viruses. By recognition of epitopes from conserved viral proteins, CTLs may provide cross-strain protection. CTLs specific for conserved viral antigens can respond to different strains of virus, in contrast to antibodies, which are generally strain-specific.

Thus, direct injection of RNA or DNA encoding the viral antigen has the advantage of being without some of the limitations of direct peptide delivery or viral vectors. See J. A. Ulmer et al., supra, and the discussions and references therein). Furthermore, the generation of high-titer antibodies to expressed proteins after injection of DNA indicates that this may be a facile and effective means of making antibody-based vaccines targeted towards conserved or non-conserved antigens, either separately or in combination with CTL vaccines targeted towards conserved antigens. These may also be used with traditional peptide vaccines, for the generation of combination vaccines. Furthermore, because protein expression is maintained after DNA injection, the persistence of B and T cell memory may be enhanced, thereby engendering long-lived humoral and cell-mediated immunity.

1. Vectors for the Immunoprophylaxis or Immunotherapy Against HIV-1

The mutated gag, pol or gag/pol sequences will be inserted in expression vectors using a strong constitutive promoter such as CMV or RSV, or an inducible promoter such as HIV-1.

The vector will be introduced into animals or humans in a pharmaceutically acceptable carrier using one of several techniques such as injection of DNA directly into human tissues; electroporation or transfection of the DNA into primary human cells in culture (ex vivo), selection of cells for desired properties and reintroduction of such cells into the body, (said selection can be for the successful homologous recombination of the incoming DNA to an appropriate preselected genomic region); generation of infectious particles containing the gag gene, infection of cells ex vivo and reintroduction of such cells into the body; or direct infection by said particles in vivo.

Substantial levels of protein will be produced leading to an efficient stimulation of the immune system.

In another embodiment of the invention, the described constructs will be modified to express mutated Gag proteins that are unable to participate in virus particle formation. It is expected that such Gag proteins will stimulate the immune system to the same extent as the wild-type Gag protein, but be unable to contribute to increased HIV-1 production. This modification should result in safer vectors for immunotherapy and immunophrophylaxis.

EXAMPLE 10

Inhibition of HIV-1 Expression Using Transdominant (TD)-TD-Gag-TD Rev or Td Gap-Pro-TD Rev Genes Direct injection of DNA or use of vectors other than retroviral vectors will allow the constitutive high level of trans-dominant Gag (TDgag) in cells. In addition, the approach taken by B. K. Felber et al., *Science* 239:184–187 (1988) will allow the generation of retroviral vectors, e.g. mouse-derived retroviral vectors, encoding HIV-1 TDgag, which will not interfere with the infection of human cells by the retroviral vectors. In the approach of Felber, et al., supra, it was shown that fragments of the HIV-1 LTR containing the promoter and part of the polyA signal can be incorporated without detrimental effects within mouse retroviral vectors and remain transcriptionally silent. The presence of Tat protein stimulated transcription from the HIV-1 LTR and resulted in the high level expression of genes linked to the HIV-1 LTR.

The generation of hybrid TDgag-TDRev or TDgag-pro-TDRev genes and the introduction of expression vectors in human cells will allow the efficient production of two proteins that will inhibit HIV-1 expression. The incorporation of two TD proteins in the same vector is expected to amplify the effects of each one on viral replication. The use of the HIV-1 promoter in a matter similar to one described in B. K. Felber, et al., supra, will allow high level Gag and Rev expression in infected cells. In the absence of infection, expression will be substantially lower. Alternatively, the use of other strong promoters will allow the constitutive expression of such proteins. This approach could be highly beneficial, because of the production of a highly immunogenic gag, which is not able to participate in the production of infectious virus, but which, in fact, antagonizes such production. This can be used as an efficient immuniprophylactic or immunotherapeutic approach against AIDS.

Examples of trans-dominant mutants are described in Trono et al., *Cell* 59:112–120 (1989).

1. Generation of Constructs Encoding Transdominant Gag Mutant Proteins

Gag mutant proteins that can act as trans-dominant mutants, as described, for example, in Trono et al., supra, will be generated by modifying vector p37M1-10OD or p55M1-13P0 to produce transdominant Gag proteins at high constitutive levels.

The transdominant Gag protein will stimulate the immune system and will inhibit the production of infectious virus, but will not contribute to the production of infectious virus.

The added safety of this approach makes it more acceptable for human application.

VII. REFERENCES

U.S. Pat. No. 6,174,666 issued Jan. 16, 2001 (Pavlakis and Felber)

U.S. Pat. No. 5,972,596 issued Oct. 26, 1999 (Pavlakis and Felber)

U.S. Pat. No. 5,965,726 issued Oct. 12, 1999 (Pavlakis and Felber)

WO 98/17816 Lentiviral Vectors (Kingsman & Kingsman) (Oxford Biomedica Ltd)

WO 98/34640 (Shiver, J. W., Davies, M-E M., Freed, D. C., Liu, M. A. and Perry, H. C. -Merck & Co., Inc.)

WO 98/46083 Use of Lentiviral Vectors for Antigen Presentation in Dendritic Cells (Wong-Staal, Li; Kan-Mitchell) (Univ. of Cal.)

WO 99/04026 Lentiviral Vectors (Chen, Gasmi, Yee and Jolly) (Chiron)

WO 99/15641 Non-Primate Lentiviral Vectors and Packaging Systems (Poeschia, Looney and Wong-Staal) (Univ. of Cal.)

WO 99/30742 Therapeutic Use of Lentiviral Vectors (Naldini and Song)

WO 99/51754 Infectious Pseudotyped Lentiviral Vectors Lacking Matrix Protein and Uses Thereof (Goettlinger, Reil and Bukovsky) (Dana Farber Cancer Inst Inc)

PCT/US99/11082 Post-Transcriptional Regulatory Elements and Uses Thereof (Pavlakis and Nappi), filed May 22, 1999, published as WO 99/61596 on Dec. 2, 1999

Akkina, R. K., Walton, R. W., Chen, M. L., Li, Q-X, Planelles, V and Chen, I. S. Y., "High-efficiency gene transfer into CD34[+] cells with a human immunodeficiency virus type 1-based retroviral vector pseudotyped with vesicular stomatitis virus envelope glycoprotein G," *J. Virol.* 70:2581–2585 (1996)

Amado, R. G. & Chen, I. S. Y., "Letinviral vectors-the promise of gene therapy within reach?," *Science* 285:674–676 (July 1999)

Donahue, R. E., An, D. S., Wersto, R. P., Agricola, B. A., Metzger, M. E. and Chen, I. S. Y., "Transplantation of immunoselected CD34[+] cells transduced with a EGFP-expressing lentiviral vector in non-human primates," *Blood* 92(suppl. 1):383b, Abstract #4648.5 (1998)

Fox, J. L., "Researchers wary of fear-based ban on lentivirus gene therapy," *Nature Biotechnology* 16:407–408 (1998)

Goldman, M. J., Lee, P. S., Yang, J. S. & Wilson, J. M., "Lentiviral vectors for gene therapy of cystic fibrosis," *Hum Gene Ther.* 8, 2261–2268 (1997)

Hartikka J, Sawdey M, Cornefert-Jensen F, Margalith M, Barnhart K, Nolasco M, Vahlsing H L, Meek J, Marquet M, Hobart P, Norman J, and Manthorpe M., "An improved plasmid DNA expression vector for direct injection into skeletal muscle," *Hum Gene Ther.* 7:1205–17 (1996)

Kafri, T., Blomer, U., Peterson, D. A., Gage, F. H. & Verma, I. M., "Sustained expression of genes delivered directly into liver and muscle by lentiviral vectors," *Nat Genet.* 17, 314–317 (1997)

Kafri, T., van Praag, H., Ouyang, L., Gage, F. G. and Verma, I. M., "A packaging cell line for lentivirus vectors," *J. Virol.* 73:576–584 (1999)

Kim, V. N., Mitrophanous, K., Kingsman, S. M., and Kingsman, A. J., "Minimal Requirement for a Lentivirus Vector Based on Human Immunodeficiency Virus Type 1", *J. Virol.* 72:811–816 (1998)

Klimatcheva, E., Rosenblatt, J. D. and Planelles, V., "Lentiviral vectors and gene therapy," *Frontiers in Bioscience* 4:d481–496 (June 1999)

Miyoshi, H., Takahashi, M., Gage, F. H. & Verma, I. M., "Stable and efficient gene transfer into the retina using an HIV-based lentiviral vector," *Proc Natl Acad Sci USA.* 94: 10319–10323 (1997)

Miyoshi, H., Blomer,U., Takahashi, M., Gage, F. H., and Verma, I. M., "Development of self-inactivating lentivirus vector," *J. Virol.* 72:8150–8157 (1998)

Miyoshi, H., Smith, K. A., Mosier, D. E., Verma, I. M. and Torbett, B. E., "Transduction of human CD34[+] cells that mediate long-term engraftment of NOD/SCID mice by HIV vectors," *Science* 283:682–686 (1999)

Naldini, L., Blomer, U., Gallay, P., Ory, D., Mulligan, R., Gage, F. H., Verma, I. M. & Trono, D., "In vivo gene delivery and stable transduction of nondividing cells by a lentiviral vector," *Science.* 272, 263–267 (1996)

Naviaux, R. K, Costanzi, E., Haas, M. and Verma, I., "The pCL vector system: rapid production of helper-free, high-titer, recombinant retroviruses," *J Virol.* 70:5701–5705 (1996)

Pavlakis, G. N., Schneider, R.; Song, S., Nasioulas, G., Zolotukhin, A., Felber, B. K., Trauger, R., Cox, J., and Manthorpe, M., "Use of simple Rev-independent HIV-1 gag expression vectors in gene therapy and gene vaccine applications," *Natl Conf Hum Retroviruses Relat Infect* (2nd), Jan. 29–Feb. 2,(1995); 91.

Poeschla, E. M., Wong-Staal, F. & Looney, D. J., "Efficient transduction of nondividing human cells by feline immunodeficiency virus lentiviral vectors," *Nature Med.* 4:354–357 (1998)

Qiu, J. T., R. Song, M. Dettenhofer, C. Tian, T. August, B. K. Felber, G. N. Pavlakis and X. F. Yu, "Evaluation of novel human immunodeficiency virus type 1 Gag DNA vaccines for protein expression in mammalian cells and induction of immune responses," J. *Virol.* 73: 9145–52 (Nov. 1999)

Reynolds, P. N. and Curiel, D. T., "Viral vectors show promise in Colorado," *Nature Biotechnology* 16:422423 (1998)

Schneider, R., Campbell, M., Nasioulas, G., Felber, B. K., and Pavlakis, G. N., Inactivation of the human immunodeficiency virus type 1 inhibitory elements allows Rev-independent expression of Gag and Gag/protease and particle formation, "*J. Virol.* 71:4892–4903 (1997)

Schwartz, S., M. Campbell, G. Nasioulas, J. Harrison, B. K. Felber and G. N. Pavlakis, "Mutational inactivation of an inhibitory sequence in human immunodeficiency virus type-1 results in Rev-independent gag expression," *J. Virol.* 66:7176–7182 (1992)

Shiver, J. W., Yasutomi, Y., Free, D. C., Davies, M.-E., Perry, H. C., Pavlakis, G. N., Letvin, N. L., and Liu, M. A., "DNA Vaccine-Mediated Cellular Immunity Against HIV-1 gag and env", presented at the Conference on Advances in AIDS Vaccine Development: 8[th] Annual Meeting of the National Cooperative Vaccine Development Groups for AIDS (NCVDGs) from Feb. 11–15, 1996.

Soneoka, Y., Cannon, P. M., Ransdale, E. E., Griffiths, J. C., Romano, G., Kingsman, S. M. and Kingsman, A. J., "A transient three-plasmid expression system for the production of high titer retroviral vectors," *Nuc. Acids Res.* 23:628–633 (1995).

Srinivasakumar, N., Chazal, N., Helga-Maria, C., Prasad, S., Hammarskjöld, M.-L., and Rekosh, D., "The Effect of Viral Regulatory Protein Expression on Gene Delivery by Human Immunodeficiency Virus Type 1 Vectors Produced in Stable Packaging Cell Lines," *J. Virol.*, 71:5841–5848 (1997)

Sutton, R. E., Wu, H. T., Rigg, R., Bohnlein, E. & Brown, P. O., "Human immunodeficiency virus type 1 vectors efficiently transduce human hematopoietic stem cells," *J. Virol.* 72, 5781–5788 (1998)

Tabemero, C., A. S. Zolotukhin, J. Bear, R. Schneider, G. Karsenty and B. K. Felber, "Identification of an RNA sequence within an intracisternal-A particle element able to replace Rev-mediated posttranscriptional regulation of human immunodeficiency virus type 1," *J. Virol.* 71:95–101 (1997). (see also my email message)

Takahashi, M.; Miyoshi, H.; Verma, I. M.; Gage, F. H., "Rescue from photoreceptor degeneration in the rd mouse by human immunodeficiency virus vector-mediated gene transfer," *J. Virol.* 73: 7812–7816 (September 1999)

Uchida, N., Sutton, R. E., Friera, A. M., He, D., Reitsma, M. J., Chang, W. C., Veres, G., Scollay, R. & Weissman, I. L., "HIV, but not murine leukemia virus, vectors mediate high efficiency gene transfer into freshly isolated G0/G1 human hematopoietic stem cells," *Proc. Natl Acad. Sci. USA.* 95, 11939–11944 (1998)

Valentin, A., W. Lu, M. Rosati, R. Schneider, J. Albert, A. Karlsson and G. N. Pavlakis. "Dual effect of interleukin 4 on HIV-1 expression: Implications for viral phenotypic switch and disease progression," *Proc. Natl Acad. Sci. USA.* 95: 8886–91 (1998)

White, S. M., Renda, M, Nam, N-Y, Klimatcheva, E., Hu, Y, Fisk, J, Halterman, M, Rimel, B. J., Federoff, H, Pandya, S., Rosenblatt, J. D. and Planelles, V, "Lentivirus vectors using human and simian immunodeficiency virus elements," *J Virol.* 73:2832–2840 (April 1999)

Wolff, J. A. and Trubetskoy, V. S., "The Cambrian period of nonviral gene delivery," *Nature Biotechnology* 16:421–422 (1998)

Zolotukhin, J., Valentin, A., Pavlakis, G. N. and Felber, B. K. "Continuous propagation of RRE(-)and Rev(-)RRE (-) human immunodeficiency virus type 1 molecular clones containing a cis-acting element of Simian retrovirus type 1 in human peripheral blood lymphocytes," *J. Virol.* 68:7944–7952 (1994)

Zufferey, R., Nagy, D. Mandel, R. J., Naldini, L. and Trono, D., "Multiply Attenuated Lentiviral Vector Achieves Efficient Gene-Delivery In Vivo", *Nature Biotechnology* 15:871–875 (1997)

Zufferey, R., Dull, T., Mandel. R. J., Bukovsky, A., Quiroz, D., Naldini, L. & Trono, D., "Self-inactivating lentivirus vector for safe and efficient in vivo gene delivery," *J. Virol.* 72:9873–9880 (1998)

Those skilled in the art will recognize that any gene encoding a mRNA containing an inhibitory/instability sequence or sequences can be modified in accordance with the exemplified methods of this invention or their functional equivalents.

Modifications of the above described modes for carrying out the invention that are obvious to those of skill in the fields of genetic engineering, virology, immunology, medicine, and related fields are intended to be within the scope of the following claims.

Every reference cited hereinbefore throughout the application is hereby incorporated by reference in its entirety.

SEQUENCE LISTING

```
<160> NUMBER OF SEQ ID NOS: 19

<210> SEQ ID NO 1
<211> LENGTH: 4338
<212> TYPE: DNA
<213> ORGANISM: Artificial Sequence
<220> FEATURE:
<223> OTHER INFORMATION: Description of Artificial Sequence:  Mutated
      Human Immunodeficiency Virus - 1 Gag/Pol gene

<400> SEQUENCE: 1
atgggtgcga gagcgtcagt attaagcggg ggagaattag atcgatggga aaaaattcgg      60
ttaaggccag ggggaaagaa gtacaagcta aagcacatcg tatgggcaag cagggagcta     120
gaacgattcg cagttaatcc tggcctgtta gaaacatcag aaggctgtag acaaatactg     180
```

```
ggacagctac aaccatccct tcagacagga tcagaggagc ttcgatcact atacaacaca    240
gtagcaaccc tctattgtgt gcaccagcgg atcgagatca aggacaccaa ggaagcttta    300
gacaagatag aggaagagca aaacaagtcc aagaagaagg cccagcaggc agcagctgac    360
acaggacaca gcaatcaggt cagccaaaat taccctatag tgcagaacat ccaggggcaa    420
atggtacatc aggccatatc acctagaact ttaaatgcat gggtaaaagt agtagaagag    480
aaggctttca gcccagaagt gatacccatg ttttcagcat tatcagaagg agccacccca    540
caggacctga cacgatgtt gaacaccgtg gggggacatc aagcagccat gcaaatgtta    600
aaagagacca tcaatgagga agctgcagaa tgggatagag tgcatccagt gcatgcaggg    660
cctattgcac caggccagat gagagaacca aggggaagtg acatagcagg aactactagt    720
acccttcagg aacaaatagg atggatgaca ataatccac ctatcccagt aggagagatc    780
tacaagaggt ggataatcct gggattgaac aagatcgtga ggatgtatag ccctaccagc    840
attctggaca taagacaagg accaaaggaa ccctttagag actatgtaga ccggttctat    900
aaaactctaa gagctgagca agcttcacag gaggtaaaaa attggatgac agaaaccttg    960
ttggtccaaa atgcgaaccc agattgtaag accatcctga aggctctcgg cccagcggct   1020
acactagaag aaatgatgac agcatgtcag ggagtaggag gacccggcca taaggcaaga   1080
gttttggccg aggcgatgag ccaggtgacg aactcggcga ccataatgat gcagagaggc   1140
aacttccgga accagcggaa gatcgtcaag tgcttcaatt gtggcaaaga agggcacacc   1200
gccaggaact gccgggcccc ccggaagaag ggctgttgga aatgtggaaa ggaaggacac   1260
caaatgaaag attgtactga gagacaggct aatttttag ggaagatctg gccttcctac   1320
aagggaaggc cagggaattt tcttcagagc agaccagagc caacagcccc accagaagag   1380
agcttcaggt ctgggtaga acaacaact ccccctcaga agcaggagcc gatagacaag   1440
gaactgtatc ctttaacttc cctcagatca ctctttggca acgacccctc gtcacagtaa   1500
ggatcggggg gcaactcaag gaagcgctgc tcgatacagg agcagatgat acagtattag   1560
aagaaatgag tttgccagga agatggaaac caaaaatgat agggggatc ggggcttca   1620 tcaaggtgag gcagtacgac cagatactca tagaaatctg tggacataaa gctataggta   1680
cagtattagt aggacctacc tacacctgtc aacataattg gaagaaatct gttgacccag   1740
atcggctgca ccttgaactt ccccatcagc cctattgaga cggtgcccgt gaagttgaag   1800
ccggggatgg acgcccccaa ggtcaagcaa tggccattga cgaaagagaa gatcaaggcc   1860
ttagtcgaaa tctgtacaga gatggagaag gaaggaaga tcagcaagat cgggcctgag   1920 aaccccctaca cactccagt cttcgcaatc aagaagaagg acagtaccaa gtggagaaag   1980
ctggtggact tcagagagct gaacaagaga actcaggact tctgggaagt tcagctgggc   2040
atcccacatc ccgctgggtt gaagaagaag aagtcagtga cagtgctgga tgtgggtgat   2100
gcctacttct ccgttccctt ggacgaggac ttcaggaagt acactgcctt cacgatacct   2160
agcatcaaca cgagacacc aggcatccgc taccagtaca acgtgctgcc acagggatgg   2220
aagggatcac cagccatctt tcaaagcagc atgaccaaga tcctggagcc cttccgcaag   2280
caaaacccag acatcgtgat ctatcagtac atggacgacc tctacgtagg aagtgacctg   2340
gagatcgggg cagcacagga ccaagatcga ggagctgaga cagcatctgt tgaggtgggg   2400
actgaccaca ccagacaaga agcaccagaa ggaacctccc ttcctgtgga tgggctacga   2460
actgcatcct gacaagtgga cagtgcagcc catcgtgctg cctgagaagg acagctggac   2520
```

-continued

```
tgtgaacgac atacagaagc tcgtgggcaa gttgaactgg gcaagccaga tctacccagg      2580
catcaaagtt aggcagctgt gcaagctgct tcgaggaacc aaggcactga cagaagtgat      2640
cccactgaca gaggaagcag agctagaact ggcagagaac cgagagatcc tgaaggagcc      2700
agtacatgga gtgtactacg acccaagcaa ggacctgatc gcagagatcc agaagcaggg      2760
gcaaggccaa tggacctacc aaatctacca ggagcccttc aagaacctga agacaggcaa      2820
gtacgcaagg atgagggggtg cccacaccaa cgatgtgaag cagctgacag aggcagtgca      2880
gaagatcacc acagagagca tcgtgatctg gggcaagact cccaagttca agctgcccat      2940
acagaaggag acatgggaga catggtggac cgagtactgg caagccacct ggatccctga      3000
gtgggagttc gtgaacaccc ctcccttggt gaaactgtgg tatcagctgg agaaggaacc      3060
catcgtggga gcagagacct tctacgtgga tgggcagcc aacagggaga ccaagctggg      3120
caaggcaggc tacgtgacca accgaggacg acagaaagtg gtgaccctga ctgacaccac      3180
caaccagaag actgagctgc aagccatcta cctagctctg caagacagcg gactggaagt      3240
gaacatcgtg acagactcac agtacgcatg ggcatcatcc aagcacaacc agaccaatcc      3300
gagtcagagc tggtgaacca gatcatcgag cagctgatca agaaggagaa agtgtacctg      3360
gcatgggtac cagcacacaa aggaattgga ggaaatgaac aagtagataa attagtcagt      3420
gctgggatcc ggaaggtgct gttcctggac gggatcgata aggcccaaga tgaacatgag      3480
aagtaccact ccaactggcg cgctatggcc agcgacttca acctgccacc tgtagtagca      3540
aaagaaatag tagccagctg tgataaatgt cagctaaaag gagaagccat gcatggacaa      3600
gtagactgta gtccaggaat atggcagctg gactgcacgc acctggaggg gaaggtgatc      3660
ctggtagcag ttcatgtagc cagtggatat atagaagcag aagttatccc tgctgaaact      3720
gggcaggaaa cagcatattt tctttaaaa ttagcaggaa gatggccagt aaaaacaata      3780
cacacggaca acgaagcaa cttcactggt gctacggtta aggccgcctg ttggtgggcg      3840
ggaatcaagc aggaatttgg aattccctac aatccccaat cgcaaggagt cgtggagagc      3900
atgaacaagg agctgaagaa gatcatcgga cagtgaggga tcaggctgag cacctgaaga      3960
cagcagtgca gatggcagtg ttcatccaca acttcaaaag aaaagggggg attgggggggt      4020 acagtgcagg ggaaaggatc gtggacatca tcgccaccga catccaaacc aaggagctgc      4080
agaagcagat caccaagatc cagaacttcc gggtgtacta ccgcgacagc cgcaacccac      4140
tgtggaaggg accagcaaag ctcctctgga agggagaggg ggcagtggtg atccaggaca      4200
acagtgacat caaagtggtg ccaaggcgca aggccaagat catccgcgac tatggaaaac      4260
agatggcagg tgatgattgt gtggcaagta gacaggatga ggattagaac ctggaagagc      4320
ctggtgaagc accatatg                                                    4338
```

<210> SEQ ID NO 2
<211> LENGTH: 2507
<212> TYPE: DNA
<213> ORGANISM: Human immunodeficiency virus type 1

<400> SEQUENCE: 2

```
tgtacagaga tggaaaagga agggaaaatt tcaaaaattg ggcctgaaaa tccatacaat        60
actccagtat ttgccataaa gaaaaagac agtactaaat ggagaaaatt agtagatttc       120
agagaactta taagagaac tcaagacttc tgggaagttc aattaggaat accacatccc       180
gcagggttaa aaagaaaaa atcagtaaca gtactggatg tgggtgatgc atatttttca       240
gttcccttag atgaagactt caggaaatat actgcattta ccatacctag tataaacaat       300
```

```
gagacaccag ggattagata ccatacctag tataaacaat gagacaccag ggatttgata    360
tcagtacaat gtgcttccac agggatggaa aggatcacca gcaatattcc aaagtagcat    420
gacaaaaatc ttagagcctt ttagaaaaca aaatccagac atagttatct atcaatacat    480
ggatgatttg tatgtaggat ctgacttaga aataggcag catagaacaa aaatagagga    540
gctgagacaa catctgttga ggtggggact taccacacca gacaaaaaac atcagaaaga    600
acctccattc ctttggatgg gttatgaact ccatcctgat aaatggacag tacagcctat    660
agtgctgcca gaaaaagaca gctggactgt caatgacata cagaagttag tggggaaatt    720
gaattgggca agtcagattt acccagggat taaagtaagg caattatgta aactccttag    780
aggaaccaaa gcactaacag aagtaatacc actaacagaa gaagcagagc tagaactggc    840
agaaaacaga gagattctaa aagaaccagt acatggagtg tattatgacc catcaaaaga    900
cttaatagca gaaatacaga agcaggggca aggccaatgg acatatcaaa tttatcaaga    960
gccatttaaa aatctgaaaa caggaaaata tgcaagaatg agggtgccc acactaatga    1020 tgtaaaacaa ttaacagagg cagtgcaaaa ataaccaca gaaagcatag taatatgggg    1080
aaagactcct aaatttaaac tgcccataca aaggaaaaca tgggaaacat ggtggacaga    1140
gtattggcaa gccacctgga ttcctgagtg ggagtttgtt aatacccctc ctttagtgaa    1200
attatggtac cagttagaga aagaacccat agtaggagca gaaaccttct atgtagatgg    1260
ggcagctaac agggagacta aattaggaaa agcaggatat gttactaata gaggaagaca    1320
aaaagttgtc accctaactg acacaacaaa tcagaagact gagttacaag caatttatct    1380
agctttgcag gattcgggat tagaagtaaa catagtaaca gactcacaat atgcattagg    1440
aatcattcaa gcacaaccag atcaaagtga atcagagtta gtcaatcaaa taatagagca    1500
gttaataaaa aaggaaaagg tctatctggc atgggtacca gcacacaaag gaattggagg    1560
aaatgaacaa gtagataaat tagtcagtgc tggaatcagg aaagtactat ttttagatgg    1620
aatagataag gcccaagatg aacatgagaa atatcacagt aattggagag caatggctag    1680
tgattttaac ctgccacctg tagtagcaaa agaaatagta gccagctgtg ataaatgtca    1740
gctaaaagga gaagccatgc atggacaagt agactgtagt ccaggaatat ggcaactaga    1800
ttgtacacat ttagaaggaa aagttatcct ggtagcagtt catgtagcca gtggatatat    1860
agaagcagaa gttattccag cagaaacagg gcaggaaaca gcatattttc ttttaaaatt    1920
agcaggaaga tggccagtaa aaacaataca tacagacaat ggcagcaatt tcaccagtgc    1980
tacggttaag gccgcctgtt ggtgggcggg aatcaagcag gaatttggaa ttccctacaa    2040
tccccaaagt caaggagtag tagaatctat gaataaagaa ttaagaaaaa ttataggaca    2100
ggtaagagat caggctgaac atcttaagac agcagtacaa atggcagtat tcatccacaa    2160
ttttaaaaga aagggggga ttggggggta cagtgcaggg gaaagaatag tagacataat    2220
agcaacagac atacaaacta aagaattaca aaacaaatt acaaaaattc aaaattttcg    2280
ggtttattac agggacagca gaaatccact ttggaaagga ccagcaaagc tcctctggaa    2340
aggtgaaggg gcagtagtaa tacaagataa tagtgacata aaagtagtgc caagaagaaa    2400
agcaaagatc attagggatt atggaaaaca gatggcaggt gatgattgtg tggcaagtag    2460
acaggatgag gattagaaca tggaaaagtt tagtaaaaca ccatatg                  2507
```

<210> SEQ ID NO 3
<211> LENGTH: 2467
<212> TYPE: DNA

<213> ORGANISM: Artificial Sequence
<220> FEATURE:
<223> OTHER INFORMATION: Description of Artificial Sequence: Mutated
    Human Immunodeficiency Virus - 1 Pol gene

<400> SEQUENCE: 3

```
tgtacagaga tgggaagga agggaagatc agcaagatcg ggcctgagaa cccctacaac      60
actccagtct tcgcaatcaa gaagaaggac agtaccaagt ggagaaagct ggtggacttc    120
agagagctga acaagagaac tcaggacttc tgggaagttc agctgggcat cccacatccc    180
gctgggttga agaagaagaa gtcagtgaca gtgctggatg tgggtgatgc ctacttctcc    240
gttcccttgg acgaggactt caggaagtac actgccttca cgatacctag catcaacaac    300
gagacaccag gcatccgcta ccagtacaac gtgctgccac agggatggaa gggatcacca    360
gccatctttc aaagcagcat gaccaagatc ctggagccct ccgcaagca aaacccagac    420
atcgtgatct atcagtacat ggacgacctc tacgtaggaa gtgacctgga gatcgggcag    480
cacaggacca agatcgagga gctgagacag catctgttga ggtggggact gaccacacca    540
gacaagaagc accagaagga acctcccttc ctgtggatgg gctacgaact gcatcctgac    600
aagtggacag tgcagcccat cgtgctgcct gagaaggaca gctggactgt gaacgacata    660
cagaagctcg tgggcaagtt gaactgggca agccagatct acccaggcat caaagttagg    720
cagctgtgca agctgcttcg aggaaccaag gcactgacag aagtgatccc actgacagag    780
gaagcagagc tagaactggc agagaaccga gagatcctga aggagccagt acatggagtg    840
tactacgacc caagcaagga cctgatcgca gagatccaga agcaggggca aggccaatgg    900
acctaccaaa tctaccagga gcccttcaag aacctgaaga caggcaagta cgcaaggatg    960
aggggtgccc acaccaacga tgtgaagcag ctgacagagg cagtgcagaa gatcaccaca   1020
gagagcatcg tgatctgggg caagactccc aagttcaagc tgcccataca aggagacat   1080
tgggagacat ggtggaccga gtactggcaa gccacctgga tccctgagtg ggagttcgtg   1140
aacaccctc ccttggtgaa actgtggtat cagctggaga aggaacccat cgtgggagca   1200
gagaccttct acgtggatgg ggcagccaac agggagacca agctgggcaa ggcaggctac   1260
gtgaccaacc gaggacgaca gaaagtggtg accctgactg acaccaccaa ccagaagact   1320
gagctgcaag ccatctacct agctctgcaa gacagcggac tggaagtgaa catcgtgaca   1380
gactcacagt acgcactggg catcatccaa gcacaaccag accatccga gtcagagctg   1440
gtgaaccaga tcatcgagca gctgatcaag aaggagaaag tgtacctggc atgggtacca   1500
gcacacaaag gaattggagg aaatgaacaa gtagataaat tagtcagtgc tgggatccgg   1560
aaggtgctgt tcctggacgg gatcgataag gcccaagatg aacatgagaa gtaccactcc   1620
aactggcgcg ctatggccag cgacttcaac ctgccacctg tagtagcaaa agaaatagta   1680
gccagctgtg ataaatgtca gctaaaagga gaagccatgc atggacaagt agactgtagt   1740
ccaggaatat ggcagctgga ctgcacgcac ctggagggga aggtgatcct ggtagcagtt   1800
catgtagcca gtggatatat agaagcagaa gttatccctg ctgaaactgg gcaggaaaca   1860
gcatattttc ttttaaaatt agcaggaaga tggccagtaa aaacaataca cacggacaac   1920
ggaagcaact tcactggtgc tacggttaag gccgcctgtt ggtgggcggg aatcaagcag   1980
gaatttggaa ttccctacaa tccccaatcg caaggagtcg tggagagcat gaacaaggag   2040
ctgaagaaga tcatcggaca gtgagggat caggctgagc acctgaagac agcagtgcag   2100
atggcagtgt tcatccacaa cttcaaaaga aagggggga ttggggggta cagtgcaggg   2160
```

-continued gaaaggatcg tggacatcat cgccaccgac atccaaacca aggagctgca gaagcagatc 2220
accaagatcc agaacttccg ggtgtactac cgcgacagcc gcaacccact gtggaaggga 2280
ccagcaaagc tcctctggaa gggagagggg gcagtggtga tccaggacaa cagtgacatc 2340
aaagtggtgc caaggcgcaa ggccaagatc atccgcgact atggaaaaca gatggcaggt 2400
gatgattgtg tggcaagtag acaggatgag gattagaacc tggaagagcc tggtgaagca 2460
ccatatg 2467

<210> SEQ ID NO 4
<211> LENGTH: 1533
<212> TYPE: DNA
<213> ORGANISM: Artificial Sequence
<220> FEATURE:
<223> OTHER INFORMATION: Description of Artificial Sequence: Mutated Simian Immunodeficiency Virus Gag gene

<400> SEQUENCE: 4
atgggcgtga gaaactccgt cttgtcaggg aagaaagcag atgaattaga aaaaattagg 60
ctacgaccca acggaaagaa aaagtacatg ttgaagcatg tagtatgggc agcaaatgaa 120
ttagatagat ttggattagc agaaagcctg ttggagaaca aagaaggatg tcaaaaaata 180
ctttcggtct tagctccatt agtgccaaca ggctcagaaa atttaaaaag cctttataat 240
actgtctgcg tcatctggtg cattcacgca gaagagaaag tgaaacacac tgaggaagca 300
aaacagatag tgcagagaca cctagtggtg gaaacaggaa ccaccgaaac catgccgaag 360
acctctcgac caacagcacc atctagcggc agaggaggaa actacccagt acagcagatc 420
ggtggtaact acgtccacct gccactgtcc ccgagaaccc tgaacgcttg ggtcaagctg 480
atcgaggaga agaagttcgg agcagaagta gtgccaggat tccaggcact gtcagaaggt 540 tgcacccccct acgacatcaa ccagatgctg aactgcgttg gagaccatca ggcggctatg 600
cagatcatcc gtgacatcat caacgaggag gctgcagatt gggacttgca gcacccacaa 660
ccagctccac aacaaggaca acttagggag ccgtcaggat cagacatcgc aggaaccacc 720
tcctcagttg acgaacagat ccagtggatg taccgtcagc agaacccgat cccagtaggc 780
aacatctacc gtcgatggat ccagctgggt ctgcagaagt gcgtccgtat gtacaacccg 840
accaacattc tagatgtaaa acaagggcca aaagagccat ttcagagcta tgtagacagg 900
ttctacaaaa gtttaagagc agaacagaca gatgcagcag taaagaattg gatgactcaa 960
acactgctga ttcaaaatgc taacccagat tgcaagctag tgctgaaggg gctgggtgtg 1020
aatcccaccc tagaagaaat gctgacggct tgtcaaggag taggggggcc gggacagaag 1080
gctagattaa tggcagaagc cctgaaagag gccctcgcac cagtgccaat cccttttgca 1140
gcagcccaac agaggggacc aagaaagcca attaagtgtt ggaattgtgg gaaagaggga 1200
cactctgcaa ggcaatgcag agccccaaga agacagggat gctggaaatg tggaaaaatg 1260
gaccatgtta tggccaaatg cccagacaga caggcgggtt ttttaggcct tggtccatgg 1320
ggaaagaagc ccgcaatttt ccccatggct caagtgcatc aggggctgat gccaactgct 1380
cccccagagg acccagctgt ggatctgcta aagaactaca tgcagttggg caagcagcag 1440
agagaaaagc agagagaaag cagagagaag ccttacaagg aggtgacaga ggatttgctg 1500
cacctcaatt ctctctttgg aggagaccag tag 1533

<210> SEQ ID NO 5
<211> LENGTH: 1532
<212> TYPE: DNA

<210> SEQ ID NO 5
<211> LENGTH: 1532
<212> TYPE: DNA
<213> ORGANISM: Artificial Sequence
<220> FEATURE:
<223> OTHER INFORMATION: Description of Artificial Sequence: Consensus sequence of mutated Simian Immunodeficiency Virus Gag gene (SIVgagDX) with wild-type SIV 239 Gag gene

<400> SEQUENCE: 5

```
atgggcgtga gaaactccgt cttgtcaggg aagaaagcag atgaattaga aaaattagg      60
ctacgaccca acggaaagaa aaagtacatg ttgaagcatg tagtatgggc agcaaatgaa     120
ttagatagat ttggattagc agaaagcctg ttggagaaca agaaggatg tcaaaaaata      180
ctttcggtct tagctccatt agtgccaaca ggctcagaaa atttaaaaag cctttataat     240
actgtctgcg tcatctggtg cattcacgca aagagaaag tgaaacacac tgaggaagca      300
aaacagatag tgcagagaca cctagtggtg aaacaggaa cmacmgaaac yatgccraar     360
acmwstmgac caacagcacc atctagcggc agaggaggaa aytacccagt acarcaratm     420
ggtggtaact aygtccacct gccaytrwsc ccgagaacmy traaygcytg ggtmaarytg     480
atmgaggara agaarttygg agcagaagta gtgccaggat tycaggcact gtcagaaggt     540
tgcacccct aygacatyaa ycagatgytr aaytgygtkg agaccatca rgcggctatg     600
cagatyatcm gwgayatyat maacgaggag gctgcagatg ggacttgcag cacccacaac     660
cagctccaca caaggacaa cttagggagc cgtcaggatc agayatygca ggaacmacyw     720
sytcagtwga ygaacaratc cagtggatgt acmgwcarca gaacccsatm ccagtaggca     780
acatytacmg kmgatggatc carctgggky tgcaraartg ygtymgwatg tayaacccra     840
cmaacattct agatgtaaaa caagggccaa aagagccatt tcagagctat gtagacaggt     900
tctacaaaag tttaagagca gaacagacag atgcagcagt aaagaattgg atgactcaaa     960
cactgctgat tcaaaatgct aacccagatt gcaagctagt gctgaagggg ctgggtgtga    1020
atcccaccct agaagaaatg ctgacggctt gtcaaggagt aggggggccg ggacagaagg    1080
ctagattaat ggcagaagcc ctgaaagagg ccctcgcacc agtgccaatc ccttttgcag    1140
cagcccaaca gagggaccaa gaaaagccaa ttaagtgttg gaattgtggg aaagagggac    1200
actctgcaag gcaatgcaga gccccaagaa gacagggatg ctggaaatgt ggaaaaatgg    1260
accatgttat ggccaaatgc ccagacagac aggcgggttt tttaggcctt ggtccatggg    1320
gaaagaagcc ccgcaatttc cccatggctc aagtgcatca ggggctgatg ccaactgctc    1380
ccccagagga cccagctgtg gatctgctaa agaactacat gcagttgggc aagcagcaga    1440
gagaaaagca gagagaaagc agagagaagc cttacaagga ggtgacagag gatttgctgc    1500
acctcaattc tctctttgga ggagaccagt ag                                   1532
```

<210> SEQ ID NO 6
<211> LENGTH: 8366
<212> TYPE: DNA
<213> ORGANISM: Artificial Sequence
<220> FEATURE:
<223> OTHER INFORMATION: Description of Artificial Sequence: DNA sequence of the construct pCMVgagpolBNKan containing a CMV promoter, a HIV gag/pol gene and a kanamycin resistance gene

<400> SEQUENCE: 6

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
```

-continued

```
cgcctggctg accgcccaac gacccccgcc cattgacgtc aataatgacg tatgttccca      240
tagtaacgcc aatagggact ttccattgac gtcaatgggt ggagtattta cggtaaactg      300
cccacttggc agtacatcaa gtgtatcata tgccaagtac gccccctatt gacgtcaatg      360
acggtaaatg cccgcctgg cattatgccc agtacatgac cttatgggac tttcctactt      420
ggcagtacat ctacgtatta gtcatcgcta ttaccatggt gatgcggttt tggcagtaca      480
tcaatgggcg tggatagcgg tttgactcac ggggatttcc aagtctccac cccattgacg      540
tcaatgggag tttgttttgg caccaaaatc aacgggactt tccaaaatgt cgtaacaact      600 ccgcccatt gacgcaaatg gcggtaggc gtgtacggtg ggaggtctat ataagcagag       660
ctcgtttagt gaaccgtcag atcgcctgga gacgccatcc acgctgtttt gacctccata      720
gaagacaccg ggaccgatcc agcctccgcg gccgcgcgtc gacagagaga tgggtgcgag      780
agcgtcagta ttaagcgggg gagaattaga tcgatgggaa aaaattcggt taaggccagg      840 gggaagaag aagtacaagc taaagcacat cgtatgggca agcagggagc tagaacgatt       900
cgcagttaat cctggcctgt tagaaacatc agaaggctgt agacaaatac tgggacagct      960
acaaccatcc cttcagacag gatcagagga gcttcgatca ctatacaaca cagtagcaac     1020
cctctattgt gtgcaccagc ggatcgagat caaggacacc aaggaagctt tagacaagat     1080
agaggaagag caaaacaagt ccaagaagaa ggcccagcag gcagcagctg acacaggaca     1140
cagcaatcag gtcagccaaa attaccctat agtgcagaac atccagggc aaatggtaca      1200 tcaggccata tcacctagaa ctttaaatgc atgggtaaaa gtagtagaag agaaggcttt     1260
cagcccagaa gtgatacccca tgttttcagc attatcagaa ggagccaccc cacaggacct     1320
gaacacgatg ttgaacaccg tggggggaca tcaagcagcc atgcaaatgt taaaagagac     1380
catcaatgag gaagctgcag aatgggatag agtgcatcca gtgcatgcag gcctattgc      1440 accaggccag atgagagaac caaggggaag tgacatagca ggaactacta gtacccttca     1500
ggaacaaata ggatggatga caaataatcc acctatccca gtaggagaga tctacaagag     1560
gtggataatc ctgggattga caagatcgt gaggatgtat agccctacca gcattctgga     1620
cataagacaa ggaccaaagg aaccctttag agactatgta gaccggttct ataaaactct     1680
aagagctgag caagcttcac aggaggtaaa aaattggatg acagaaacct tgttggtcca     1740
aaatgcgaac ccagattgta agaccatcct gaaggctctc ggcccagcgg ctacactaga     1800
agaaatgatg acagcatgtc agggagtagg aggacccggc cataaggcaa gagttttggc     1860
cgaggcgatg agccaggtga cgaactcggc gaccataatg atgcagagag caacttccg      1920 gaaccagcgg aagatcgtca agtgcttcaa ttgtggcaaa gaagggcaca ccgccaggaa     1980
ctgccgggcc ccccggaaga agggctgttg gaaatgtgga aggaaggac accaaatgaa     2040 agattgtact gagagacagg ctaattttt agggaagatc tggccttcct acaagggaag     2100
gccagggaat tttcttcaga gcagaccaga gccaacagcc ccaccagaag agagcttcag     2160
gtctggggta gagacaacaa ctccccctca gaagcaggag ccgatagaca aggaactgta     2220
tcctttaact tccctcagat cactctttgg caacgacccc tcgtcacagt aaggatcggg     2280
gggcaactca aggaagcgct gctcgataca ggagcagatg atacagtatt agaagaaatg     2340
agtttgccag gaagatggaa accaaaaatg atagggggga tcgggggctt catcaaggtg     2400
aggcagtacg accagatact catagaaatc tgtggacata agctataggg tacagtatta     2460
gtaggaccta cacctgtcaa cataattgga agaaatctgt tgacccagat cggctgcacc     2520
```

-continued

```
ttgaacttcc ccatcagccc tattgagacg gtgcccgtga agttgaagcc ggggatggac      2580
ggccccaagg tcaagcaatg gccattgacg aaagagaaga tcaaggcctt agtcgaaatc      2640
tgtacagaga tggagaagga agggaagatc agcaagatcg ggcctgagaa cccctacaac      2700
actccagtct tcgcaatcaa gaagaaggac agtaccaagt ggagaaagct ggtggacttc      2760
agagagctga acaagagaac tcaggacttc tgggaagttc agctgggcat cccacatccc      2820
gctgggttga agaagaagaa gtcagtgaca gtgctggatg tgggtgatgc ctacttctcc      2880
gttcccttgg acgaggactt caggaagtac actgccttca cgatacctag catcaacaac      2940
gagacaccag gcatccgcta ccagtacaac gtgctgccac agggatggaa gggatcacca      3000
gccatctttc aaagcagcat gaccaagatc ctggagccct tccgcaagca aaacccagac      3060
atcgtgatct atcagtacat ggacgacctc tacgtaggaa gtgacctgga gatcgggcag      3120
cacaggacca agatcgagga gctgagacag catctgttga ggtggggact gaccacacca      3180
gacaagaagc accagaagga acctcccttc ctgtggatgg gctacgaact gcatcctgac      3240
aagtggacag tgcagcccat cgtgctgcct gagaaggaca gctggactgt gaacgacata      3300
cagaagctcg tgggcaagtt gaactgggca agccagatct acccaggcat caaagttagg      3360
cagctgtgca agctgcttcg aggaaccaag gcactgacag aagtgatccc actgacagag      3420
gaagcagagc tagaactggc agagaaccga gagatcctga aggagccagt acatggagtg      3480
tactacgacc caagcaagga cctgatcgca gagatccaga agcaggggca aggccaatgg      3540
acctaccaaa tctaccagga gcccttcaag aacctgaaga caggcaagta cgcaaggatg      3600
aggggtgccc acaccaacga tgtgaagcag ctgacagagg cagtgcagaa gatcaccaca      3660
gagagcatcg tgatctgggg caagactccc aagttcaagc tgcccataca aggagaca      3720 tgggagacat ggtggaccga gtactggcaa gccacctgga tccctgagtg ggagttcgtg      3780
aacacccctc ccttggtgaa actgtggtat cagctggaga aggaacccat cgtgggagca      3840
gagaccttct acgtggatgg ggcagccaac agggagacca agctgggcaa ggcaggctac      3900
gtgaccaacc gaggacgaca gaaagtggtg accctgactg acaccaccaa ccagaagact      3960
gagctgcaag ccatctacct agctctgcaa gacagcggac tggaagtgaa catcgtgaca      4020
gactcacagt acgcactggg catcatccaa gcacaaccag accaatccga gtcagagctg      4080
gtgaaccaga tcatcgagca gctgatcaag aaggagaaag tgtacctggc atgggtacca      4140
gcacacaaag gaattggagg aaatgaacaa gtagataaat tagtcagtgc tgggatccgg      4200
aaggtgctgt tcctggacgg gatcgataag gcccaagatg aacatgagaa gtaccactcc      4260
aactggcgcg ctatggccag cgacttcaac ctgccacctg tagtagcaaa agaaatagta      4320
gccagctgtg ataaatgtca gctaaaagga gaagccatgc atggacaagt agactgtagt      4380
ccaggaatat ggcagctgga ctgcacgcac ctggagggga aggtgatcct ggtagcagtt      4440
catgtagcca gtggatatat agaagcagaa gttatccctg ctgaaactgg gcaggaaaca      4500
gcatattttc ttttaaaatt agcaggaaga tggccagtaa aaacaataca cacggacaac      4560
ggaagcaact tcactggtgc tacggttaag gccgcctgtt ggtgggcggg aatcaagcag      4620
gaatttggaa ttccctacaa tccccaatcg caaggagtcg tggagagcat gaacaaggag      4680
ctgaagaaga tcatcggaca agtgagggat caggctgagc acctgaagac agcagtgcag      4740
atggcagtgt tcatccacaa cttcaaaaga aagggggga ttggggggta cagtgcaggg      4800
gaaaggatcg tggacatcat cgccaccgac atccaaacca aggagctgca gaagcagatc      4860
accaagatcc agaacttccg ggtgtactac cgcgacagcc gcaacccact gtggaaggga      4920
```

```
ccagcaaagc tcctctggaa gggagagggg gcagtggtga tccaggacaa cagtgacatc    4980
aaagtggtgc caaggcgcaa ggccaagatc atccgcgact atggaaaaca gatggcaggt    5040
gatgattgtg tggcaagtag acaggatgag gattagaacc tggaagagcc tggtgaagca    5100
ccatatggcg ttcgaagcta gcctcgagat ccagatctgc tgtgccttct agttgccagc    5160
catctgttgt tgcccctcc cccgtgcctt ccttgaccct ggaaggtgcc actcccactg    5220
tcctttccta ataaaatgag gaaattgcat cgcattgtct gagtaggtgt cattctattc    5280
tggggggtgg ggtggggcag cacagcaagg gggaggattg ggaagacaat agcaggcatg    5340
ctggggatgc ggtgggctct atgggtaccc aggtgctgaa gaattgaccc ggttcctcct    5400
gggccagaaa gaagcaggca catcccctts tctgtgacac ccctgtcca cgccctggt    5460 tcttagttcc agccccactc ataggacact catagctcag gagggctccg ccttcaatcc    5520
cacccgctaa agtacttgga gcggtctctc cctccctcat cagcccacca aaccaaacct    5580
agcctccaag agtgggaaga aattaaagca agataggcta ttaagtgcag agggagagaa    5640
aatgcctcca acatgtgagg aagtaatgag agaaatcata gaatttcttc cgcttcctcg    5700
ctcactgact cgctgcgctc ggtcgttcgg ctgcggcgag cggtatcagc tcactcaaag    5760
gcggtaatac ggttatccac agaatcaggg gataacgcag gaaagaacat gtgagcaaaa    5820
ggccagcaaa aggccaggaa ccgtaaaaag gccgcgttgc tggcgttttt ccataggctc    5880 cgccccctg acgagcatca caaaaatcga cgctcaagtc agaggtggcg aaacccgaca    5940
ggactataaa gataccaggc gtttccccct ggaagctccc tcgtgcgctc tcctgttccg    6000
accctgccgc ttaccggata cctgtccgcc tttctccctt cgggaagcgt ggcgctttct    6060
caatgctcac gctgtaggta tctcagttcg gtgtaggtcg ttcgctccaa gctgggctgt    6120
gtgcacgaac cccccgttca gcccgaccgc tgcgccttat ccggtaacta tcgtcttgag    6180
tccaacccgg taagacacga cttatcgcca ctggcagcag ccactggtaa caggattagc    6240
agagcgaggt atgtaggcgg tgctacagag ttcttgaagt ggtggcctaa ctacggctac    6300
actagaagga cagtatttgg tatctgcgct ctgctgaagc cagttacctt cggaaaaaga    6360
gttggtagct cttgatccgg caaacaaacc accgctggta gcggtggttt ttttgtttgc    6420
aagcagcaga ttacgcgcag aaaaaaagga tctcaagaag atcctttgat cttttctacg    6480
gggtctgacg ctcagtggaa cgaaaactca cgttaaggga ttttggtcat gagattatca    6540
aaaaggatct tcacctagat ccttttaaat taaaaatgaa gttttaaatc aatctaaagt    6600
atatatgagt aaacttggtc tgacagttac caatgcttaa tcagtgaggc acctatctca    6660
gcgatctgtc tatttcgttc atccatagtt gcctgactcc ggggggggg ggcgctgagg    6720 tctgcctcgt gaagaaggtg ttgctgactc ataccaggcc tgaatcgccc catcatccag    6780
ccagaaagtg agggagccac ggttgatgag agctttgttg taggtggacc agttggtgat    6840
tttgaacttt tgctttgcca cggaacggtc tgcgttgtcg ggaagatgcg tgatctgatc    6900
cttcaactca gcaaaagttc gatttattca acaaagccgc cgtcccgtca agtcagcgta    6960
atgctctgcc agtgttacaa ccaattaacc aattctgatt agaaaaactc atcgagcatc    7020
aaatgaaact gcaatttatt catatcagga ttatcaatac catattttg aaaaagccgt    7080 ttctgtaatg aaggagaaaa ctcaccgagg cagttccata ggatggcaag atcctggtat    7140
cggtctgcga ttccgactcg tccaacatca atacaaccta ttaatttccc ctcgtcaaaa    7200
ataaggttat caagtgagaa atcaccatga gtgacgactg aatccggtga gaatggcaaa    7260
```

-continued

```
agcttatgca tttctttcca gacttgttca acaggccagc cattacgctc gtcatcaaaa      7320
tcactcgcat caaccaaacc gttattcatt cgtgattgcg cctgagcgag acgaaatacg      7380
cgatcgctgt taaaggaca attacaaaca ggaatcgaat gcaaccggcg caggaacact       7440
gccagcgcat caacaatatt ttcacctgaa tcaggatatt cttctaatac ctggaatgct      7500
gttttcccgg ggatcgcagt ggtgagtaac catgcatcat caggagtacg ataaaatgc       7560 ttgatggtcg gaagaggcat aaattccgtc agccagttta gtctgaccat ctcatctgta     7620
acatcattgg caacgctacc tttgccatgt ttcagaaaca actctggcgc atcgggcttc      7680
ccatacaatc gatagattgt cgcacctgat tgcccgacat tatcgcgagc ccatttatac      7740
ccatataaat cagcatccat gttggaattt aatcgcggcc tcgagcaaga cgtttcccgt      7800
tgaatatggc tcataacacc ccttgtatta ctgtttatgt aagcagacag ttttattgtt      7860
catgatgata tatttttatc ttgtgcaatg taacatcaga gattttgaga cacaacgtgg      7920
ctttcccccc cccccccatta ttgaagcatt tatcagggtt attgtctcat gagcggatac     7980
atatttgaat gtatttagaa aaataaacaa ataggggttc cgcgcacatt tccccgaaaa      8040
gtgccacctg acgtctaaga aaccattatt atcatgacat taacctataa aaataggcgt     8100
atcacgaggc cctttcgtct cgcgcgtttc ggtgatgacg gtgaaaacct ctgacacatg      8160
cagctcccgg agacggtcac agcttgtctg taagcggatg ccgggagcag acaagcccgt     8220
cagggcgcgt cagcgggtgt tggcgggtgt cggggctggc ttaactatgc ggcatcagag      8280
cagattgtac tgagagtgca ccatatgcgg tgtgaaatac cgcacagatg cgtaaggaga      8340
aaataccgca tcagattggc tattgg                                          8366
```

<210> SEQ ID NO 7
<211> LENGTH: 271
<212> TYPE: PRT
<213> ORGANISM: Escherichia coli

<400> SEQUENCE: 7

```
Met Ser His Ile Gln Arg Glu Thr Ser Cys Ser Arg Pro Arg Leu Asn
  1               5                  10                  15

Ser Asn Met Asp Ala Asp Leu Tyr Gly Tyr Lys Trp Ala Arg Asp Asn
             20                  25                  30

Val Gly Gln Ser Gly Ala Thr Ile Tyr Arg Leu Tyr Gly Lys Pro Asp
         35                  40                  45

Ala Pro Glu Leu Phe Leu Lys His Gly Lys Gly Ser Val Ala Asn Asp
     50                  55                  60

Val Thr Asp Glu Met Val Arg Leu Asn Trp Leu Thr Glu Phe Met Pro
 65                  70                  75                  80

Leu Pro Thr Ile Lys His Phe Ile Arg Thr Pro Asp Asp Ala Trp Leu
                 85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175
```

```
Gln Val Trp Lys Glu Met His Lys Leu Leu Pro Phe Ser Pro Asp Ser
                180                 185                 190
Val Val Thr His Gly Asp Phe Ser Leu Asp Asn Leu Ile Phe Asp Glu
            195                 200                 205
Gly Lys Leu Ile Gly Cys Ile Asp Val Gly Arg Val Gly Ile Ala Asp
        210                 215                 220
Arg Tyr Gln Asp Leu Ala Ile Leu Trp Asn Cys Leu Gly Glu Phe Ser
225                 230                 235                 240
Pro Ser Leu Gln Lys Arg Leu Phe Gln Lys Tyr Gly Ile Asp Asn Pro
                245                 250                 255
Asp Met Asn Lys Leu Gln Phe His Leu Met Leu Asp Glu Phe Phe
                260                 265                 270

<210> SEQ ID NO 8
<211> LENGTH: 8937
<212> TYPE: DNA
<213> ORGANISM: Artificial Sequence
<220> FEATURE:
<223> OTHER INFORMATION: Description of Artificial Sequence: DNA
      sequence of transfer construc pmBCwCNluci

<400> SEQUENCE: 8
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180
aataaggaga gaagaacagc ttgttacacc ctatgagcca gcatgggatg gaggacccgg     240
agggagaagt attagtgtgg aagtttgaca gcctcctagc atttcgtcac atggcccgag     300
agctgcatcc ggagtactac aaagactgct gacatcgagc tttctacaag ggactttccg     360
ctggggactt tccaggggag tgtggcctgg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata agcttgcct      540
tgagtgctca agtagtgtg tgcccgtctg ttgtgtgact ctggtaacta gagatccctc      600
agacccttt agtcagtgtg gaaaatctct agcagtggcg cccgaacagg gacttgaaag      660
cgaaagtaaa gccagaggag atctctcgac gcaggactcg gcttgctgaa gcgcgcacgg      720
caagaggcga gggcggcgc ctgacgagga cgccaaaaat tttgactagc ggaggctaga      780
aggagagagc tcggtgcgag agcgtcagta ttaagcgggg gagaattaga tcgatgggaa      840
aaaattcggt taaggccagg gggaaagaaa aaatataaat taaaacatat agtatgggca     900
agcagggagc tagaacgatt cgcagttaat cctggcctgt tagaaacatc agaaggctgt     960
agacaaatac tgggacagct acaaccatcc cttcagacag gatcagaaga acttagatca    1020
ttatataata cagtagcaac cctctattgt gtgcatcaaa ggatagagat aaaagacacc    1080
aaggaagctt tagacaagat agaggaagag caaaacaaaa gtaagaaaaa agcacagcaa    1140
gcagcagctg acacaggaca cagcaatcag gtcagccaaa attaccctat agtgcagaac    1200
atccagggc aaatggtaca tcaggccata tcacctagaa ctttaaacga taagcttggg     1260
agttccgcgt tacataactt acggtaaatg cccgcctgg ctgaccgccc aacgaccccc      1320
gcccattgac gtcaataatg acgtatgttc ccatagtaac gccaatagg actttccatt      1380
gacgtcaatg ggtggagtat ttacggtaaa ctgcccactt ggcagtacat caagtgtatc    1440
atatgccaag tacgcccct attgacgtca atgacggtaa atggcccgcc tggcattatg     1500
```

-continued

```
cccagtacat gaccttatgg gactttccta cttggcagta catctacgta ttagtcatcg    1560
ctattaccat ggtgatgcgg ttttggcagt acatcaatgg gcgtggatag cggtttgact    1620
cacggggatt tccaagtctc caccccattg acgtcaatgg gagtttgttt tggcaccaaa    1680
atcaacggga ctttccaaaa tgtcgtaaca actccgcccc attgacgcaa atgggcggta    1740
ggcgtgtacg gtgggaggtc tatataagca gagctcgttt agtgaaccgt cagatcgcct    1800
ggagacgcca tccacgctgt tttgacctcc atagaagaca ccgactctag aggatccatc    1860
taagtaagct tggcattccg gtactgttgg taaaatggaa gacgccaaaa acataaagaa    1920
aggcccggcg ccattctatc ctctagagga tggaaccgct ggagagcaac tgcataaggc    1980
tatgaagaga tacgccctgg ttcctggaac aattgctttt acagatgcac atatcgaggt    2040
gaacatcacg tacgcggaat acttcgaaat gtccgttcgg ttggcagaag ctatgaaacg    2100
atatgggctg aatacaaatc acagaatcgt cgtatgcagt gaaaactctc ttcaattctt    2160
tatgccggtg ttgggcgcgt tatttatcgg agttgcagtt gcgcccgcga acgacattta    2220
taatgaacgt gaattgctca acagtatgaa catttcgcag cctaccgtag tgtttgtttc    2280
caaaaagggg ttgcaaaaaa ttttgaacgt gcaaaaaaaa ttaccaataa tccagaaaat    2340
tattatcatg gattctaaaa cggattacca gggatttcag tcgatgtaca cgttcgtcac    2400
atctcatcta cctcccggtt ttaatgaata cgattttgta ccagagtcct ttgatcgtga    2460
caaaacaatt gcactgataa tgaattcctc tggatctact gggttaccta agggtgtggc    2520
ccttccgcat agaactgcct gcgtcagatt ctcgcatgcc agagatccta ttttttggcaa    2580 tcaaatcatt ccggatactg cgattttaag tgttgttcca ttccatcacg gttttggaat    2640
gtttactaca ctcggatatt tgatatgtgg atttcgagtc gtcttaatgt atagatttga    2700
agaagagctg ttttttacgat cccttcagga ttacaaaatt caaagtgcgt tgctagtacc    2760
aaccctattt tcattcttcg ccaaaagcac tctgattgac aaatacgatt tatctaattt    2820
acacgaaatt gcttctgggg gcgcacctct ttcgaaagaa gtcggggaag cggttgcaaa    2880
acgcttccat cttccaggga tacgacaagg atatgggctc actgagacta catcagctat    2940
tctgattaca cccgaggggg atgataaacc gggcgcggtc ggtaaagttg ttccattttt    3000
tgaagcgaag gttgtggatc tggataccgg gaaaacgctg ggcgttaatc agagaggcga    3060
attatgtgtc agaggaccta tgattatgtc cggttatgta acaatccgg aagcgaccaa    3120 cgccttgatt gacaaggatg gatggctaca ttctggagac atagcttact gggacgaaga    3180
cgaacacttc ttcatagttg accgcttgaa gtctttaatt aaatacaaag gatatcaggt    3240
ggcccccgct gaattggaat cgatattgtt acaacacccc aacatcttcg acgcgggcgt    3300
ggcaggtctt cccgacgatg acgccggtga acttcccgcc gccgttgttg ttttggagca    3360
cggaaagacg atgacggaaa aagagatcgt ggattacgtc gccagtcaag taacaaccgc    3420
gaaaaagttg cgcggaggag ttgtgtttgt ggacgaagta ccgaaaggtc ttaccggaaa    3480
actcgacgca agaaaaatca gagagatcct cataaaggcc aagaagggcg aaagtccaa    3540 attgtaactc gagggggggc ccggtacctt taagaccaat gacttacaag gcagctgtag    3600
atcttagcca cttttttaaaa gaaaggggg gactggaagg gctaattcac tcccaaagaa    3660
gacaagatat ccttgatctg tggatctacc acacacaagg ctacttccct gattggcaga    3720
actacacacc agggccaggg gtcagatatc cactgacctt tggatggtgc tacaagctag    3780
taccagttga gccagataag gtagaagagg ccaataaagg agagaacacc agcttgttac    3840
accctgtgag cctgcatgga atggatgacc ctgagagaga agtgttagag tggaggtttg    3900
```

```
acagccgcct agcatttcat cacgtggccc gagagctgca tccggagtac ttcaagaact    3960
gctgacatcg agcttgctac aagggacttt ccgctgggga ctttccaggg aggcgtggcc    4020
tgggcgggac tggggagtgg cgagccctca gatgctgcat ataagcagct gcttttttgcc   4080
tgtactgggt ctctctggtt agaccagatc tgagcctggg agctctctgg ctaactaggg    4140
aacccactgc ttaagcctca ataaagcttg ccttgagtgc ttcaagtagt gtgtgcccgt    4200
ctgttgtgtg actctggtaa ctagagatcc ctcagaccct tttagtcagt gtggaaaatc    4260
tctagcaccc cccaggaggt agaggttgca gtgagccaag atcgcgccac tgcattccag    4320
cctgggcaag aaaacaagac tgtctaaaat aataataata agttaagggt attaaatata    4380
tttatacatg gaggtcataa aaatatatat atttgggctg gcgcagtgg ctcacacctg     4440
cgcccggccc tttgggaggc cgaggcaggt ggatcacctg agtttgggag ttccagacca    4500
gcctgaccaa catggagaaa ccccttctct gtgtattttt agtagatttt attttatgtg    4560
tattttattc acaggtattt ctggaaaact gaaactgttt ttcctctact ctgataccac    4620
aagaatcatc agcacagagg aagacttctg tgatcaaatg tggtgggaga gggaggtttt    4680
caccagcaca tgagcagtca gttctgccgc agactcggcg ggtgtccttc ggttcagttc    4740
caacaccgcc tgcctggaga gaggtcagac cacagggtga gggctcagtc cccaagacat    4800
aaacacccaa gacataaaca cccaacaggt ccaccccgcc tgctgcccag gcagagccga    4860
ttcaccaaga cgggaattag gatagagaaa gagtaagtca cacagagccg gctgtgcggg    4920
agaacggagt tctattatga ctcaaatcag tctccccaag cattcgggga tcagagtttt    4980
taaggataac ttagtgtgta gggggccagt gagttggaga tgaaagcgta gggagtcgaa    5040
ggtgtccttt tgcgccgagt cagttcctgg gtgggggcca aagatcgga tgagccagtt    5100
tatcaatccg ggggtgccag ctgatccatg gagtgcaggg tctgcaaaat atctcaagca    5160
ctgattgatc ttaggtttta caatagtgat gttacccaag aacaatttg gggaaggtca     5220
gaatcttgta gcctgtagct gcatgactcc taaaccataa tttctttttt gttttttttt    5280
ttttattttt gagacagggt ctcactctgt cacctaggct ggagtgcagt ggtgcaatca    5340
cagctcactg cagcccctag agcggccgcc accgcggtgg agctccaatt cgccctatag    5400
tgagtcgtat tacaattcac tggccgtcgt tttacaacgt cgtgactggg aaaaccctgg    5460
cgttacccaa cttaatcgcc ttgcagcaca tccccctttc gccagctggc gtaatagcga    5520
agaggcccgc accgatcgcc cttcccaaca gttgcgcagc ctgaatggcg aatggcgcga    5580
aattgtaaac gttaatattt tgttaaaatt cgcgttaaat ttttgttaaa tcagctcatt    5640
ttttaaccaa taggccgaaa tcggcaaaat cccttataaa tcaaaagaat agaccgagat    5700
agggttgagt gttgttccag tttggaacaa gagtccacta ttaaagaacg tggactccaa    5760
cgtcaaaggg cgaaaaaccg tctatcaggg cgatggccca ctacgtgaac catcacccta    5820
atcaagtttt tgggtcga ggtgccgtaa agcactaaat cggaaccta aagggagccc       5880
ccgatttaga gcttgacggg gaagccggc gaacgtggcg agaaaggaag ggaagaaagc     5940
gaaaggagcg ggcgctaggg cgctggcaag tgtagcggtc acgctgcgcg taaccaccac    6000
acccgccgcg cttaatgcgc cgctacaggg cgcgtcccag gtggcacttt tcggggaaat    6060
gtgcgcggaa cccctatttg tttatttttc taaatacatt caaatatgta tccgctcatg    6120
agacaataac cctgataaat gcttcaataa tattgaaaaa ggaagagtat gagtattcaa    6180
catttccgtg tcgcccttat tccctttttt gcggcatttt gccttcctgt ttttgctcac    6240
```

-continued

```
ccagaaacgc tggtgaaagt aaaagatgct gaagatcagt tgggtgcacg agtgggttac   6300
atcgaactgg atctcaacag cggtaagatc cttgagagtt ttcgccccga agaacgtttt   6360
ccaatgatga gcacttttaa agttctgcta tgtggcgcgg tattatcccg tattgacgcc   6420
gggcaagagc aactcggtcg ccgcatacac tattctcaga atgacttggt tgagtactca   6480
ccagtcacag aaaagcatct tacggatggc atgacagtaa gagaattatg cagtgctgcc   6540
ataaccatga gtgataacac tgcggccaac ttacttctga caacgatcgg aggaccgaag   6600
gagctaaccg ctttttttgca caacatgggg gatcatgtaa ctcgccttga tcgttgggaa   6660
ccggagctga atgaagccat accaaacgac gagcgtgaca ccacgatgcc tgtagcaatg   6720
gcaacaacgt tgcgcaaact attaactggc gaactactta ctctagcttc ccggcaacaa   6780
ttaatagact ggatggaggc ggataaagtt gcaggaccac ttctgcgctc ggcccttccg   6840
gctggctggt ttattgctga taaatctgga gccggtgagc gtgggtctcg cggtatcatt   6900
gcagcactgg ggccagatgg taagccctcc cgtatcgtag ttatctacac gacggggagt   6960
caggcaacta tggatgaacg aaatagacag atcgctgaga taggtgcctc actgattaag   7020
cattggtaac tgtcagacca gtttactca tatatacttt agattgattt aaaacttcat   7080
ttttaattta aaaggatcta ggtgaagatc ctttttgata atctcatgac caaaatccct   7140
taacgtgagt tttcgttcca ctgagcgtca ccccgtag aaaagatcaa aggatcttct   7200
tgagatcctt ttttttctgcg cgtaatctgc tgcttgcaaa caaaaaaacc accgctacca   7260
gcggtggttt gtttgccgga tcaagagcta ccaactcttt ttccgaaggt aactggcttc   7320
agcagagcgc agataccaaa tactgtcctt ctagtgtagc cgtagttagg ccaccacttc   7380
aagaactctg tagcaccgcc tacatacctc gctctgctaa tcctgttacc agtggctgct   7440
gccagtggcg ataagtcgtg tcttaccggg ttggactcaa gacgatagtt accggataag   7500
gcgcagcggt cgggctgaac ggggggttcg tgcacacagc ccagcttgga gcgaacgacc   7560
tacaccgaac tgagatacct acagcgtgag ctatgagaaa gcgccacgct cccgaaggg   7620 agaaaggcgg acaggtatcc ggtaagcgg agggtcggaa caggagagcg cacgagggag   7680
cttccagggg gaaacgcctg gtatctttat agtcctgtcg ggtttcgcca cctctgactt   7740
gagcgtcgat ttttgtgatg ctcgtcaggg gggcggagcc tatggaaaaa cgccagcaac   7800
gcggcctttt tacggttcct ggccttttgc tggcctttg ctcacatgtt ctttcctgcg   7860
ttatcccctg attctgtgga taaccgtatt accgcctttg agtgagctga taccgctcgc   7920
cgcagccgaa cgaccgagcg cagcgagtca gtgagcgagg aagcggaaga gcgcccaata   7980
cgcaaaccgc ctctccccgc gcgttggccg attcattaat gcagctggca cgacaggttt   8040
cccgactgga aagcgggcag tgagcgcaac gcaattaatg tgagttagct cactcattag   8100 gcacccccagg ctttacactt tatgcttccg gctcgtatgt tgtgtggaat tgtgagcgga   8160
taacaatttc acacaggaaa cagctatgac catgattacg ccaagctcgg aattaaccct   8220
cactaaaggg aacaaaagct gctgcagggt ccctaactgc caagcccac agtgtgccct   8280 gaggctgccc cttccttcta gcggctgccc ccactcggct ttgctttccc tagtttcagt   8340
tacttgcgtt cagccaaggt ctgaaactag gtgcgcacag agcggtaaga ctgcgagaga   8400
aagagaccag ctttacaggg ggtttatcac agtgcaccct gacagtcgtc agcctcacag   8460
ggggtttatc acattgcacc ctgacagtcg tcagcctcac agggggttta tcacagtgca   8520
cccttacaat cattccattt gattcacaat ttttttagtc tctactgtgc ctaacttgta   8580
agttaaattt gatcagaggt gtgttcccag agggaaaaac agtatataca gggttcagta   8640
```

-continued

```
ctatcgcatt tcaggcctcc acctgggtct tggaatgtgt cccccgaggg gtgatgacta      8700
cctcagttgg atctccacag gtcacagtga cacaagataa ccaagacacc tcccaaggct      8760
accacaatgg gccgccctcc acgtgcacat ggccggagga actgccatgt cggaggtgca      8820
agcacacctg cgcatcagag tccttggtgt ggagggaggg accagcgcag cttccagcca      8880
tccacctgat gaacagaacc tagggaaagc cccagttcta cttacaccag gaaaggc        8937
```

<210> SEQ ID NO 9
<211> LENGTH: 8937
<212> TYPE: DNA
<213> ORGANISM: Artificial Sequence
<220> FEATURE:
<223> OTHER INFORMATION: Description of Artificial Sequence:  DNA
      sequence from transfer construct pmBCmCNluci

<400> SEQUENCE: 9

```
tggaagggct aatttggtcc caaaaaagac aagagatcct tgatctgtgg atctaccaca        60
cacaaggcta cttccctgat tggcagaact acacaccagg gccagggatc agatatccac       120
tgacctttgg atggtgcttc aagttagtac cagttgaacc agagcaagta gaagaggcca       180
aataaggaga gaagaacagc ttgttacacc ctatgagcca gcatgggatg gaggacccgg       240
agggagaagt attagtgtgg aagtttgaca gcctcctagc atttcgtcac atggcccgag       300
agctgcatcc ggagtactac aaagactgct gacatcgagc tttctacaag ggactttccg       360
ctggggactt tccaggagg tgtggcctgg gcgggactgg ggagtggcga gccctcagat         420
gctacatata agcagctgct ttttgcctgt actgggtctc tctggttaga ccagatctga       480
gcctgggagc tctctggcta actagggaac ccactgctta agcctcaata aagcttgcct       540
tgagtgctca agtagtgtg tgcccgtctg ttgtgtgact ctggtaacta gagatccctc        600
agaccctttt agtcagtgtg gaaaatctct agcagtggcg cccgaacagg gacttgaaag       660
cgaaagtaaa gccagaggag atctctcgac gcaggactcg gcttgctgaa gcgcgcacgg       720
caagaggcga gggcggcgc ctgacgagga cgccaaaaat tttgactagc ggaggctaga        780
aggagagagc tcggtgcgag agcgtcagta ttaagcgggg gagaattaga tcgatgggaa       840
aaaattcggt taaggccagg gggaagaag aagtacaagc taaagcacat cgtatgggca       900
agcagggagc tagaacgatt cgcagttaat cctggcctgt tagaaacatc agaaggctgt       960
agacaaatac tgggacagct acaaccatcc cttcagacag gatcagagga gcttcgatca      1020
ctatacaaca cagtagcaac cctctattgt gtgcaccagc ggatcgagat caaggacacc      1080
aaggaagctt tagacaagat agaggaagag caaaacaagt ccaagaagaa ggcccagcag      1140
gcagcagctg acacaggaca cagcaatcag gtcagccaaa attaccctat agtgcagaac      1200
atccaggggc aaatggtaca tcaggccata tcacctagaa ctttaaacga taagcttggg      1260
agttccgcgt tacataactt acggtaaatg gcccgcctgg ctgaccgccc aacgaccccc      1320
gcccattgac gtcaataatg acgtatgttc ccatagtaac gccaataggg actttccatt      1380
gacgtcaatg ggtggagtat ttacggtaaa ctgcccactt ggcagtacat caagtgtatc      1440
atatgccaag tacgccccct attgacgtca atgacggtaa atggcccgcc tggcattatg      1500
cccagtacat gaccttatgg gactttccta cttggcagta catctacgta ttagtcatcg      1560
ctattaccat ggtgatgcgg ttttggcagt acatcaatgg gcgtggatag cggtttgact      1620
cacggggatt tccaagtctc cacccccattg acgtcaatgg gagtttgttt tggcaccaaa    1680
atcaacggga ctttccaaaa tgtcgtaaca actccgcccc attgacgcaa atgggcggta    1740
```

```
ggcgtgtacg gtgggaggtc tatataagca gagctcgttt agtgaaccgt cagatcgcct    1800
ggagacgcca tccacgctgt tttgacctcc atagaagaca ccgactctag aggatccatc    1860
taagtaagct tggcattccg gtactgttgg taaaatggaa gacgccaaaa acataaagaa    1920
aggcccggcg ccattctatc ctctagagga tggaaccgct ggagagcaac tgcataaggc    1980
tatgaagaga tacgccctgg ttcctggaac aattgctttt acagatgcac atatcgaggt    2040
gaacatcacg tacgcggaat acttcgaaat gtccgttcgg ttggcagaag ctatgaaacg    2100
atatgggctg aatacaaatc acagaatcgt cgtatgcagt gaaaactctc ttcaattctt    2160
tatgccggtg ttgggcgcgt tatttatcgg agttgcagtt gcgcccgcga acgacattta    2220
taatgaacgt gaattgctca acagtatgaa catttcgcag cctaccgtag tgtttgtttc    2280
caaaaggggg ttgcaaaaaa ttttgaacgt gcaaaaaaaa ttaccaataa tccagaaaat    2340
tattatcatg gattctaaaa cggattacca gggatttcag tcgatgtaca cgttcgtcac    2400
atctcatcta cctcccggtt ttaatgaata cgattttgta ccagagtcct ttgatcgtga    2460
caaaacaatt gcactgataa tgaattcctc tggatctact gggttaccta agggtgtggc    2520
ccttccgcat agaactgcct gcgtcagatt ctcgcatgcc agagatccta ttttttggcaa    2580 tcaaatcatt ccggatactg cgattttaag tgttgttcca ttccatcacg gttttggaat    2640
gtttactaca ctcggatatt tgatatgtgg atttcgagtc gtcttaatgt atagatttga    2700
agaagagctg tttttacgat cccttcagga ttacaaaatt caaagtgcgt tgctagtacc    2760
aaccctattt tcattcttcg ccaaaagcac tctgattgac aaatacgatt tatctaattt    2820
acacgaaatt gcttctgggg gcgcacctct ttcgaaagaa gtcggggaag cggttgcaaa    2880
acgcttccat cttccaggga tacgacaagg atatgggctc actgagacta catcagctat    2940
tctgattaca cccgaggggg atgataaacc gggcgcggtc ggtaaagttg ttccattttt    3000
tgaagcgaag gttgtggatc tggataccgg gaaaacgctg ggcgttaatc agagaggcga    3060
attatgtgtc agaggaccta tgattatgtc cggttatgta aacaatccgg aagcgaccaa    3120
cgccttgatt gacaaggatg gatggctaca ttctggagac atagcttact gggacgaaga    3180
cgaacacttc ttcatagttg accgcttgaa gtctttaatt aaatacaaag gatatcaggt    3240
ggcccccgct gaattggaat cgatattgtt acaacacccc aacatcttcg acgcgggcgt    3300
ggcaggtctt cccgacgatg acgccggtga acttcccgcc gccgttgttg ttttggagca    3360
cggaaagacg atgacggaaa aagagatcgt ggattacgtc gccagtcaag taacaaccgc    3420
gaaaaagttg cgcggaggag ttgtgtttgt ggacgaagta ccgaaaggtc ttaccggaaa    3480
actcgacgca agaaaaatca gagagatcct cataaaggcc aagaagggcg gaaagtccaa    3540
attgtaactc gagggggggc ccggtacctt aagaccaat gacttacaag gcagctgtag    3600
atcttagcca ctttttaaaa gaaaagggg gactggaagg gctaattcac tcccaaagaa    3660
gacaagatat ccttgatctg tggatctacc acacacaagg ctacttccct gattggcaga    3720
actacacacc agggccaggg gtcagatatc cactgacctt tggatggtgc tacaagctag    3780
taccagttga gccagataag gtagaagagg ccaataaagg agagaacacc agcttgttac    3840
accctgtgag cctgcatgga atggatgacc ctgagagaga agtgttagag tggaggtttg    3900
acagccgcct agcatttcat cacgtggccc gagagctgca tccggagtac ttcaagaact    3960
gctgacatcg agcttgctac aagggacttt ccgctgggga ctttccaggg aggcgtggcc    4020
tgggcgggac tggggagtgg cgagccctca gatgctgcat ataagcagct gcttttgcc    4080
```

-continued

| | |
|---|---|
| tgtactgggt ctctctggtt agaccagatc tgagcctggg agctctctgg ctaactaggg | 4140 |
| aacccactgc ttaagcctca ataaagcttg ccttgagtgc ttcaagtagt gtgtgcccgt | 4200 |
| ctgttgtgtg actctggtaa ctagagatcc ctcagaccct tttagtcagt gtggaaaatc | 4260 |
| tctagcaccc cccaggaggt agaggttgca gtgagccaag atcgcgccac tgcattccag | 4320 |
| cctgggcaag aaaacaagac tgtctaaaat aataataata agttaagggt attaaatata | 4380 |
| tttatacatg gaggtcataa aatatatat atttgggctg gcgcagtgg ctcacacctg | 4440 |
| cgcccggccc tttgggaggc cgaggcaggt ggatcacctg agtttgggag ttccagacca | 4500 |
| gcctgaccaa catggagaaa ccccttctct gtgtatttttt agtagatttt attttatgtg | 4560 |
| tattttattc acaggtattt ctggaaaact gaaactgttt ttcctctact ctgataccac | 4620 |
| aagaatcatc agcacagagg aagacttctg tgatcaaatg tggtgggaga gggaggtttt | 4680 |
| caccagcaca tgagcagtca gttctgccgc agactcggcg ggtgtccttc ggttcagttc | 4740 |
| caacaccgcc tgcctggaga gaggtcagac cacagggtga gggctcagtc cccaagacat | 4800 |
| aaacacccaa gacataaaca cccaacaggt ccaccccgcc tgctgcccag gcagagccga | 4860 |
| ttcaccaaga cgggaattag gatagagaaa gagtaagtca cacagagccg gctgtgcggg | 4920 |
| agaacggagt tctattatga ctcaaatcag tctccccaag cattcgggga tcagagtttt | 4980 |
| taaggataac ttagtgtgta gggggccagt gagttggaga tgaaagcgta gggagtcgaa | 5040 |
| ggtgtccttt tgcgccgagt cagttcctgg gtgggggcca caagatcgga tgagccagtt | 5100 |
| tatcaatccg ggggtgccag ctgatccatg gagtgcaggt ctgcaaaat atctcaagca | 5160 |
| ctgattgatc ttaggtttta caatagtgat gttaccccag gaacaatttg gggaaggtca | 5220 |
| gaatcttgta gcctgtagct gcatgactcc taaaccataa tttcttttt gtttttttt | 5280 |
| ttttatttt gagacagggt ctcactctgt cacctaggct ggagtgcagt ggtgcaatca | 5340 |
| cagctcactg cagcccctag agcggccgcc accgcggtgg agctccaatt cgccctatag | 5400 |
| tgagtcgtat tacaattcac tggccgtcgt tttacaacgt cgtgactggg aaaaccctgg | 5460 |
| cgttacccaa cttaatcgcc ttgcagcaca tcccccttc gccagctggc gtaatagcga | 5520 |
| agaggcccgc accgatcgcc cttcccaaca gttgcgcagc ctgaatggcg aatggcgcga | 5580 |
| aattgtaaac gttaatatt tgttaaaatt cgcgttaaat ttttgttaaa tcagctcatt | 5640 |
| ttttaaccaa taggccgaaa tcggcaaaat cccttataaa tcaaaagaat agaccgagat | 5700 |
| agggttgagt gttgttccag tttggaacaa gagtccacta ttaaagaacg tggactccaa | 5760 |
| cgtcaaaggg cgaaaaaccg tctatcaggg cgatggccca ctacgtgaac catcaccccta | 5820 |
| atcaagtttt tgggggtcga ggtgccgtaa agcactaaat cggaacccta aagggagccc | 5880 |
| ccgatttaga gcttgacggg gaaagccggc gaacgtggcg agaaaggaag ggaagaaagc | 5940 |
| gaaaggagcg ggcgctaggg cgctggcaag tgtagcggtc acgctgcgcg taaccaccac | 6000 |
| acccgccgcg cttaatgcgc cgctacaggg cgcgtcccag gtggcacttt tcggggaaat | 6060 |
| gtgcgcggaa cccctatttg tttatttttc taaatacatt caaatatgta tccgctcatg | 6120 |
| agacaataac cctgataaat gcttcaataa tattgaaaaa ggaagagtat gagtattcaa | 6180 |
| catttccgtg tcgcccttat tccctttttt gcggcatttt gccttcctgt ttttgctcac | 6240 |
| ccagaaacgc tggtgaaagt aaaagatgct gaagatcagt tgggtgcacg agtgggttac | 6300 |
| atcgaactgg atctcaacag cggtaagatc cttgagagtt ttcgccccga agaacgtttt | 6360 |
| ccaatgatga gcacttttaa agttctgcta tgtggcgcgg tattatcccg tattgacgcc | 6420 |
| gggcaagagc aactcggtcg ccgcatacac tattctcaga atgacttggt tgagtactca | 6480 |

```
ccagtcacag aaaagcatct tacggatggc atgacagtaa gagaattatg cagtgctgcc    6540
ataaccatga gtgataacac tgcggccaac ttacttctga caacgatcgg aggaccgaag    6600
gagctaaccg cttttttgca caacatgggg gatcatgtaa ctcgccttga tcgttgggaa    6660
ccggagctga atgaagccat accaaacgac gagcgtgaca ccacgatgcc tgtagcaatg    6720
gcaacaacgt tgcgcaaact attaactggc gaactactta ctctagcttc ccggcaacaa    6780
ttaatagact ggatggaggc ggataaagtt gcaggaccac ttctgcgctc ggcccttccg    6840
gctggctggt ttattgctga taaatctgga gccgtgagc gtgggtctcg cggtatcatt     6900
gcagcactgg ggccagatgg taagccctcc cgtatcgtag ttatctacac gacggggagt    6960
caggcaacta tggatgaacg aaatagacag atcgctgaga taggtgcctc actgattaag    7020
cattggtaac tgtcagacca agtttactca tatatacttt agattgattt aaaacttcat    7080
ttttaattta aaaggatcta ggtgaagatc ctttttgata atctcatgac caaatccct     7140 taacgtgagt tttcgttcca ctgagcgtca gaccccgtag aaaagatcaa aggatcttct    7200
tgagatcctt ttttttctgcg cgtaatctgc tgcttgcaaa caaaaaaacc accgctacca   7260
gcggtggttt gtttgccgga tcaagagcta ccaactcttt ttccgaaggt aactggcttc    7320
agcagagcgc agataccaaa tactgtcctt ctagtgtagc cgtagttagg ccaccacttc    7380
aagaactctg tagcaccgcc tacatacctc gctctgctaa tcctgttacc agtggctgct    7440
gccagtggcg ataagtcgtg tcttaccggg ttggactcaa gacgatagtt accggataag    7500
gcgcagcggt cgggctgaac ggggggttcg tgcacacagc ccagcttgga gcgaacgacc    7560
tacaccgaac tgagatacct acagcgtgag ctatgagaaa gcgccacgct tcccgaaggg    7620
agaaaggcgg acaggtatcc ggtaagcggc agggtcggaa caggagagcg cacgagggag    7680
cttccagggg gaaacgcctg gtatctttat agtcctgtcg ggtttcgcca cctctgactt    7740
gagcgtcgat ttttgtgatg ctcgtcaggg gggcggagcc tatggaaaaa cgccagcaac    7800
gcggcctttt tacggttcct ggccttttgc tggccttttg ctcacatgtt ctttcctgcg    7860
ttatcccctg attctgtgga taaccgtatt accgcctttg agtgagctga taccgctcgc    7920
cgcagccgaa cgaccgagcg cagcgagtca gtgagcgagg aagcggaaga gcgcccaata    7980
cgcaaaccgc ctctccccgc gcgttggccg attcattaat gcagctggca cgacaggttt    8040
cccgactgga aagcgggcag tgagcgcaac gcaattaatg tgagttagct cactcattag    8100
gcaccccagg ctttacactt tatgcttccg gctcgtatgt tgtgtggaat tgtgagcgga    8160
taacaatttc acacaggaaa cagctatgac catgattacg ccaagctcgg aattaaccct    8220
cactaaaggg aacaaaagct gctgcaggt cctaactgc caagcccac agtgtgccct      8280 gaggctgccc cttccttcta gcggctgccc ccactcggct ttgctttccc tagtttcagt    8340
tacttgcgtt cagccaaggt ctgaaactag gtgcgcacag agcggtaaga ctgcgagaga    8400
aagagaccag ctttacaggg ggtttatcac agtgcaccct gacagtcgtc agcctcacag    8460 gggggtttatc acattgcacc ctgacagtcg tcagcctcac aggggggttta tcacagtgca   8520 cccttacaat cattccattt gattcacaat tttttttagtc tctactgtgc ctaacttgta    8580
agttaaattt gatcagaggt gtgttccag aggggaaaac agtatataca gggttcagta     8640
ctatcgcatt tcaggcctcc acctgggtct tggaatgtgt cccccgaggg gtgatgacta    8700
cctcagttgg atctccacag gtcacagtga cacaagataa ccaagacacc tcccaaggct    8760
accacaatgg gccgccctcc acgtgcacat ggccggagga actgccatgt cggaggtgca    8820
```
agcacacctg cgcatcagag tccttggtgt ggagggaggg accagcgcag cttccagcca    8880
tccacctgat gaacagaacc tagggaaagc cccagttcta cttacaccag gaaaggc       8937

<210> SEQ ID NO 10
<211> LENGTH: 122
<212> TYPE: DNA
<213> ORGANISM: Artificial Sequence
<220> FEATURE:
<223> OTHER INFORMATION: Description of Artificial Sequence:  DNA
      sequence of the BSSHII to ClaI fragment in transfer
      construct pmBCwCNluci and pmBCmCNluci

<400> SEQUENCE: 10
cgcgcacggc aagaggcgag gggcggcgcc tgacgaggac gccaaaaatt ttgactagcg    60
gaggctagaa ggagagagct cggtgcgaga gcgtcagtat taagcggggg agaattagat   120
cg                                                                 122

<210> SEQ ID NO 11
<211> LENGTH: 122
<212> TYPE: DNA
<213> ORGANISM: Artificial Sequence
<220> FEATURE:
<223> OTHER INFORMATION: Description of Artificial Sequence:  DNA
      sequence of the BSSHII to ClaI fragment in transfer
      construct 3

<400> SEQUENCE: 11
cgcgcacggc aagaggcgag gggcggcgcc tggggaggac gccaaaaatt ttgactagcg    60
gaggctagaa ggagagagat gggtgcgaga gcgtcagtat taagcggggg agaattagat   120
cg                                                                 122

<210> SEQ ID NO 12
<211> LENGTH: 122
<212> TYPE: DNA
<213> ORGANISM: Human immunodeficiency virus type 1

<400> SEQUENCE: 12
cgcgcacggc aagaggcgag gggcggcgac tggtgagtac gccaaaaatt ttgactatcg    60
gaggctagaa ggagagagat gggtgcgaga gcgtcagtat taagcggggg agaattagat   120
cg                                                                 122

<210> SEQ ID NO 13
<211> LENGTH: 122
<212> TYPE: DNA
<213> ORGANISM: Artificial Sequence
<220> FEATURE:
<223> OTHER INFORMATION: Description of Artificial Sequence:  Plurality
      Consensus sequence of DNA sequence of the BSSHII
      to CLaI fragment in HIV-1 and transfer constructs

<400> SEQUENCE: 13
cgcgcacggc aagaggcgag gggcggcgac tggtgagtac gccaaaaatt ttgactagcg    60
gaggctagaa ggagagagat gggtgcgaga gcgtcggtat taagcggggg agaattagat   120
aa                                                                 122

<210> SEQ ID NO 14
<211> LENGTH: 122
<212> TYPE: DNA
<213> ORGANISM: Artificial Sequence
<220> FEATURE:
<223> OTHER INFORMATION: Description of Artificial Sequence:  DNA sequence of construct CMVkan/R-R-SIVgp160 CTE

<400> SEQUENCE: 14

| cgcgcacggc aagaggcgag gggcggcgac tggtgagtac gccaaaaatt ttgactagcg | 60 |
| gaggctagaa ggagagagat gggtgcgaga gcgtcagtat taagcggggg agaattagat | 120 |
| cg | 122 |

<210> SEQ ID NO 15
<211> LENGTH: 6978
<212> TYPE: DNA
<213> ORGANISM: Artificial Sequence
<220> FEATURE:
<223> OTHER INFORMATION: Description of Artificial Sequence: DNA
      sequence of construct CMVkan/R-R-SIVgp160 CTE

<400> SEQUENCE: 15

| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| acggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg ggaggtctat ataagcagag | 660 |
| ctcgtttagt gaaccgtcag atcgcctgga gacgccatcc acgctgtttt gacctccata | 720 |
| gaagacaccg ggaccgatcc agcctccgcg gccgcgcta agtatgggat gtcttgggaa | 780 |
| tcagctgctt atcgccatct gcttttaag tgtctatggg atctattgta ctctatatgt | 840 |
| cacagtcttt tatggtgtac cagcttggag gaatgcgaca attcccctct tttgtgcaac | 900 |
| caagaatagg gatacttggg aacaactca gtgcctacca gataatggtg attattcaga | 960 |
| agtggccctt aatgttacag aaagctttga tgcctggaat aatacagtca cagaacaggc | 1020 |
| aatagaggat gtatggcaac tctttgagac ctcaataaag ccttgtgtaa aattatcccc | 1080 |
| attatgcatt actatgagat gcaataaaag tgagacagat agatggggat tgacaaaatc | 1140 |
| aataacaaca acagcatcaa caacatcaac gacagcatca gcaaaagtag acatggtcaa | 1200 |
| tgagactagt tcttgtatag cccaggataa ttgcacaggc ttggaacaag agcaaatgat | 1260 |
| aagctgtaaa ttcaacatga cagggttaaa agagacaag aaaaaagagt acaatgaaac | 1320 |
| ttggtactct gcagatttgg tatgtgaaca agggaataac actggtaatg aaagtagatg | 1380 |
| ttacatgaac cactgtaaca cttctgttat ccaagagtct tgtgacaaac attattggga | 1440 |
| tgctattaga tttaggtatt gtgcacctcc aggttatgct ttgcttagat gtaatgacac | 1500 |
| aaattattca ggctttatgc ctaaatgttc taaggtggtg gtctcttcat gcacaaggat | 1560 |
| gatggagaca cagacttcta cttggttgg ctttaatgga actagagcag aaaatagaac | 1620 |
| ttatatttac tggcatggta gggataatag gactataatt agtttaaata gtattataa | 1680 |
| tctaacaatg aaatgtagaa gaccaggaaa taagacagtt ttaccagtca ccattatgtc | 1740 |

```
tggattggtt ttccactcac aaccaatcaa tgataggcca aagcaggcat ggtgttggtt    1800
tggaggaaaa tggaaggatg caataaaaga ggtgaagcag accattgtca acatcccag     1860 gtatactgga actaacaata ctgataaaat caatttgacg gctcctggag gaggagatcc    1920
ggaagttacc ttcatgtgga caaattgcag aggagagttc ctctactgta aaatgaattg    1980
gtttctaaat tgggtagaag ataggaatac agctaaccag aagccaaagg aacagcataa    2040
aaggaattac gtgccatgtc atattagaca ataatcaac acttggcata agtaggcaa      2100 aaatgtttat ttgcctccaa gagagggaga cctcacgtgt aactccacag tgaccagtct    2160
catagcaaac atagattgga ttgatggaaa ccaaactaat atcaccatga gtgcagaggt    2220
ggcagaactg tatcgattgg aattgggaga ttataaatta gtagagatca ctccaattgg    2280
cttggccccc acagatgtga agaggtacac tactggtggc acctcaagaa ataaaagagg    2340
ggtctttgtg ctagggttct tgggtttttct cgcaacggca ggttctgcaa tgggagccgc   2400
cagcctgacc ctcacggcac agtcccgaac tttattggct gggatagtcc aacagcagca    2460
acagctgttg gacgtggtca agagacaaca agaattgttg cgactgaccg tctgggaac     2520 aaagaacctc cagactaggg tcactgccat cgagaagtac ttaaaggacc aggcgcagct    2580
gaatgcttgg ggatgtgcgt ttagacaagt ctgccacact actgtaccat ggccaaatgc    2640
aagtctaaca ccaaagtgga acaatgagac ttggcaagag tgggagcgaa aggttgactt    2700
cttggaagaa aatataacag ccctcctaga ggaggcacaa attcaacaag agaagaacat    2760
gtatgaatta caaagttga atagctggga tgtgtttggc aattggtttg accttgcttc     2820
ttggataaag tatatacaat atggagttta tagttgta ggagtaatac tgttaagaat      2880
agtgatctat atagtacaaa tgctagctaa gttaaggcag gggtataggc cagtgttctc    2940
ttccccaccc tcttatttcc agcagaccca tatccaacag gacccggcac tgccaaccag    3000
agaaggcaaa gaaagagacg gtggagaagg cggtggcaac agctcctggc cttggcagat    3060
agaatatatc cactttctta ttcgtcagct tattagactc ttgacttggc tattcagtaa    3120
ctgtaggact ttgctatcga gagtatacca gatcctccaa ccaatactcc agaggctctc    3180
tgcgacccta cagaggattc gagaagtcct caggactgaa ctgacctacc tacaatatgg    3240
gtggagctat ttcatgagg cggtccaggc cgtctggaga tctgcgacag agactcttgc     3300
gggcgcgtgg ggagacttat gggagactct taggagaggt ggaagatgga tactcgcaat    3360
ccccaggagg attagacaag ggcttgagct cactctcttg tgaggacag agaattcgga     3420 tccactagtt ctagactcga gggggggccc ggtacgagcg cttagctagc tagagaccac    3480
ctcccctgcg agctaagctg gacagccaat gacgggtaag agagtgacat ttttcactaa    3540
cctaagacag gagggccgtc agagctactg cctaatccaa agacgggtaa aagtgataaa    3600
aatgtatcac tccaacctaa gacagcgca gcttccgagg gatttgtcgt ctgttttata    3660
tatatttaaa agggtgacct gtccggagcc gtgctgcccg gatgatgtct tggtctagac    3720
tcgagggggg gcccggtacg atccagatct gctgtgcctt ctagttgcca gccatctgtt    3780
gtttgcccct cccccgtgcc ttccttgacc ctggaaggtg ccactcccac tgtcctttcc    3840
taataaaatg aggaaattgc atcgcattgt ctgagtaggt gtcattctat tctgggggt     3900 ggggtgggc agcacagcaa gggggaggat tgggaagaca atagcaggca tgctgggat      3960 gcggtgggct ctatgggtac ccaggtgctg aagaattgac ccggttcctc ctgggccaga    4020
aagaagcagg cacatcccct tctctgtgac acaccctgtc cacgccctg gttcttagtt     4080 ccagccccac tcataggaca ctcatagctc aggagggctc cgccttcaat cccacccgct    4140
```

-continued

```
aaagtacttg gagcggtctc tccctccctc atcagcccac caaaccaaac ctagcctcca    4200
agagtgggaa gaaattaaag caagataggc tattaagtgc agaggagag  aaaatgcctc    4260 caacatgtga ggaagtaatg agagaaatca tagaatttct tccgcttcct cgctcactga    4320
ctcgctgcgc tcggtcgttc ggctgcggcg agcggtatca gctcactcaa aggcggtaat    4380
acggttatcc acagaatcag gggataacgc aggaaagaac atgtgagcaa aaggccagca    4440
aaaggccagg aaccgtaaaa aggccgcgtt gctggcgttt ttccataggc tccgcccccc    4500
tgacgagcat cacaaaaatc gacgctcaag tcagaggtgg cgaaacccga caggactata    4560
aagataccag gcgtttcccc ctggaagctc cctcgtgcgc tctcctgttc cgaccctgcc    4620
gcttaccgga tacctgtccg cctttctccc ttcgggaagc gtggcgcttt ctcaatgctc    4680
acgctgtagg tatctcagtt cggtgtaggt cgttcgctcc aagctgggct gtgtgcacga    4740
accccccgtt cagcccgacc gctgcgcctt atccggtaac tatcgtcttg agtccaaccc    4800
ggtaagacac gacttatcgc cactggcagc agccactggt aacaggatta gcagagcgag    4860
gtatgtaggc ggtgctacag agttcttgaa gtggtggcct aactacggct acactagaag    4920
gacagtattt ggtatctgcg ctctgctgaa gccagttacc ttcggaaaaa gagttggtag    4980
ctcttgatcc ggcaaacaaa ccaccgctgg tagcggtggt ttttttgttt gcaagcagca    5040
gattacgcgc agaaaaaaag gatctcaaga agatcctttg atcttttcta cggggtctga    5100
cgctcagtgg aacgaaaact cacgttaagg gattttggtc atgagattat caaaaaggat    5160
cttcacctag atccttttaa attaaaaatg aagttttaaa tcaatctaaa gtatatatga    5220
gtaaacttgg tctgacagtt accaatgctt aatcagtgag gcacctatct cagcgatctg    5280
tctatttcgt tcatccatag ttgcctgact ccggggggg ggggcgctga ggtctgcctc    5340
gtgaagaagg tgttgctgac tcataccagg cctgaatcgc cccatcatcc agccagaaag    5400
tgagggagcc acggttgatg agagctttgt tgtaggtgga ccagttggtg attttgaact    5460
tttgctttgc cacggaacgg tctgcgttgt cgggaagatg cgtgatctga tccttcaact    5520 cagcaaagt  tcgattatt  caacaaagcc gccgtcccgt caagtcagcg taatgctctg    5580
ccagtgttac aaccaattaa ccaattctga ttagaaaaac tcatcgagca tcaaatgaaa    5640
ctgcaattta ttcatatcag gattatcaat accatatttt tgaaaagcc  gtttctgtaa    5700 tgaaggagaa aactcaccga ggcagttcca taggatggca agatcctggt atcggtctgc    5760
gattccgact cgtccaacat caatacaacc tattaatttc ccctcgtcaa aaataaggtt    5820
atcaagtgag aaatcaccat gagtgacgac tgaatccggt gagaatggca aaagcttatg    5880
catttctttc cagacttgtt caacaggcca gccattacgc tcgtcatcaa aatcactcgc    5940
atcaaccaaa ccgttattca ttcgtgattg cgcctgagcg agacgaaata cgcgatcgct    6000
gttaaaagga caattacaaa caggaatcga atgcaaccgg cgcaggaaca ctgccagcgc    6060
atcaacaata ttttcacctg aatcaggata ttcttctaat acctggaatg ctgttttccc    6120
ggggatcgca gtggtgagta accatgcatc atcaggagta cggataaaat gcttgatggt    6180
cggaagaggc ataaattccg tcagccagtt tagtctgacc atctcatctg taacatcatt    6240
ggcaacgcta cctttgccat gtttcagaaa caactctggc gcatcgggct tcccatacaa    6300
tcgatagatt gtcgcacctg attgcccgac attatcgcga gcccatttat acccatataa    6360
atcagcatcc atgttggaat ttaatcgcgg cctcgagcaa gacgtttccc gttgaatatg    6420
gctcataaca ccccttgtat tactgtttat gtaagcagac agttttattg ttcatgatga    6480
```

-continued

```
tatatttta tcttgtgcaa tgtaacatca gagattttga cacaacgt ggctttcccc      6540 ccccccccat tattgaagca tttatcaggg ttattgtctc atgagcggat acatatttga    6600
atgtatttag aaaaataaac aaataggggt tccgcgcaca tttccccgaa aagtgccacc    6660
tgacgtctaa gaaaccatta ttatcatgac attaacctat aaaaataggc gtatcacgag    6720
gccctttcgt ctcgcgcgtt tcggtgatga cggtgaaaac ctctgacaca tgcagctccc    6780
ggagacggtc acagcttgtc tgtaagcgga tgccgggagc agacaagccc gtcagggcgc    6840
gtcagcgggt gttggcgggt gtcggggctg gcttaactat gcggcatcag agcagattgt    6900
actgagagtg caccatatgc ggtgtgaaat accgcacaga tgcgtaagga gaaaataccg    6960
catcagattg gctattgg                                                  6978
```

<210> SEQ ID NO 16
<211> LENGTH: 879
<212> TYPE: PRT
<213> ORGANISM: Artificial Sequence
<220> FEATURE:
<223> OTHER INFORMATION: Description of Artificial Sequence: SIV
      gp160env IN PLASMID CMVkan/R-R-SIVgp160 CTE

<400> SEQUENCE: 16

```
Met Gly Cys Leu Gly Asn Gln Leu Leu Ile Ala Ile Leu Leu Leu Ser
 1               5                  10                  15

Val Tyr Gly Ile Tyr Cys Thr Leu Tyr Val Thr Val Phe Tyr Gly Val
            20                  25                  30

Pro Ala Trp Arg Asn Ala Thr Ile Pro Leu Phe Cys Ala Thr Lys Asn
        35                  40                  45

Arg Asp Thr Trp Gly Thr Thr Gln Cys Leu Pro Asp Asn Gly Asp Tyr
    50                  55                  60

Ser Glu Val Ala Leu Asn Val Thr Glu Ser Phe Asp Ala Trp Asn Asn
65                  70                  75                  80

Thr Val Thr Glu Gln Ala Ile Glu Asp Val Trp Gln Leu Phe Glu Thr
                85                  90                  95

Ser Ile Lys Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ile Thr
        115                 120                 125

Thr Thr Ala Ser Thr Thr Ser Thr Thr Ala Ser Ala Lys Val Asp Met
    130                 135                 140

Val Asn Glu Thr Ser Ser Cys Ile Ala Gln Asp Asn Cys Thr Gly Leu
145                 150                 155                 160

Glu Gln Glu Gln Met Ile Ser Cys Lys Phe Asn Met Thr Gly Leu Lys
                165                 170                 175

Arg Asp Lys Lys Lys Glu Tyr Asn Glu Thr Trp Tyr Ser Ala Asp Leu
            180                 185                 190

Val Cys Glu Gln Gly Asn Asn Thr Gly Asn Glu Ser Arg Cys Tyr Met
        195                 200                 205

Asn His Cys Asn Thr Ser Val Ile Gln Glu Ser Cys Asp Lys His Tyr
    210                 215                 220

Trp Asp Ala Ile Arg Phe Arg Tyr Cys Ala Pro Pro Gly Tyr Ala Leu
225                 230                 235                 240

Leu Arg Cys Asn Asp Thr Asn Tyr Ser Gly Phe Met Pro Lys Cys Ser
                245                 250                 255

Lys Val Val Val Ser Ser Cys Thr Arg Met Met Glu Thr Gln Thr Ser
            260                 265                 270
```

-continued

```
Thr Trp Phe Gly Phe Asn Gly Thr Arg Ala Glu Asn Arg Thr Tyr Ile
        275                 280                 285
Tyr Trp His Gly Arg Asp Asn Arg Thr Ile Ile Ser Leu Asn Lys Tyr
    290                 295                 300
Tyr Asn Leu Thr Met Lys Cys Arg Arg Pro Gly Asn Lys Thr Val Leu
305                 310                 315                 320
Pro Val Thr Ile Met Ser Gly Leu Val Phe His Ser Gln Pro Ile Asn
                    325                 330                 335
Asp Arg Pro Lys Gln Ala Trp Cys Trp Phe Gly Lys Trp Lys Asp
            340                 345                 350
Ala Ile Lys Glu Val Lys Gln Thr Ile Val Lys His Pro Arg Tyr Thr
            355                 360                 365
Gly Thr Asn Asn Thr Asp Lys Ile Asn Leu Thr Ala Pro Gly Gly Gly
    370                 375                 380
Asp Pro Glu Val Thr Phe Met Trp Thr Asn Cys Arg Gly Glu Phe Leu
385                 390                 395                 400
Tyr Cys Lys Met Asn Trp Phe Leu Asn Trp Val Glu Asp Arg Asn Thr
                405                 410                 415
Ala Asn Gln Lys Pro Lys Glu Gln His Lys Arg Asn Tyr Val Pro Cys
            420                 425                 430
His Ile Arg Gln Ile Ile Asn Thr Trp His Lys Val Gly Lys Asn Val
    435                 440                 445
Tyr Leu Pro Pro Arg Glu Gly Asp Leu Thr Cys Asn Ser Thr Val Thr
    450                 455                 460
Ser Leu Ile Ala Asn Ile Asp Trp Ile Asp Gly Asn Gln Thr Asn Ile
465                 470                 475                 480
Thr Met Ser Ala Glu Val Ala Glu Leu Tyr Arg Leu Glu Leu Gly Asp
                485                 490                 495
Tyr Lys Leu Val Glu Ile Thr Pro Ile Gly Leu Ala Pro Thr Asp Val
            500                 505                 510
Lys Arg Tyr Thr Thr Gly Gly Thr Ser Arg Asn Lys Arg Gly Val Phe
            515                 520                 525
Val Leu Gly Phe Leu Gly Phe Leu Ala Thr Ala Gly Ser Ala Met Gly
530                 535                 540
Ala Ala Ser Leu Thr Leu Thr Ala Gln Ser Arg Thr Leu Leu Ala Gly
545                 550                 555                 560
Ile Val Gln Gln Gln Gln Leu Leu Asp Val Val Lys Arg Gln Gln
                565                 570                 575
Glu Leu Leu Arg Leu Thr Val Trp Gly Thr Lys Asn Leu Gln Thr Arg
            580                 585                 590
Val Thr Ala Ile Glu Lys Tyr Leu Lys Asp Gln Ala Gln Leu Asn Ala
            595                 600                 605
Trp Gly Cys Ala Phe Arg Gln Val Cys His Thr Thr Val Pro Trp Pro
    610                 615                 620
Asn Ala Ser Leu Thr Pro Lys Trp Asn Glu Thr Trp Gln Glu Trp
625                 630                 635                 640
Glu Arg Lys Val Asp Phe Leu Glu Glu Asn Ile Thr Ala Leu Leu Glu
                645                 650                 655
Glu Ala Gln Ile Gln Gln Glu Lys Asn Met Tyr Glu Leu Gln Lys Leu
            660                 665                 670
Asn Ser Trp Asp Val Phe Gly Asn Trp Phe Asp Leu Ala Ser Trp Ile
    675                 680                 685
```

-continued

```
Lys Tyr Ile Gln Tyr Gly Val Tyr Ile Val Gly Val Ile Leu Leu
    690                 695                 700

Arg Ile Val Ile Tyr Ile Val Gln Met Leu Ala Lys Leu Arg Gln Gly
705                 710                 715                 720

Tyr Arg Pro Val Phe Ser Ser Pro Ser Tyr Phe Gln Gln Thr His
                    725                 730                 735

Ile Gln Gln Asp Pro Ala Leu Pro Thr Arg Glu Gly Lys Glu Arg Asp
            740                 745                 750

Gly Gly Glu Gly Gly Gly Asn Ser Ser Trp Pro Trp Gln Ile Glu Tyr
                755                 760                 765

Ile His Phe Leu Ile Arg Gln Leu Ile Arg Leu Leu Thr Trp Leu Phe
        770                 775                 780

Ser Asn Cys Arg Thr Leu Ser Arg Val Tyr Gln Ile Leu Gln Pro
785                 790                 795                 800

Ile Leu Gln Arg Leu Ser Ala Thr Leu Gln Arg Ile Arg Glu Val Leu
                805                 810                 815

Arg Thr Glu Leu Thr Tyr Leu Gln Tyr Gly Trp Ser Tyr Phe His Glu
                820                 825                 830

Ala Val Gln Ala Val Trp Arg Ser Ala Thr Glu Thr Leu Ala Gly Ala
            835                 840                 845

Trp Gly Asp Leu Trp Glu Thr Leu Arg Arg Gly Gly Arg Trp Ile Leu
    850                 855                 860

Ala Ile Pro Arg Arg Ile Arg Gln Gly Leu Glu Leu Thr Leu Leu
865                 870                 875

<210> SEQ ID NO 17
<211> LENGTH: 271
<212> TYPE: PRT
<213> ORGANISM: Escherichia coli

<400> SEQUENCE: 17

Met Ser His Ile Gln Arg Glu Thr Ser Cys Ser Arg Pro Arg Leu Asn
  1               5                  10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
 65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190
```

```
Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
        210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
                260                 265                 270

<210> SEQ ID NO 18
<211> LENGTH: 2640
<212> TYPE: DNA
<213> ORGANISM: Artificial Sequence
<220> FEATURE:
<223> OTHER INFORMATION: Description of Artificial Sequence: DNA
      sequence of mutated SIV gene in construct
      CMVkan/R-R-SIVgp160 CTE

<400> SEQUENCE: 18
atgggatgtc ttgggaatca gctgcttatc gccatcttgc ttttaagtgt ctatgggatc      60
tattgtactc tatatgtcac agtctttat ggtgtaccag cttggaggaa tgcgacaatt     120
cccctctttt gtgcaaccaa gaatagggat acttggggaa caactcagtg cctaccagat     180
aatggtgatt attcagaagt ggcccttaat gttacgaaa gctttgatgc ctggaataat     240
acagtcacag aacaggcaat agaggatgta tggcaactct ttgagacctc aataaagcct     300
tgtgtaaaat tatccccatt atgcattact atgagatgca ataaaagtga gacagataga     360
tggggattga caaaatcaat aacaacaaca gcatcaacaa catcaacgac agcatcagca     420
aaagtagaca tggtcaatga gactagttct tgtatagccc aggataattg cacaggcttg     480
gaacaagagc aaatgataag ctgtaaattc aacatgacag ggttaaaaag agacaagaaa     540
aaagagtaca atgaaacttg gtactctgca gatttggtat gtgaacaagg aataacact      600 ggtaatgaaa gtagatgtta catgaaccac tgtaacactt ctgttatcca gagtcttgt      660 gacaaacatt attgggatgc tattagattt aggtattgtg cacctccagg ttatgctttg     720
cttagatgta atgacacaaa ttattcaggc tttatgccta atgttctaa ggtggtggtc      780 tcttcatgca caaggatgat ggagacacag acttctactt ggtttggctt taatggaact     840
agagcagaaa atagaactta tatttactgg catggtaggg ataataggac tataattagt     900
ttaaataagt attataatct aacaatgaaa tgtagaagac caggaaataa gacagtttta     960
ccagtcacca ttatgtctgg attggttttc cactcacaac caatcaatga taggccaaag    1020
caggcatggt gttggtttgg aggaaaatgg aaggatgcaa taaagaggt gaagcagacc     1080 attgtcaaac atcccaggta tactggaact aacaatactg ataaaatcaa tttgacggct    1140
cctggaggag gagatccgga agttaccttc atgtggacaa attgcagagg agagttcctc    1200
tactgtaaaa tgaattggtt tctaaattgg gtagaagata ggaatacagc taaccagaag    1260
ccaaaggaac agcataaaag gaattacgtg ccatgtcata ttagacaaat aatcaacact    1320
tggcataaag taggcaaaaa tgtttatttg cctccaagag agggagacct cacgtgtaac    1380
tccacagtga ccagtctcat agcaaacata gattggattg atggaaaacca actaatatc    1440 accatgagtg cagaggtggc agaactgtat cgattggaat tgggagatta taaattagta    1500
gagatcactc caattggctt ggcccccaca gatgtgaaga ggtacactac tggtggcacc    1560
```

```
tcaagaaata aaagagggt ctttgtgcta gggttcttgg gttttctcgc aacggcaggt    1620
tctgcaatgg gagccgccag cctgaccctc acggcacagt cccgaacttt attggctggg    1680
atagtccaac agcagcaaca gctgttggac gtggtcaaga acaacaaga attgttgcga    1740 ctgaccgtct ggggaacaaa gaacctccag actagggtca ctgccatcga aagtactta    1800 aaggaccagg cgcagctgaa tgcttgggga tgtgcgttta acaagtctg ccacactact    1860 gtaccatggc caaatgcaag tctaacacca aagtggaaca atgagacttg caagagtgg    1920 gagcgaaagg ttgacttctt ggaagaaaat ataacagccc tcctagagga ggcacaaatt    1980
caacaagaga agaacatgta tgaattacaa agttgaata gctgggatgt gtttggcaat    2040
tggtttgacc ttgcttcttg gataaagtat atacaatatg gagtttatat agttgtagga    2100
gtaatactgt taagaatagt gatctatata gtacaaatgc tagctaagtt aaggcagggg    2160
tataggccag tgttctcttc cccaccctct tatttccagc agaccatat ccaacaggac    2220 ccggcactgc caaccagaga aggcaaagaa agagacggtg gagaaggcgg tggcaacagc    2280
tcctggcctt ggcagataga atatatccac tttcttattc gtcagcttat tagactcttg    2340
acttggctat tcagtaactg taggactttg ctatcgagag tataccagat cctccaacca    2400
atactccaga ggctctctgc gaccctacag aggattcgag aagtcctcag gactgaactg    2460
acctacctac aatatgggtg gagctatttc catgaggcgg tccaggccgt ctggagatct    2520
gcgacagaga ctcttgcggg cgcgtgggga gacttatggg agactcttag gagaggtgga    2580
agatggatac tcgcaatccc caggaggatt agacaagggc ttgagctcac tctcttgtga    2640

<210> SEQ ID NO 19
<211> LENGTH: 813
<212> TYPE: DNA
<213> ORGANISM: Escherichia coli

<400> SEQUENCE: 19
atgagccata ttcaacggga aacgtcttgc tcgaggccgc gattaaattc caacatggat      60
gctgatttat atgggtataa atgggctcgc gataatgtcg ggcaatcagg tgcgacaatc     120
tatcgattgt atgggaagcc cgatgcgcca gagttgtttc tgaaacatgg caaaggtagc     180
gttgccaatg atgttacaga tgagatggtc agactaaact ggctgacgga atttatgcct     240
cttccgacca tcaagcattt tatccgtact cctgatgatg catggttact caccactgcg     300
atccccggga aaacagcatt ccaggtatta gaagaatatc ctgattcagg tgaaaatatt     360
gttgatgcgc tggcagtgtt cctgcgccgg ttgcattcga ttcctgtttg taattgtcct     420
tttaacagcg atcgcgtatt tcgtctcgct caggcgcaat cacgaatgaa taacggtttg     480
gttgatgcga gtgattttga tgacgagcgt aatggctggc ctgttgaaca agtctggaaa     540
gaaatgcata gcttttgcc attctcaccg gattcagtcg tcactcatgg tgatttctca     600
cttgataacc ttatttttga cgaggggaaa ttaataggtt gtattgatgt tggacgagtc     660
ggaatcgcag accgatacca ggatcttgcc atcctatgga actgcctcgg tgagttttct     720
ccttcattac agaaacggct ttttcaaaaa tatggtattg ataatcctga tatgaataaa     780
ttgcagtttc atttgatgct cgatgagttt ttc                                   813
```

What is claimed is:

1. A nucleic acid construct comprising a HIV-1 gag/pol gene having the coding sequence of the gag/pol gene set forth in FIG. 1 (SEQUENCE ID NO: 1).

2. A nucleic acid construct comprising a HIV-1 pol gene having the coding sequence of the pol gene set forth in FIG. 2 (SEQUENCE ID NO: 3).

3. A nucleic acid construct comprising an HIV or SIV 5' LTR, a packaging signal, a gag/pol gene comprising the sequence set forth in FIG. 1 (SEQUENCE ID NO: 1), a 5' splice site, a 3' splice site, an env gene, a tat gene, a functional RNA transport element and a 3' HIV or SIV LTR, said nucleic acid construct being able to produce functional Gag. Pol and Env virion components.

4. A vector comprising the nucleic acid construct of claim 1, 2 or 3.

5. An isolated host cell comprising the nucleic acid construct of claim 1, 2 or 3.

6. The host cell of claim 5 wherein said cell is a eukaryote.

7. The host cell of claim 6 wherein said cell is a human cell.

8. The host cell of claim 5 wherein said cell is a prokaryote.

9. The host cell of claim 8 wherein said cell is E. coli.

10. A composition comprising the nucleic acid A construct of claim 1, 2, or 3 and a pharmaceutically acceptable carrier.

11. A lentiviral expression system comprising the following:

(a) a packaging vector comprising a HIV-1 gag/pol gene having the nucleotide sequence set forth in FIG. 1 (SEQUENCE ID NO: 1);

(b) a transfer vector; and (c) an envelope encoding vector.

12. An isolated host cell comprising the lentiviral expression system of claim 11.

13. The host cell of claim 12, wherein said cell is a eukaryote.

14. The host cell of claim 13 wherein said cell is a human cell.

15. A process for making a lentiviral particle comprising expressing, in a host cell, HIV Gag and HIV Pol from a vector comprising the nucleotide sequences encoding HIV Gag and HIV Pol set forth in FIG. 1 (SEQUENCE ID NO: 1) and expressing a gene encoding an envelope protein by growing the host cell under conditions suitable to cause expression of HIV Gag, HIV Pol and envelope protein so that a lentiviral particle is formed.

16. A lentiviral expression system which is capable of functioning in the absence of Rev, Tat, and any viral RNA transport element comprising the following:

(a) a packaging vector comprising a HIV-1 gag/pol gene which is capable of functioning in the absence of Rev, Tat, and any viral RNA transport element;

(b) a transfer vector; and (c) an envelope encoding vector wherein the HIV-1 gag/pol gene has the coding sequence of the HIV-1 gag/pol gene set forth in FIG. 1 (SEQUENCE ID NO: 1).

17. A process for making a lentiviral particle in the absence of Rev, Tat, or any viral RNA transport element comprising expressing HIV Gag and HIV Pol in a host cell from a HIV-1 gag/pol gene which is capable of functioning in the absence of Rev, Tat, and any viral RNA transport element and expressing an Envelope protein from a envelope encoding gene whose expression is independent of Rev, Tat, or any viral RNA transport element wherein the HIV-1 gag/pol gene has the coding sequence of the HIV-1 gag/pol gene set forth in FIG. 1 (SEQUENCE ID NO: 1).

18. The lentiviral expression system of claim 16 wherein the packaging vector has the DNA sequence of packaging construct pCMVgag/polBNKan set forth in FIG. 9 (SEQUENCE ID NO: 6).

19. The lentiviral expression system of claim 16 wherein the transfer vector has the DNA sequence of pmBCwCNluci set forth in FIG. 10 (SEQUENCE ID NO: 8) or pmBCmCNluci set forth in FIG. 11 (SEQUENCE ID NO: 9).

20. An isolated host cell comprising the lentiviral expression system of claim 16.

21. The host cell of claim 20 wherein said cell is a eukaryote.

22. The host cell of claim 21 wherein said cell is a human cell.

* * * * *